US006815532B2

(12) United States Patent
Loughney et al.

(10) Patent No.: US 6,815,532 B2
(45) Date of Patent: Nov. 9, 2004

(54) ATR-2 CELL CYCLE CHECKPOINT

(75) Inventors: Kate Loughney, Seattle, WA (US); Kathleen S. Keegan, Mercer Island, WA (US)

(73) Assignee: ICOS Corporation, Bothell, WA (US)

( * ) Notice: Subject to any disclaimer, the term of this patent is extended or adjusted under 35 U.S.C. 154(b) by 345 days.

(21) Appl. No.: 09/957,837

(22) Filed: Sep. 21, 2001

(65) Prior Publication Data

US 2003/0023055 A1 Jan. 30, 2003

Related U.S. Application Data

(62) Division of application No. 09/417,822, filed on Oct. 14, 1999, now Pat. No. 6,344,549.

(51) Int. Cl.[7] .......................... C07K 1/00; C07H 21/04
(52) U.S. Cl. ...................................... 530/350; 536/23.2
(58) Field of Search ........................ 530/350; 536/23.2; 930/240

(56) References Cited

U.S. PATENT DOCUMENTS 5,283,173 A    2/1994  Fields et al.

FOREIGN PATENT DOCUMENTS

| WO | WO 91/09955 | 7/1991 |
| WO | WO 92/20808 | 11/1992 |
| WO | WO 93/11236 | 6/1993 |
| WO | WO 94/12650 | 6/1994 |
| WO | WO 95/20652 | 8/1995 |
| WO | WO 97/09433 | 3/1997 |
| WO | WO 98/13502 | 4/1998 |

OTHER PUBLICATIONS

Altschul, et al., "Basic Local Alignment Search Tool" *J. Mol. Biol.* 215:403–410 (1990).
Anderson, "Human gene therapy" *Nature* supplement to vol. 392:25–30 (1998).
Ausubel, et al., "Screening of Recombinant DNA Libraries," *Protocols in Molecular Biology*, pp. 6.0.3–6.4.10 (1994).
Bramlage, et al., "Designing ribozymes for the inhibition of gene expression" *Trends in Biotech* 16:434–438 (1998).
Cane, et al., "Harnessing the Biosynthetic Code: Combinations, Permutations, and Mutations" *Science* 282:63–68 (1998).
Capecchi, "Altering the Genome by Homologous Recombination" *Science* 244:1288–1292 (1989).
Cliby, et al., "Overexpression of a kinase–inactive ATR protein causes sensitivity to DNA–damaging agents and defects in cell cycle checkpoints" *EMBO J.* 17:159–169 (1998).
Colas, et al., "The impact of two–hybrid and related methods on biotechnology" *TIBTECH* 16:355–363 (1998).
Corey, "Peptide nucleic acids: expanding the scope of nucleic acid recognition" *TIBTECH* 15:224–229 (1997).
Culbertson, et al., "RNA surveillance unforeseen consequences for gene expression, inherited genetic disorders and cancer" *Trends in Genet.* 15:74–80 (1999).
Dayhoff, in *Atlas of Protein Sequence and Structure*, National Biochemical; Research Foundation, Washington, D.C. 5:124 (1972).
Devereux, et al., "A comprehensive set of sequence analysis programs for the VAX" *Nucleic Acids Research* 12(1):387 (1984).
Diaz–Meco, et al., "Lambda–Interacting Protein, a Novel Protein That Specifically Interacts with the Zinc Finger Domain of the Atypical Protein Kinase C Isotype λ/ι and Stimulates Its Kinase Activity In Vitro and In Vivo" *Mol. Cell Biol.* 16:105–114 (1996).
Fan, et al., "Immunization via hair follicles by topical application of naked DNA to normal skin" *Nat. Biotech.* 17:870–872 (1999).
Fields, et al., "A novel genetic system to detect protein–protein interactions" *Nature* 340:245–246 (1989).
Fields, "The Two–Hybrid System to Detect Protein–Protein Interactions" *Methods: A Companion to Methods in Enzymology* 5:116–124 (1993).
Friedmann, "Progress Toward Human Gene Therapy" *Science* 244:1275–1281 (1989).
Gibson, et al., "Review: Ribozymes, Their Functions and Strategies for Their Use" *Mol. Biotech.* 7:125–137 (1997).
Harlow, et al., "Monoclonal Antibodies," *Antibodies: A Laboratory Manual*, 6:139–243 (1988).
Haupt, et al., "Plastic antibodies: developments and applications" *TIBTECH* 16:468–475 (1998).
Henikoff, et al., "Amino acid substitution matrices from protein blocks" *Proc. Natl. Acad. Sci USA* 89:10915–10919 (1992).
Houston, et al., "The chemical–biological interface: developments in automated and miniaturised screening technology" *Curr. Opin. Biotechnol.* 8:734–740 (1997).
Ishikawa, et al., "Prediction of the Coding Sequences of Unidentified Human Genes. VIII. 78 New cDNA Clones from Brain Which Code for Large Proteins in vitro" *DNA Res.* 4:307–313 (1997).
Jayawickreme, et al., "Gene expression systems in the development of high–throughput screens" *Curr. Opin. Biotechnol.* 8:629–634 (1997).
Keegan, et al., "The Atr and Atm protein kinases associate with different sites along meiotically pairing chromosomes," *Genes Dev.* 10:2423–2437 (1996).
Krstenansky, et al., "Antithrombin properties of C–terminus of hirudin using synthetic unsulfated $N^{\alpha}$–acetyl–hirudin" *FEBS Lett.* 211:10 (1987).

(List continued on next page.)

*Primary Examiner*—Gary B. Nickol
(74) *Attorney, Agent, or Firm*—Marshall, Gerstein & Borun LLP

(57) ABSTRACT

Polynucleotides encoding novel Atr-2 cell cycle checkpoint polypeptides are disclosed, along with expression constructs comprising the polynucleotides, host cells transformed with the expression constructs, methods to make the Atr-2 polypeptides using the host cells, Atr-2 polypeptides, and binding partners of the Atr-2 polypeptides.

3 Claims, No Drawings

OTHER PUBLICATIONS

Kuruvilla, et al., "The PIK–related kinases intercept conventional signaling pathways" *Chemistry and Biology* 6:R129–R136 (1999).

Lavrovsky, et al., "Review: Therapeutic Potential and Mechanism of Action of Oligonucleotides and Ribozymes" *Biochem. Mol. Med.* 62:11–22 (1997).

Lehman, et al., "The ataxia–telangiectasia gene: a link between checkpoint controls, neurodegeneration and cancer" *Trends in Genet.* 11:375–377 (1995).

Lehninger, "The Molecular Basis of Cell Structure and Fiction" *Biochemistry*, Second Edition; Worth Publishers, Inc., NY:NY, pp. 71–77 (1975).

McMahon, et al., "The Novel ATM–Related Protein TRRAP Is an Essential Cofactor for the c–Myc and E2F Oncoproteins" *Cell* 94:363–374 (1998).

Merrifield, "Solid Phase Peptide Synthesis. I. The Synthesis of a Tetrapeptide[1]" *J. Amer. Chem. Soc.* 85:2149–2154 (1963).

Miller, "Human gene therapy comes of age" *Nature* 357:455–460 (1992).

Myers, "Will combinatorial chemistry deliver real medicines?" *Curr. Opin. Biotechnol.* 8:701–707 (1997).

Needleman, et al., "A General Method Applicable to the Search for Similarities in the Amino Acid Sequence of Two Proteins" *J. Mol. Biol.* 48:443–453 (1970).

Page, et al., "SMG–2 Is a Phosphorylated Protein Required for mRNA Surveillance in *Caenorhabditis elegans* and Related to Upflp of Yeast" *Mol. Cell. Biol.* 9:5943–5951 (1999).

Painter, et al., "Radiosensitivity in ataxia–telangiectasia: A new explanation" *Proc. Natl. Acad. Sci.* (*USA*) 77:7315–7317 (1980).

*Remington's Pharmaceutical Sciences*, 18th Ed., Mack Publishing Co., Easton, PA 18042, pp. 1435–1712 (1990).

Sambrook, et al., (Eds.), "Hybridization of Radiolabeled Probes to Immubilized Nucleic Acids," *Molecular Cloning: A Laboratory Manual*, Cold Spring Harbor Laboratory Press: Cold Spring Harbor, New York, pp. 9.47–9.51 (1989).

Schwarze, et al., "In Vivo Protein Transduction: Delivery of a Biologically Active Protein into the Mouse," *Science* 285:1569–1572 (1999).

Smith, et al., "Duplication of ATR inhibits MyoD, induces aneuploidy and eliminates radiation–induced G1 arrest" *Nat. Genetics* 19:39–46 (1998).

Verma, "Gene Therapy: Treatment of disease by introducing healthy genes into the body is becoming feasible. But the therapy will not reach its full potential until the genes can be coaxed to work throughout life," *Scientific American* 68:84 (1990).

Wright, et al., "Protein kinase mutants of human ATR increase sensitivity to UV and ionizing radiation and abrogate cell cycle checkpoint control" *Proc. Natl. Acad. Sci.* (*USA*) 95:7445–7450 (1998).

ATR-2 CELL CYCLE CHECKPOINT

This application is a divisional application of U.S. patent application Ser. No. 09/417,822, filed Oct. 14, 1999, now U.S. Pat. No. 6,344,549.

FIELD OF THE INVENTION

The present invention relates to novel polynucleotides encoding cell cycle checkpoint polypeptides.

BACKGROUND

The mitotic cell cycle is the process by which a cell creates an exact copy of its chromosomes and then segregates each copy into two cells. The sequence of events of the cell cycle is carefully regulated such that cell division does not occur until the cell has completed DNA replication and, DNA replication does not occur until cells have completed mitosis. If a cell is exposed to DNA damage, the damage is repaired before the cell undergoes cell division. Regulation of these processes ensures that an exact copy of DNA is propagated to the daughter cells. The cell cycle has been divided into four phases: G1, S, G2, and M. During the G1 phase, cells undergo activities that prepare for DNA replication. S, or synthesis, phase begins as cells initiate DNA replication and ends with the formation of two identical copies of each chromosome. G2, the stage that begins after replication is complete, is when cells ensure that they contain components needed for mitosis. M phase, or mitosis, is the stage at which the cells divide each identical chromosome into two daughter cells.

Cells have mechanisms for sensing correct cell cycle progression and exposure to DNA damage, and proteins involved in these sensing mechanisms are termed checkpoints. Checkpoints signal cell cycle arrest to allow for completion of relevant events or repair of DNA damage. There are checkpoints that monitor progression through the cycle at G1, S, G2, and M. DNA damage checkpoints also exist at these stages of the cell cycle. Failure to correct DNA damage may signal the cell to undergo programmed cell death or apoptosis.

Members of the phosphatidylinositol kinase (PIK)-related family of kinases are involved in cell cycle checkpoints and DNA damage repair. To date, five PIK-related protein kinases have been identified. Genes in this family, which includes ATM, ATR, FRAP and DNA-PKcs, encode large proteins (280–450 kD) that exhibit homology to kinases at the carboxy terminus. While the predicted amino acid sequences of the kinase domains are most closely related to lipid kinases, all have been shown to function as protein kinases, and, presumably, each of these proteins participate in a signal transduction cascade leading to cell cycle arrest, cell cycle progression, and/or DNA repair.

The ataxia-telangiectasia mutated (ATM) gene product has been shown to play a role in a DNA damage checkpoint in response to ionizing radiation (IR). Patients lacking functional ATM develop the disease ataxia-telangiectasia (A-T). Symptoms of A-T include extreme sensitivity to irradiation, cerebellar degeneration, oculocutaneous telangiectasias, gonadal deficiencies, immunodeficiencies, and increased risk of cancer [Lehman and Carr, *Trends in Genet.* 11:375–377 (1995)]. Fibroblasts derived from these patients show defects in G1, S, and G2 checkpoints [Painter and Young, *Proc. Natl. Acad. Sci. (USA)* 77:7315–7317 (1980)] and are defective in their response to irradiation. ATM is thought to sense double strand DNA damage caused by irradiation and radiomimetic drugs, and to signal cell cycle arrest so that the damage can be repaired.

The DNA-stimulated protein kinase, DNA-PKcs has been demonstrated to play an important role in repair of double strand breaks. Mice defective in DNA-PK demonstrate immunodeficiencies and sensitivity to irradiation. In addition, these mice are defective in V(D)J recombination. These results suggest that DNA-PK plays a role in repairing normal double strand DNA breaks generated during V(D)J recombination, as well as double strand breaks generated by DNA damaging agents. While DNA-PK defective cells have not been shown to be deficient in cell cycle checkpoints, it is reasonable to assume that the cell cycle must arrest, if only transiently, in order to repair double strand breaks.

ATR has been found to act as a checkpoint protein stimulated by agents that cause double strand DNA breaks, agents that cause single strand DNA breaks, and agents that block DNA replication [Cliby, et al., *EMBO J.* 17:159–169 (1998); Wright, et al., *Proc. Natl. Acad. Sc. (USA)* 95:7445–7450 (1998)]. Overexpression of ATR in muscle cells on iso-chromosome 3q results in a block to differentiation, gives rise to abnormal centrosome numbers and chromosome instability, and abolishes the G1 arrest in response to irradiation [Smith, et al. *Nat. Genetics* 19:39–46 (1998)]. Overexpression of a dominant negative mutant of ATR sensitizes cells to irradiation and cisplatinum [Cliby, et al., supra] and the cells fail to arrest in G2 in response to irradiation. ATR is found associated with chromosomes in meiotic cells where DNA breaks and abnormal DNA structures that persist as a result of the process of meiotic recombination [Keegan, et al, *Genes Dev.* 10:2423–2437 (1996)]. These data suggest that ATR, like ATM, senses DNA damage and effects a cell cycle arrest in order to allow for DNA repair.

FRAP, the target of the potent immunosuppressent rapamycin, has been demonstrated to be involved in the control of translation initiation and progression through the G1 phase of the cell cycle in response to nutrients [Kuruvilla and Shrieber, *Chemistry and Biology* 6:R129–R136 (1999)]. FRAP regulates translation initiation by phosphorylation of the $p70^{S6K}$ protein kinase and the 4E-BP1 translation regulator. While ATM, ATR, and DNA-PK are thought to sense lesions in nucleic acids, FRAP is thought to sense intracellular levels of amino acids pools. In cells lacking proper nutrients that are amino acid starved, uncharged amino acid levels rise. FRAP may sense these uncharged amino acids, become activated, and signal G1 cell cycle arrest [Kuruvilla and Shreiber, supra].

In yeast, Tor1p and Tor2p proteins show significant homology to FRAP. Both Tor1p and Tor2p are sensitive to rapamycin and both are involved in initiation of translation as well as G1 progression in response to nutrient conditions. Tor2p also plays a role in organization of actin cytoskeleton, but this activity is not blocked by rapamycin. These observations suggest that Tor2p stimulates two distinct signal transduction pathways.

An additional PIK-related family member, TRRAP, was recently identified as a member of a protein complex containing the cell cycle regulators, c-myc and E2F-1 [McMahon et al., *Cell* 94:363–374 (1998)]. While TRRAP shows significant sequence homology to the protein kinase domain of the other PIK-related kinases, the protein lacks critical residues required for protein kinase activity. Studies have failed to show protein kinase activity, but others have shown that TRRAP contains a histone acetyltransferase (HAT) activity. Interestingly, overexpression of TRRAP dominant inhibiting mutants or anti-sense constructs of TRRAP blocked oncogenic transformation of cultured cells transformed by c-myc or the viral oncogene, E1A

[McMahon et al., supra]. These results suggest that TRRAP also plays an important role in regulating cell cycle progression and preventing oncogenesis.

In general, the proteins in this family of kinases play important roles in surveillance of DNA and cell cycle progression in order to insure genetic integrity from generation to generation. All cancer cells have a dysfunctional cell cycle and continue through the cell cycle in an inappropriate manner, either by failing to respond to negative growth signals or by failing to die in response to the appropriate signal. In addition, most cancer cells lack genomic integrity and often have an increased chromosome count compared to normal cells. Inhibitors of cell cycle checkpoints or DNA damage repair in combination with the cytotoxic agents may force cancer cells to die by forcing them to continue to progress through the cell cycle in the presence of DNA damaging agents such that they undergo catastrophic events that lead to cell death. Further, inhibitors of cell cycle progression may act to inhibit activation of cells involved in an inflammatory response and therefore inhibit inflammation.

Thus there exists a need in the art to identify additional members of the family of PIK-related kinases, and in particular, those that play roles in regulation of cell cycle progression, cell cycle checkpoints, and DNA damage repair.

BRIEF DESCRIPTION OF THE INVENTION

The present invention provides purified and isolated Atr-2 polypeptides. In one aspect, the Atr-2 polypeptide comprises the amino acid sequence set out in SEQ ID NO:2. The invention also provides mature Atr-2 polypeptides, preferably encoded by a polynucleotide comprising the sequence set out in SEQ ID NO: 1. Atr-2 polypeptides of the invention include those encoded by a polynucleotide selected from the group consisting of: a) the polynucleotide set out in SEQ ID NO: 1; b) a polynucleotide encoding a polypeptide encoded by the polynucleotide of (a), and c) a polynucleotide that hybridizes to the complement of the polynucleotide of (a) or (b) under moderately stringent conditions.

The invention also provides polynucleotides encoding Atr-2 polypeptides. In one aspect, the Atr-2 encoding polynucleotide comprises the sequence set forth in SEQ ID NO: 1. The invention also provides polynucleotides encoding a human Atr-2 polypeptide selected from the group consisting of: a) the polynucleotide set out in SEQ ID NO: 1; b) a polynucleotide encoding a polypeptide encoded by the polynucleotide of (a), and c) a polynucleotide that hybridizes to the complement of the polynucleotide of (a) or (b) under moderately stringent conditions. Polynucleotides of the invention include DNA molecules, cDNA molecules, genomic DNA molecules, as well as wholly or partially chemically synthesized DNA molecule. The invention further provide fragments of polynucleotides of the invention, and preferably fragments of the polynucleotide set out in SEQ ID NO: 1.

Antisense polynucleotides which specifically hybridize with the complement of a polynucleotide of the invention are also provided.

The invention further provides expression constructs comprising a polynucleotide of the invention, as well as host cells transformed or transfected with an expression construct of the invention.

Method for producing an Atr-2 polypeptide are also provided, comprising the steps of: a) growing a transformed or transfected host cell of the invention under conditions appropriate for expression of the Atr-2 polypeptide and b) isolating the Atr-2 polypeptide from the host cell or medium of the host cell's growth.

The invention also provides antibodies specifically immunoreactive with a polypeptide of the invention. Preferably, the antibodies are monoclonal antibodies. Hybridomas which produce the antibodies are also provided, as are anti-idiotype antibodies specifically immunoreactive with an antibody of the invention.

The invention further provides methods to identify a binding partner compound of an Atr-2 polypeptide comprising the steps of: a) contacting the Atr-2 polypeptide with a compound under conditions which permit binding between the compound and the Atr-2 polypeptide; and b) detecting binding of the compound to the Atr-2 polypeptide. Preferably, the binding partner modulates activity of the Atr-2 polypeptide. In one aspect the binding partner inhibits activity of the Atr-2 polypeptide, and in another aspect, binding partner enhances activity of the Atr-2 polypeptide.

The invention also provide methods to identify a binding partner compound of an Atr-2-encoding polynucleotide of the invention steps of: a) contacting the Atr-2-encoding polynucleotide with a compound under conditions which permit binding between the compound and the Atr-2-encoding polynucleotide; and b) detecting binding of the compound to the Atr-2-encoding polynucleotide. Preferably, the specific binding partner modulates expression of an Atr-2 polypeptide encoded by the Atr-2-encoding polynucleotide. In one aspect, the binding partner compound inhibits expression of the Atr-2 polypeptide, while in another aspect, the binding partner compound enhances expression of the Atr-2 polypeptide.

The invention further provides compounds identified by methods of the invention, as well as compositions comprising a compound identified by a method of the invention and a pharmaceutically acceptable carrier.

DETAILED DESCRIPTION OF THE INVENTION

In brief, the present invention provides purified and isolated polynucleotides encoding Atr-2 polypeptides. The invention includes both naturally occurring and non-naturally occurring Atr-2-encoding polynucleotides. Naturally occurring polynucleotides of the invention include distinct gene species within the Atr-2 family, including, for example, allelic and splice variants, as well as species homologs (or orthologs) expressed in cells of other animals. Non-naturally occurring Atr-2 encoding polynucleotides include analogs or variants of the naturally occurring products, such as insertion variants, deletion variants, substitution variants, and derivatives, as described below. In a preferred embodiment, the invention provides a polynucleotide comprising the sequence set forth in SEQ ID NO: 1. The invention also embraces polynucleotides encoding the amino acid sequence set out in SEQ ID NO: 2. A presently preferred polypeptide of the invention comprises the amino acid sequence set out in SEQ ID NO: 2. Anti-sense polynucleotides are also provided.

The invention also provides expression constructs (or vectors) comprising polynucleotides of the invention, and host cells comprising a polynucleotide or an expression construct of the invention. Methods to produce a polypeptide of the invention are also comprehended. The invention further provides antibodies, preferably monoclonal antibodies, specifically immunoreactive with a polypeptide of the invention, as well as hybridomas that secrete the antibodies.

The invention also provides Atr-2 polypeptides encoded by a polynucleotide of the invention. Atr-2 polypeptides include naturally and non-naturally occurring species. The invention further provides binding partner compounds that interact with an Atr-2 polypeptide of the invention. Methods to identify binding partner compounds are also provided, as well as methods to identify modulators of Atr-2 polypeptide biological activity.

The invention also provides materials and methods to regulate expression of Atr-2 including ribozymes, anti-sense polynucleotides, and compounds that form triplet helix.

Gene therapy techniques are also provided to modulate disease states associated with Atr-2 expression and/or biological activity.

The invention also provides compositions, and preferably pharmaceutical compositions, comprising an Atr-2 polypeptide, an Atr-2 antibody, a modulator of Atr-2 expression or biological activity, or a combination of these compounds. When compositions of the invention, and in particulary pharmaceutical compositions, are used for therapeutic or prophylactic intervention, the compounds can include one or more pharmaceutically acceptable carriers. Methods of packaging a composition of the invention, as well as methods for delivery and therapeutic treatment are also provided.

In one aspect, the invention provides novel purified and isolated human polynucleotides (e.g., DNA sequences and RNA transcripts, both sense and complementary anti-sense strands, including splice variants thereof) encoding the human Atr-2 polypeptides. DNA sequences of the invention include genomic and cDNA sequences as well as wholly or partially chemically synthesized DNA sequences. Genomic DNA of the invention comprises the protein coding region for a polypeptide of the invention and includes allelic variants of the preferred polynucleotide of the invention. Genomic DNA of the invention is distinguishable from genomic DNAs encoding polypeptides other than Atr-2 in that it includes the Atr-2 protein coding region found in Atr-2-encoding cDNA of the invention. Genomic DNA of the invention can be transcribed into RNA, and the resulting RNA transcript may undergo one or more splicing events wherein one or more introns (i.e., non-coding regions) of the transcript are removed, or "spliced out." "Peptide nucleic acids (PNAs)" [Corey, *TIBTech* 15:224–229 (1997)] encoding a polypeptide of the invention are also contemplated. PNAs are DNA analogs containing neutral amide backbone linkages that are resistant to DNA degradation enzymes and which bind to complementary sequences at higher affinity than analogous DNA sequences as a result of the neutral charge on the backbone of the molecule. RNA transcripts that can be spliced by alternative mechanisms, and therefore be subject to removal of different RNA sequences but still encode an Atr-2 polypeptide, are referred to in the art as splice variants which are embraced by the invention. Splice variants comprehended by the invention therefore are encoded by the same DNA sequences but arise from distinct mRNA transcripts. Allelic variants are known in the art to be modified forms of a wild type gene sequence, the modification resulting from recombination during chromosomal segregation or exposure to conditions which give rise to genetic mutation. Allelic variants, like wild type genes, are inherently naturally occurring sequences (as opposed to non-naturally occurring variants which arise from in vitro manipulation).

The invention also comprehends cDNA that is obtained through reverse transcription of an RNA polynucleotide encoding Atr-2, followed by second strand synthesis of a complementary strand to provide a double stranded DNA.

"Chemically synthesized" as used herein and understood in the art, refers to polynucleotides produced by purely chemical, as opposed to enzymatic, methods. "Wholly" chemically synthesized DNA sequences are therefore produced entirely by chemical means, and "partially" synthesized DNAs embrace those wherein only portions of the resulting DNA were produced by chemical means.

A preferred DNA sequence encoding a human Atr-2 polypeptide is set out in SEQ ID NO: 1. The worker of skill in the art will readily appreciate that the preferred DNA of the invention comprises a double stranded molecule, for example, the molecule having the sequence set forth in SEQ ID NO: 1 along with the complementary molecule (the "non-coding strand" or "complement") having a sequence deducible from the sequence of SEQ ID NO: 1 according to Watson-Crick base pairing rules for DNA. In addition, single stranded polynucleotides, including RNA as well as coding and noncoding DNAs, are also embraced the invention. Also preferred are polynucleotides encoding the Atr-2 polypeptide of SEQ ID NO: 2.

The invention further embraces species, preferably mammalian, homologs of the human Atr-2 DNA. Species homologs (also known in the art as orthologs), in general, share at least 35%, at least 40%, at least 45%, at least 50%, at least 60%, at least 65%, at least 70%, at least 75%, at least 80%, at least 85%, at least 90%, at least 95%, at least 98%, or at least 99% homology with a human DNA of the invention. Percent sequence "homology" with respect to polynucleotides of the invention is defined herein as the percentage of nucleotide bases in the candidate sequence that are identical to nucleotides in the Atr-2 sequence after aligning the sequences and introducing gaps, if necessary, to achieve the maximum percent sequence identity as discussed below.

The polynucleotide sequence information provided by the invention makes possible large scale expression of the encoded Atr-2 polypeptide by techniques well known and routinely practiced in the art. Polynucleotides of the invention also permit identification and isolation of polynucleotides encoding related Atr-2 polypeptides by well known techniques including Southern and/or Northern hybridization, polymerase chain reaction (PCR), and variations of PCR. Examples of related polynucleotides include human and non-human genomic sequences, including allelic variants, as well as polynucleotides encoding polypeptides homologous to Atr-2 and structurally related polypeptides sharing one or more biological, immunological, and/or physical properties of Atr-2.

The disclosure of a full length polynucleotide encoding an Atr-2 polypeptide makes readily available to the worker of ordinary skill in the art every possible fragment of the full length polynucleotide. The invention therefore provides fragments of Atr-2-encoding polynucleotides comprising at least 10 to 20, and preferably at least 15, consecutive nucleotides of a polynucleotide encoding Atr-2, however, the invention comprehends fragments of various lengths. Preferably, fragment polynucleotides of the invention comprise sequences unique to the Atr-2-encoding polynucleotide, and therefore hybridize under highly stringent or moderately stringent conditions only (i.e., "specifically" or "exclusively") to polynucleotides encoding Atr-2, or Atr-2 fragments thereof, containing the unique sequence. Polynucleotide fragments of genomic sequences of the invention comprise not only sequences unique to the coding region, but also include fragments of the full length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases.

The invention also provides fragment polynucleotides that are conserved in one or more polynucleotides encoding members of the Atr-2 family of polypeptides. Such fragments include sequences characteristic of the family of Atr-2 polynucleotides, and are also referred to as "signature sequences." The conserved signature sequences are readily discernable following simple sequence comparison of polynucleotides encoding members of the Atr-2 family. Fragments of the invention can be labeled in a manner that permits their detection, including radioactive and non-radioactive labeling.

Fragment polynucleotides are particularly useful as probes for detection of full length or other fragment Atr-2 polynucleotides. One or more fragment polynucleotides can be included in kits that are used to detect the presence of a polynucleotide encoding Atr-2, or used to detect variations in a polynucleotide sequence encoding Atr-2, including polymorphisms, and particularly single nucleotide polymorphisms. Kits of the invention optionally include a container and/or a label.

The invention also embraces naturally or non-naturally occurring Atr-2-encoding polynucleotides that are fused, or ligated, to a heterologous polynucleotide to encode a fusion (or chimeric) protein comprising all or part of an Atr-2 polypeptide. "Heterologous" polynucleotides include sequences that are not found adjacent, or as part of, Atr-2-encoding sequences in nature. The heterologous polynucleotide sequence can be separated from the Atr-2-coding sequence by an encoded cleavage site that will permit removal of non-Atr-2 polypeptide sequences from the expressed fusion protein. Heterologous polynucleotide sequences can include those encoding epitopes, such as poly-histidine sequences, FLAG® tags, glutathione-S-transferase, thioredoxin, and/or maltose binding protein domains, that facilitate purification of the fusion protein; those encoding domains, such as leucine zipper motifs, that promote multimer formation between the fusion protein and itself or other proteins; and those encoding immunoglobulins or fragments thereof that can enhance circulatory half-life of the encoded protein.

The invention also embraces DNA sequences encoding Atr-2 species that hybridize under highly or moderately stringent conditions to the non-coding strand, or complement, of the polynucleotide in SEQ ID NO: 1. Atr-2-encoding polynucleotides of the invention include a) the polynucleotide set out in SEQ ID NO: 2; b) polynucleotides encoding a polypeptide encoded by the polynucleotide of (a), and c) polynucleotides that hybridize to the complement of the polynucleotides of (a) or (b) under moderately or highly stringent conditions. Exemplary high stringency conditions include a final wash in 0.2×SSC/0.1% SDS at 65° C. to 75° C., and exemplary moderate stringency conditions include a final wash at 2× to 3×SSC/0.1% SDS at 65° C. to 75° C. It is understood in the art that conditions of equivalent stringency can be achieved through variation of temperature and buffer, or salt concentration as described in Ausubel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

Autonomously replicating recombinant expression constructs such as plasmid and viral DNA vectors incorporating Atr-2-encoding sequences are also provided. Expression constructs wherein Atr-2-encoding polynucleotides are operatively linked to an endogenous or exogenous expression control DNA sequence and a transcription terminator are also provided. Expression control DNA sequences include promoters, enhancers, and/or operators, and are generally selected based on the expression systems in which the expression construct is to be utilized. Preferred promoter and enhancer sequences are generally selected for the ability to increase gene expression, while operator sequences are generally selected for the ability to regulate gene expression. It is understood in the art that the choice of host cell is relevant to selection of an appropriate regulatory sequence. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell.

Expression constructs are preferably utilized for production of an encoded protein, but may also be utilized to amplify the construct itself when other amplification techniques are impractical.

According to another aspect of the invention, host cells are provided, including prokaryotic and eukaryotic cells, comprising a polynucleotide of the invention in a manner which permits expression of the encoded Atr-2 polypeptide. Polynucleotides of the invention may be introduced into the host cell as part of a circular plasmid, or as linear DNA comprising an isolated protein coding region or a viral vector. Methods for introducing DNA into the host cell well known and routinely practiced in the art include transformation, transfection, electroporation, nuclear injection, or fusion with carriers such as liposomes, micelles, ghost cells, protoplasts, and other transformed cells. Expression systems of the invention include bacterial, yeast, fungal, plant, insect, invertebrate, and mammalian cells systems.

Host cells of the invention are a valuable source of immunogen for development of antibodies specifically, i.e., exclusively, immunoreactive with Atr-2. Host cells of the invention are also useful in methods for large scale production of Atr-2 polypeptides wherein the cells are grown in a suitable culture medium and the desired polypeptide products are isolated from the cells or from the medium in which the cells are grown by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those wherein the desired protein is expressed and purified as a fusion protein having a specific tag, label, or chelating moiety that is recognized by a specific binding partner or agent. The purified protein can be cleaved to yield the desired protein, or be left as an intact fusion protein. Cleavage of the fusion component may produce a form of the desired protein having additional amino acid residues as a result of the cleavage process.

Knowledge of Atr-2-encoding DNA sequences allows for modification of cells to permit, or increase, expression of endogenous Atr-2. Cells can be modified (e.g., by homologous recombination) to provide increased Atr-2 expression by replacing, in whole or in part, the naturally occurring Atr-2 promoter with all or part of a heterologous promoter so that the cells express Atr-2 at higher levels. The heterologous promoter is inserted in such a manner that it is operatively linked to Atr-2-encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the Atr-2 coding sequence, amplification of the marker DNA by standard selection methods results in co-amplification of the Atr-2 coding sequences in the cells.

The DNA sequence information provided by the present invention also makes possible the development through, e.g. homologous recombination or "knock-out" strategies [Capecchi, *Science* 244:1288–1292 (1989)], of animals that fail to express functional Atr-2 or that express a variant of Atr-2. Such animals are useful as models for studying the in vivo activities of Atr-2 and modulators of Atr-2.

The invention also provides purified and isolated mammalian Atr-2 polypeptides encoded by a polynucleotide of the invention. Presently preferred is a human Atr-2 polypeptide comprising the amino acid sequence set out in SEQ ID NO: 2. Mature Atr-2 polypeptides are also provided, wherein leader and/or signal sequences are removed. The invention also embraces Atr-2 polypeptides encoded by a DNA selected from the group consisting of: a) the polynucleotide set out in SEQ ID NO: 1; b) polynucleotides encoding a polypeptide encoded by the polynucleotide of (a), and c) polynucleotides that hybridize to the complement of the polynucleotides of (a) or (b) under moderate or high stringency conditions.

The invention also embraces polypeptides have at least 99%, at least 95%, at least 90%, at least 85%, at least 80%, at least 75%, at least 70%, at least 65%, at least 60%, at least 55% or at least 50% identity and/or homology to the preferred polypeptide of the invention. Percent amino acid sequence "identity" with respect to the preferred polypeptide of the invention is defined herein as the percentage of amino acid residues in the candidate sequence that are identical with the residues in the Atr-2 sequence after aligning both sequences and introducing gaps, if necessary, to achieve the maximum percent sequence identity, and not considering any conservative substitutions as part of the sequence identity. Percent sequence "homology" with respect to the preferred polypeptide of the invention is defined herein as the percentage of amino acid residues in the candidate sequence that are identical with the residues in the Atr-2 sequence after aligning the sequences and introducing gaps, if necessary, to achieve the maximum percent sequence identity, and also considering any conservative substitutions as part of the sequence identity.

In one aspect, percent homology is calculated as the percentage of amino acid residues in the smaller of two sequences which align with identical amino acid residue in the sequence being compared, when four gaps in a length of 100 amino acids are introduced to maximize alignment [Dayhoff, in *Atlas of Protein Sequence and Structure*, Vol. 5, p. 124, National Biochemical Research Foundation, Washington, D.C. (1972), incorporated herein by reference].

Preferred methods to determine identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux, J., et al., Nucleic Acids Research 12(1):387 (1984); Genetics Computer Group, University of Wisconsin, Madison, Wis.), BLASTP, BLASTN, and FASTA (Atschul, S. F. et al., J. Molec. Biol. 215:403–410 (1990). The BLAST X program is publicly available from the National Center for Biotechnology Information (NCBI) and other sources (BLAST Manual, Altschul, S., et al. NCB NLM NIH Bethesda, Md. 20894; Altschul, S., et al., J. Mol. Biol. 215:403–410 (1990). The well known Smith Waterman algorithm may also be used to determine identity.

By way of example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually ⅟₁₀ times the gap opening penalty), as well as a comparison matrix such as PAM 250 or BLOSUM 62 are used in conjunction with the algorithm. A standard comparison matrix (see Dayhoff et al., in: Atlas of Protein Sequence and Structure, vol. 5, supp.3 [1978] for the PAM250 comparison matrix; see Henikoff et al., Proc. Natl. Acad. Sci USA, 89:10915–10919 [1992] for the BLOSUM 62 comparison matrix) is also used by the algorithm.

Preferred parameters for polypeptide sequence comparison include the following:

Algorithm: Needleman and Wunsch, *J. Mol. Biol.* 48:443–453 (1970), Comparison matrix: BLOSUM 62 from Henikoff and Henikoff, *Proc. Natl. Acad. Sci. USA* 89:10915–10919 (1992).

Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:

Algorithm: Needleman and Wunsch, J. Mol Biol. 48:443–453 (1970)
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will depend on the specific comparison to be made, such as DNA to DNA, protein to protein, protein to DNA; and additionally, whether the comparison is between pairs of sequences (in which case GAP or BestFit are generally preferred) or between one sequence and a large database of sequences (in which case FASTA or BLASTA are preferred).

Certain alignment schemes for aligning two amino acid sequences may result in matching of only a short region of the two sequences, and this small aligned region may have very high sequence identity even though there is no significant relationship between the two full length sequences. Accordingly, in a preferred embodiment, the selected alignment method will result in an alignment that spans at least about 66 contiguous amino acids of the claimed full length polypeptide.

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated form of Atr-2 polypeptides are embraced.

The invention also embraces variant (or analog) Atr-2 polypeptides.

In one example, insertion variants are provided wherein one or more amino acid residues supplement an Atr-2 amino acid sequence. Insertions may be located at either or both termini of the protein, or may be positioned within internal regions of the Atr-2 amino acid sequence. Insertional variants with additional residues at either or both termini can include for example, fusion proteins and proteins including amino acid tags or labels. Insertion variants include Atr-2 polypeptides wherein one or more amino acid residues are added to a fragment of an Atr-2 amino acid sequence. Variant products of the invention also include mature Atr-2 products, i.e., Atr-2 polypeptide products wherein leader or signal sequences are removed, and additional amino terminal residues have been inserted. The additional amino terminal residues may be derived from another protein, or may include one or more residues that are not identifiable as being derived from a specific protein. Atr-2 products with an additional methionine residue at position −1 (Met$^{-1}$-Atr-2) are contemplated as are Atr-2 products with additional methionine and lysine residues at positions −2 and −1 (Met$^{-2}$-Lys$^{-1}$-Atr-2). Variants of Atr-2 with additional Met, Met-Lys, Lys residues (or one or more basic residues in general) are particularly useful for enhanced recombinant protein production in bacterial host cell. Heterologous amino acid sequences can also include protein transduction domains that target the lipid bilayer of a cell membrane and permit protein transduction into cells in an indiscriminate manner [Schwarze, et al., *Science* 285.:1569–1572 (1999)]. Fusion polypeptides of this type are particularly well suited for delivery to the cytoplasm and nucleus of cells, and also to cells across the blood-barrier.

The invention also embraces Atr-2 variants having additional amino acid residues which result from use of specific expression systems. For example, use of commercially available vectors that express a desired polypeptide as part of glutathione-S-transferase (GST) fusion product provides the desired polypeptide having an additional glycine residue at position −1 after cleavage of the GST component from the desired polypeptide. Variants which result from expression in other vector systems are also contemplated.

Insertional variants also include fusion proteins wherein the amino and/or carboxy termini of the Atr-2-polypeptide is fused to another polypeptide. Examples of other polypeptides are immunogenic polypeptides, proteins with long circulating half life such as immunoglobulin constant regions, marker proteins (e.g., fluorescent, chemiluminescence, enzymes, and the like) proteins or polypeptide that facilitate purification of the desired Atr-2 polypeptide, and polypeptide sequences that promote formation of multimeric proteins (such as leucine zipper motifs that are useful in dimer formation/stability). Fusion proteins wherein an Atr-2 polypeptide is conjugated to a hapten or other agent to improve, i.e., enhance, immungenicity, are also provided.

In another aspect, the invention provides deletion variants wherein one or more amino acid residues in an Atr-2 polypeptide are removed. Deletions can be effected at one or both termini of the Atr-2 polypeptide, or with removal of one or more residues within the Atr-2 amino acid sequence. Deletion variants, therefore, include all fragments of an Atr-2 polypeptide. Disclosure of the complete Atr-2 amino acid sequences necessarily makes available to the worker of ordinary skill in the art every possible fragment of the Atr-2 polypeptide.

The invention also embraces polypeptide fragments of the sequence set out in SEQ ID NO: 2 wherein the fragments maintain biological, immunological, physical, and/or chemical properties of an Atr-2 polypeptide. Fragments comprising at least 5, 10, 15, 20, 25, 30, 35, or 40 consecutive amino acids of SEQ ID NO: 2 are comprehended by the invention. Preferred polypeptide fragments display antigenic and/or biological properties unique to or specific for the Atr-2 family of polypeptides. Fragments of the invention having the desired biological and immunological properties can be prepared by any of the methods well known and routinely practiced in the art.

In still another aspect, the invention provides substitution variants of Atr-2 polypeptides. Particularly preferred variants include dominant negative mutants that lack kinase activity. Substitution variants include those polypeptides wherein one or more amino acid residues of an Atr-2 polypeptide are removed and replaced with alternative residues. In one aspect, the substitutions are conservative in nature, however, the invention embraces substitutions that are also non-conservative. Conservative substitutions for this purpose may be defined as set out in Tables A, B, or C below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A (from WO 97/09433, page 10, published Mar. 13, 1997 (PCT/GB96/02197, filed Sep. 6, 1996), immediately below, wherein amino acids are listed by standard one letter designations.

TABLE I

Conservative Substitutions I

| SIDE CHAIN CHARACTERISTIC | AMINO ACID |
|---|---|
| Aliphatic | |
|   Non-polar | G A P I L V |
|   Polar—uncharged | C S T M N Q |
|   Polar—charged | D E K R |
| Aromatic | H F W Y |
| Other | N Q D E |

Alternatively, conservative amino acids can be grouped as described in Lehninger, [*Biochemistry*, Second Edition; Worth Publishers, Inc. NY:N.Y. (1975), pp.71–77] as set out in Table B, immediately below.

TABLE B

Conservative Substitutions II

| SIDE CHAIN CHARACTERISTIC | AMINO ACID |
|---|---|
| Non-polar(hydrophobic) | |
|   A. Aliphatic: | A L I V P |
|   B. Aromatic: | F W |
|   C. Sulfur-containing: | M |
|   D. Borderline: | G |
| Uncharged-polar | |
|   A. Hydroxyl: | S T Y |
|   B. Amides: | N Q |
|   C. Sulfhydryl: | C |
|   D. Borderline: | G |
| Positively Charged (Basic): | K R H |
| Negatively Charged (Acidic): | D E |

As still an another alternative, exemplary conservative substitutions are set out in Table C, immediately below.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |

TABLE C-continued

Conservative Substitutions III

| Original Residue | Exemplary Substitution |
|---|---|
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

The invention also provides derivatives of Atr-2 polypeptides. Derivatives include Atr-2 polypeptides bearing modifications other than insertion, deletion, or substitution of amino acid residues. Preferably, the modifications are covalent in nature, and include for example, chemical bonding with polymers, lipids, other organic, and inorganic moieties. Derivatives of the invention may be prepared to increase circulating half-life of a Atr-2 polypeptide, to improve targeting capacity for the polypeptide to desired cells, tissues, or organs, and/or to modulate (increase or decrease) biological and/or immunological activity.

The invention further embraces Atr-2 products covalently modified or derivatized to include one or more water soluble polymer attachments such as polyethylene glycol, polyoxyethylene glycol, polypropylene glycol or any of the many other polymers well known in the art, including, for example, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are Atr-2 products covalently modified with polyethylene glycol (PEG) subunits. Water soluble polymers may be bonded at specific positions, for example at the amino terminus of the Atr-2 products, or randomly attached to one or more side chains of one or more amino acid residues in the polypeptide.

The invention further comprehends Atr-2 polypeptides having combinations of insertions, deletions, substitutions, or derivatizations.

Also comprehended by the present invention are antibodies (e.g., monoclonal and polyclonal antibodies, single chain antibodies, chimeric antibodies, bifunctional/bispecific antibodies, humanized antibodies, human antibodies, bispecific antibodies, and complementary determining region (CDR)-grafted antibodies/proteins, including compounds which include CDR and/or antigen-binding sequences, which specifically recognize a polypeptide of the invention) and other binding proteins specific for Atr-2 products or fragments thereof. Preferred antibodies of the invention are human antibodies which are produced and identified according to methods described in WO93/11236, published Jun. 20, 1993, which is incorporated herein by reference in its entirety. Antibody fragments, including Fab, Fab', F(ab')$_2$, and Fv, are also provided by the invention. The term "specific for" indicates that the variable regions of the antibodies of the invention recognize and bind Atr-2 polypeptides exclusively (i.e., able to distinguish Atr-2 polypeptides from the family of ATR polypeptides despite sequence identity, homology, or similarity found in the family of polypeptides), but may also interact with other proteins (for example, S. aureus protein A or other antibodies in ELISA techniques) through interactions with sequences outside the variable or CDR regions of the antibodies, and in particular, in the constant region of the molecule. Screening assays to determine binding specificity or exclusivity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the Atr-2 polypeptides of the invention are also contemplated, provided that the antibodies are first and foremost specific or exclusive for, as defined above, Atr-2 polypeptides. As with antibodies that are specific for full length Atr-2 polypeptides, antibodies of the invention that recognize Atr-2 fragments are those which can distinguish Atr-2 polypeptides from the family of ATR polypeptides despite inherent sequence identity, homology, or similarity found in the family of proteins.

Antibodies of the invention can be produced using any method well known and routinely practiced in the art, using any polypeptide, or immunogenic fragment thereof, of the invention. Immunogenic polypeptides can be isolated from natural sources, from recombinant host cells, or can be chemically synthesized. Protein of the invention may also be conjugated to a hapten such as keyhole limpet hemocyanin (KLH) in order to increase immunogenicity. Methods for synthesizing such peptides are known in the art, for example, as in R. P. Merrifield, J. Amer. Chem. Soc. 85: 2149–2154 (1963); J. L. Krstenansky, et al., FEBS Lett. 211:10 (1987). Antibodies to a polypeptide of the invention can also be prepared through immunization using a polynucleotide of the invention, as described in Fan et al., Nat. Biotech. 17:870–872 (1999). DNA encoding a polypeptide may be used to generate antibodies against the encoded polypetide following topical administration of naked plasmid DNA or following injection, and preferably intramuscular injection, or the DNA.

Non-human antibodies may be humanized by any methods known in the art. In one method, the non-human CDRs are inserted into a human antibody or consensus antibody framework sequence. Further changes can then be introduced into the antibody framework to modulate affinity or immunogenicity.

Antibodies of the invention further include plastic antibodies or molecularly imprinted polymers (MIPs) [Haupt and Mosbauch, TIBTech 16:468–475) (1998)]. Antibodies of this type are particularly useful in immunoaffinity separation, chromatography, soli phase extraction, immunoassays, for use as immunosensors, and for screening chemical or biological libraries. A typical method of preparation is described in Haupt and Mosbauch [supra]. Advatanges of antibodies of this type are that no animal immunization is required, the antibodies are relatively inexpensive to produce, they are resistant to organic solvents, and they are reusable over long period of time.

Antibodies of the invention can also include one or more labels that permit detection of the antibody, and in particular, antibody binding. Labels can include, for example, radioactivity, fluorescence (or chemiluminescence), one of a high affinity binding pair (e.g.,biotin/avidin), enzymes, or combinations of one or more of these labels.

Antibodies of the invention are useful for, for example, therapeutic purposes (by modulating activity of Atr-2), diagnostic purposes to detect or quantitate Atr-2, as well as purification of Atr-2. Kits comprising an antibody of the invention for any of the purposes described herein are also comprehended. In general, a kit of the invention also includes a control antigen for which the antibody is immunospecific. Kits of the invention optionally include a container and/or a label.

The DNA and amino acid sequence information provided by the present invention also makes possible the systematic analysis of the structure and function of Atr-2. DNA and amino acid sequence information for Atr-2 also permits identification of binding partner compounds with which an Atr-2 polypeptide or polynucleotide will interact. Methods to identify binding partner compounds include solution assays, in vitro assays wherein Atr-2 polypeptides are immobilized, and cell based assays. Identification of binding partner compounds of Atr-2 polypeptides provides potential targets for therapeutic or prophylactic intervention in pathologies associated with Atr-2 biological activity.

Specific binding proteins can be identified or developed using isolated or recombinant Atr-2 products, Atr-2 variants or analogs, or cells expressing such products. Binding proteins are useful for purifying Atr-2 products and detection or quantification of Atr-2 products in fluid and tissue samples using known immunological procedures. Binding proteins are also manifestly useful in modulating (i. e., blocking, inhibiting, or stimulating) biological activities of Atr-2, especially those activities involved in signal transduction or biological pathways in general wherein Atr-2 participates directly or indirectly.

In solution assays, methods of the invention comprise the steps of (a) contacting an Atr-2 polypeptide with one or more candidate binding partner compounds and (b) identifying the compounds that bind to the Atr-2 polypeptide. Identification of the compounds that bind the Atr-2 polypeptide can be achieved by isolating the Atr-2 polypeptide/binding partner complex, and separating the Atr-2 polypeptide from the binding partner compound. An additional step of characterizing the physical, biological, and/or biochemical properties of the binding partner compound is also comprehended in another embodiment of the invention. In one aspect, the Atr-2 polypeptide/binding partner complex is isolated using a antibody immunospecific for either the Atr-2 polypeptide or the candidate binding partner compound. In another aspect, the complex is isolated using a second binding partner compound that interacts with either the Atr-2 polypeptide or the candidate binding partner compound.

In still another embodiment, either the polypeptide Atr-2 or the candidate binding partner compound comprises a label or tag that facilitates its isolation, and methods of the invention to identify binding partner compounds include a step of isolating the Atr-2 polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), thioredoxin, and/or maltose binding protein, each of which is well known and routinely used in the art and are embraced by the invention.

In an in vitro assay, methods of the invention comprise the steps of (a) contacting an immobilized Atr-2 polypeptide with a candidate binding partner compound and (b) detecting binding of the candidate compound to the Atr-2 polypeptide. In an alternative embodiment, the candidate binding partner compound is immobilized and binding of the Atr-2 polypeptide is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin or streptavidin moiety. Detection of binding can be accomplished (i) using a radioactive label on the compound that is not immobilized, (ii) using of a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

In cell based assays of the invention to identify binding partner compounds of an Atr-2 polypeptide, methods comprise the steps of contacting an Atr-2 polypeptide in a cell with a candidate binding partner compound and detecting binding of the candidate binding partner compound to the Atr-2 polypeptide. A presently preferred method uses the dihybrid assay as previously described [Fields and Song, *Nature* 340:245–246(1989); Fields, *Methods: A Companion to Methods in Enzymology* 5:116–124 (1993); U.S. Pat. No. 5,283,173 issued Feb. 1, 1994 to Fields, et al.]. Modifications and variations on the di-hybrid assay (also referred to in the art as "two-hybrid" assay) have previously been described [Colas and Brent, *TIBTECH* 16:355–363 (1998)] and are embraced by the invention.

Agents that modulate (i.e., increase, decrease, or block) Atr-2 activity or expression may be identified by incubating a putative modulator with an Atr-2 polypeptide or polynucleotide and determining the effect of the putative modulator on Atr-2 activity or expression. The selectivity, or specificity, of a compound that modulates the activity of Atr-2 can be evaluated by comparing its effects on Atr-2 or an Atr-2-encoding polynucleotide to its effect on other compounds. Cell based methods, such as di-hybrid assays to identify DNAs encoding binding compounds and split hybrid assays to identify inhibitors of Atr-2 polypeptide interaction with a known binding polypeptide, as well as in vitro methods, including assays wherein an Atr-2 polypeptide, Atr-2-encoding polynucleotide, or a binding partner are immobilized, and solution assays are contemplated by the invention.

Selective modulators may include, for example, antibodies and other proteins or peptides which specifically bind to an Atr-2 polypeptide or an Atr-2-encoding nucleic acid, oligonucleotides which bind to an Atr-2 polypeptide or an Atr-2 gene sequence, and other non-peptide compounds (e.g., isolated or synthetic organic and inorganic molecules) which specifically react with an Atr-2 polypeptide or underlying nucleic acid. Preferably, modulators of the invention will bind specifically or exclusively to an Atr-2 polypeptide or Atr-2-encoding polynucleotide, however, modulators that bind an Atr-2 polypeptide or an Atr-2-encoding polynucleotide with higher affinity or avidity compared to other compounds are also contemplated. Mutant Atr-2 polypeptides which affect the enzymatic activity or cellular localization of the wild-type Atr-2 polypeptides are also contemplated by the invention. Presently preferred targets for the development of selective modulators include, for example: (1) regions of an Atr-2 polypeptide which contact other proteins, (2) regions that localize an Atr-2 polypeptide within a cell, (3) regions of an Atr-2 polypeptide which bind substrate, (4) allosteric regulatory binding site(s) of an Atr-2 polypeptide, (5) phosphorylation site(s) of an Atr-2 polypeptide as well as other regions of the protein wherein covalent modification regulates biological activity and (6) regions of an Atr-2 polypeptide which are involved in multimerization of subunits. Still other selective modulators include those that recognize specific Atr-2-encoding and regulatory polynucleotide sequences. Modulators of Atr-2 activity may be therapeutically useful in treatment of diseases and physiological conditions in which Atr-2 activity is known or suspected to be involved.

Methods of the invention to identify modulators include variations on any of the methods described above to identify binding partner compounds, the variations including techniques wherein a binding partner compound has been identified and the binding assay is carried out in the presence and absence of a candidate modulator. A modulator is identified in those instances where the level of binding between an Atr-2 polypeptide and a binding partner compound changes in the presence of the candidate modulator compared to the level of binding in the absence of the candidate modulator compound. A modulator that increases binding between an Atr-2 polypeptide and the binding partner compound is described as an enhancer or activator, and a modulator that decreases binding between the Atr-2 polypeptide and the binding partner compound is described as an inhibitor. In vitro methods of the invention are particularly amenable to high throughput assays as described below.

In addition to the assays described above which can be modified to identify binding partner compounds, other methods are contemplated which as designed to more specifically identify modulators. In one aspect, methods of the invention comprehend use of the split hybrid assay as generally described in WO98/13502, published Apr. 2, 1998. The invention also embraces variations on this method as described in WO95/20652, published Aug. 3, 1995.

The invention also comprehends high throughput screening (HTS) assays to identify compounds that interact with or inhibit biological activity (i.e., inhibit enzymatic activity, binding activity, etc.) of an Atr-2 polypeptide. HTS assays permit screening of large numbers of compounds in an efficient manner. Cell-based HTS systems are contemplated, including melanophore assays to investigate receptor-ligand interaction, yeast-based assay systems, and mammalian cell expression systems [Jayawickreme and Kost, *Curr. Opin. Biotechnol.* 8:629–634 (1997)]. Automated (robotic) and miniaturized HTS assays are also embraced [Houston and Banks, *Curr. Opin. Biotechnol.* 8:734–740 (1997)]. HTS assays are designed to identify "hits" or "lead compounds" having the desired property, from which modifications can be designed to improve the desired property. Chemical modification of the "hit" or "lead compound" is often based on an identifiable structure/activity relationship (SAR) between the "hit" and the Atr-2 polypeptide.

There are a number of different libraries used for the identification of small molecule modulators, including, (1) chemical libraries, (2) natural product libraries, and (3) combinatorial libraries comprised of random peptides, oligonucleotides or organic molecules.

Chemical libraries consist of structural analogs of known compounds or compounds that are identified as "hits" or "leads" via natural product screening. Natural product libraries are collections from microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) variants thereof. For a review, see *Science* 282:63–68 (1998). Combinatorial libraries are composed of large numbers of peptides, oligonucleotides or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707 (1997).

Identification of modulators through use of the various libraries described herein permits modification of the candidate "hit" (or "lead") to optimize the capacity of the "hit" to modulate activity.

Also made available by the invention are anti-sense polynucleotides which recognize and hybridize to polynucleotides encoding Atr-2. Full length and fragment anti-sense polynucleotides are provided. The worker of ordinary skill will appreciate that fragment anti-sense molecules of the invention include (i) those which specifically or exclusively recognize and hybridize to Atr-2-encoding RNA (as determined by sequence comparison of DNA encoding Atr-2 to DNA encoding other molecules) as well as (ii) those which recognize and hybridize to RNA encoding variants of the Atr-2 family of proteins. Antisense polynucleotides that hybridize to RNA encoding other members of the ATR family of proteins are also identifiable through sequence comparison to identify characteristic, or signature, sequences for the family of molecules. Identification of sequences unique to Atr-2-encoding polynucleotides, as well as sequences common to the family of ATR-encoding polynucleotides, can be easily deduced through use of any publicly available sequence database, or through use of commercially available sequence comparison programs. After identification of the desired sequences, isolation through restriction digestion or amplification using any of the various polymerase chain reaction techniques well known in the art can be performed. Anti-sense polynucleotides are particularly relevant for regulating expression of Atr-2 by those cells expressing Atr-2 mRNA. Antisense molecules are generally from about 5 to about 100 nucleotide in length, and preferably are about 10 to 20 nucleotides in length. Antisense nucleic acids capable of specifically binding to Atr-2 expression control sequences or Atr-2 RNA are introduced into cells, e.g., by a viral vector or colloidal dispersion system such as a liposome.

The anti-sense nucleic acid binds to the Atr-2-encoding target nucleotide sequence in the cell and prevents transcription or translation of the target sequence. Phosphorothioate and methylphosphonate anti-sense oligonucleotides are specifically contemplated for therapeutic use by the invention. The anti-sense oligonucleotides may be further modified by poly-L-lysine, transferrin polylysine, or cholesterol moieties at their 5' end.

The invention further contemplates methods to modulate Atr-2 expression through use of ribozymes. For a review, see Gibson and Shillitoe, *Mol. Biotech.* 7:125–137 (1997). Ribozyme technology can be utilized to inhibit translation of Atr-2 mRNA in a sequence specific manner through (i) the hybridization of a complementary RNA to a target mRNA and (ii) cleavage of the hybridized mRNA through nuclease activity inherent to the complementary strand. Ribozymes can identified by empirical methods but more preferably are specifically designed based on accessible sites on the target mRNA [Bramlage, et al., *Trends in Biotech* 16:434–438 (1998)]. Delivery of ribozymes to target cells can be accomplished using either exogenous or endogenous delivery techniques well known and routinely practiced in the art. Exogenous delivery methods can include use of targeting liposomes or direct local injection. Endogenous methods include use of viral vectors and non-viral plasmids.

Ribozymes can specifically modulate expression of Atr-2 when designed to be complementary to regions unique to a polynucleotide encoding Atr-2. "Specifically modulate" is intended to mean that ribozymes of the invention recognize only (i. e., exclusively) a polynucleotide encoding Atr-2. Similarly, ribozymes can be designed to modulate expression of all or some of the ATR family of proteins. Ribozymes of this type are designed to recognize polynucleotide sequences conserved in all or some of the polynucleotides which encode the family of Atr-2 proteins. Preferred ribozymes bind to an Atr-2-encoding polynucleotide with a higher degree of specificity that to other polynucleotides.

The invention further embraces methods to modulate transcription of Atr-2 through use of oligonucleotide-directed triple helix formation. For a review, see Lavrovsky, et al., *Biochem. Mol. Med.* 62:11–22 (1997). Triple helix formation is accomplished using sequence specific oligonucleotides which hybridize to double stranded DNA in the major groove as defined in the Watson-Crick model. Hybridization of a sequence specific oligonucleotide can thereafter modulate activity of DNA-binding proteins, including, for example, transcription factors and polymerases. Preferred target sequences for hybridization include promoter and enhancer regions to permit transcriptional regulation of Atr-2 expression. In addition to use of oligonucleotides, triple helix formation techniques of the invention also embrace use of peptide nucleic acids as described in Corey, *TIBTECH* 15:224–229 (1997). Oligonucleotides which are capable of triple helix formation are also useful for site-specific covalent modification of target DNA sequences. Oligonucleotides useful for covalent modification are coupled to various DNA damaging agents as described in Lavrovsky, et al. [supra].

Mutations in the Atr-2 gene can result in loss of normal function of the Atr-2 gene product and underlie Atr-2-related human disease states. The invention therefore comprehends gene therapy to restore Atr-2 activity in treating those disease states described herein. Delivery of a functional Atr-2 gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature,* supplement to vol. 392, no. 6679, pp.25–20 (1998). For additional reviews of gene therapy technology, see Friedmann, *Science,* 244: 1275–1281 (1989); Verma, *Scientific American:* 68–84 (1990); and Miller, *Nature,* 357: 455–460 (1992). Alternatively, it is contemplated that in some human disease states, preventing the expression of, or inhibiting the activity of, Atr-2 will be useful in treating the disease states. It is contemplated that anti-sense therapy or gene therapy (for example, wherein a dominant negative Atr-2 mutatnt is introduced into a target cell type) could be applied to negatively regulate the expression of Atr-2.

The invention also provide compositions comprising modulators of Atr-2 biological activity. Preferably, the compositions are pharmaceutical compositions. The pharmaceutical compositions optionally may include pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The pharmaceutical compositions can be packaged in forms convenient for delivery. The compositions can be enclosed within a capsule, sachet, cachet, gelatin, paper, or other container. These delivery forms are preferred when compatible with entry of the immunogenic composition into the recipient organism and, particularly, when the immunogenic composition is being delivered in unit dose form. The dosage units can be packaged, e.g., in tablets, capsules, suppositories or cachets.

The pharmaceutical compositions may be introduced into the subject to be treated by any conventional method including, e.g., by intravenous, intradermal, intramuscular, intramammary, intraperitoneal, intrathecal, intraocular, retrobulbar, intrapulmonary (e.g., aerosolized drug solutions) or subcutaneous injection (including depot administration for long term release); by oral, sublingual, nasal, anal, vaginal, or transdermal delivery; or by surgical implantation, e.g., embedded under the splenic capsule, brain, or in the cornea. The treatment may consist of a single dose or a plurality of doses over a period of time.

Compositions are generally administered in doses ranging from 1 µg/kg to 100 mg/kg per day, preferably at doses ranging from 0.1 mg/kg to 50 mg/kg per day, and more preferably at doses ranging from 1 to 20 mg/kg/day. The composition may be administered by an initial bolus followed by a continuous infusion to maintain therapeutic circulating levels of drug product. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, *Remington's Pharmaceutical Sciences,* 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood levels dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

It will be appreciated that the pharmaceutical compositions and treatment methods of the invention may be useful in the fields of human medicine and veterinary medicine. Thus, the subject to be treated may be a mammal, preferably human, or other animals. For veterinary purposes, subjects include, for example, farm animals including cows, sheep, pigs, horses, and goats, companion animals such as dogs and cats; exotic and/or zoo animals; laboratory animals including mice, rats, rabbits, guinea pigs, and hamsters; and poultry such as chickens, turkeys, ducks and geese.

Association of Atr-2 with cell cycle progression makes compositions of the invention, including for example an Atr-2 polypeptide, an inhibitor thereof, an antibody, or other modulator of Atr-2 expression or biological activity, useful for treating any of a number of conditions. For example, aberrant Atr-2 activity can be associated with various forms of cancer in, for example, adult and pediatric oncology, including growth of solid tumors/malignancies, myxiod and round cell carcinoma, locally advanced tumors, metastatic cancer, human soft tissue sarcomas, cancer metastases, including lymphatic metastases, squamous cell carcinoma of the head and neck, esophageal squamous cell carcinoma, oral carcinoma, blood cell malignancies, including multiple myeloma, leukemias, effusion lymphomas (body cavity based lymphomas), thymic lymphoma lung cancer, including small cell carcinoma, non-small cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, and solid tumors in the ovarian follicle, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas, skin cancers, including malignant melanoma, tumor progression of human skin keratinocytes, and squamous cell cancer, hemangiopericytoma, and Kaposi's sarcoma. Still other conditions include aberrant apoptotic mechanisms, including abnormal caspase activity; aberrant enzyme activity associated with cell cycle progression, include for example cyclins A, B, D and E; alterations in viral (e.g., Epstein-Barr virus, papillomavirus) replication in latently infected cells; chromosome structure abnormalities, including genomic stability in general, unrepaired chromosome damage, telomere erosion (and telomerase activity), breakage syndromes including for example, Sjogren's syndrome and Nijimegen breakage syndrome; embryonic stem cell lethality; abnormal embyonic development; sensitivity to ionizing radiation; acute immune complex alveolitis; and Fanconi anemia.

The invention is exemplified by the following examples. Example 1 relates to identification of cDNAs encoding proteins related to PIK kinase. Example 2 describes identification of additional sequences in an Atr-2-encoding cDNA. Example 3 addresses Northern analysis of Atr-2 expression. Example 4 described chromosomal localization of an Atr-2 gene. Example 5 relates to production of anti-Atr-2 polypeptide antibodies. Example 6 describes expression of Atr-2 in mammalian cells. Example 7 describes kinase activity of a truncated form or Atr-2.

EXAMPLE 1

Identification of a cDNA Encoding a PIK-Related Protein

In an attempt to identify novel genes within the checkpoint kinase family, several searches of the National Center for Biotechnology Information (NCBI) EST database were carried out. In the first search, the DNA query sequences were those encoding PI3 kinase (GenBank® Accession No: Z46973), P110 kinase α (GenBank® Accession No: U79143), P110 kinase β (GenBank® Accession No: S67334), P110 kinase γ (GenBank® Accession No: X83368), P110 kinase δ (GenBank® Accession No: U86453), FRAP (GenBank® Accession No: L34075), ATR (GenBank® Accession No: Y09077), ATM (GenBank® Accession No: U26455), TRRAP (GenBank® Accession No: AF076974), PI3 kinase with C2 domain (GenBank® Accession No: AJ000008), PI4 kinase (GenBank® Accession No: AB005910), PI4 kinase/230 (GenBank® Accession No: AF021872), and DNA-PKcs (GenBank® Accession No: U34994). A blastn search was performed and a list of EST sequences corresponding to these query sequences was generated. In the second search, protein query sequences were P110 beta, FRAP, ATR, ATM, TRAPP, and DNA-PKcs and a tblastn search was performed. Those ESTs identified in the first search were subtracted from the results of the second search and the remaining sequences were analyzed.

One Genbank® EST, designated AI050717, was identified with a DNA sequence that was not identical to any of the query sequences and was not present in the non-redundant portion of GenBank®. When the predicted amino acid sequence for AI050717 was aligned with the query sequences, the highest homology was in the kinase domains of the query sequences. The protein encoded by AI050717 showed the most similarity to a putative kinase in C. elegans designated CE08808.

In an attempt to isolate a full length cDNA corresponding to AI050717, PCR was carried out on a Quickclone® human testis cDNA library (Clontech) to first amplify the AI050717 sequence. Two forward and two reverse primers were designed based on the sequence of AI050717 as set out in SEQ ID NOs: 9 to 12.

| 19F | GGGCGGAACCATCACAATCT | SEQ ID NO:9 |
|---|---|---|
| 22F | CGGAACCATCACAATCTTAC | SEQ ID NO:10 |
| 299R | CGTTGTTGCCATCGTTTGTA | SEQ ID NO:11 |
| 312R | TAAGGCAGCTTCCCGTTGTT | SEQ ID NO:12 |

PCR was carried out in a reaction including 1×Perkin Elmer PCR buffer, 1.5 mM $MgCl_2$, 0.16 mM dNTPs, 1 ng human testis cDNA, and primers as indicated below. Reaction tubes were first heated to 94° C. for two minutes, and reactions were initiated with addition of 0.5 μl AmpliTaq® polymerase. PCR conditions included a first incubation at 94° C. for five minutes, followed by 30 cycles of 94° C. for one minute, 60° C. for one minute, and 72° C. for one minute, followed by incubation at 72° C. for seven minutes. Individual reactions included 100 ng of each primer pairs 19F/299R, 19F/312R, 22F/299R and 22F/312R. Aliquots from each reaction were separated on an agarose gel and ethidium bromide staining indicated that no amplification products were obtained.

Nested PCR was carried out on products obtained in the first reactions using primer pairs 19F/312R and 22F/312R as templates. Reaction conditions were modified and amplifications repeated using primer pair 22F/299R in an initial incubation at 94° C. for five minutes, followed by 30 cycles of 94° C. for 30 seconds, 55° C. for 30 seconds, and 72° C. for 30 seconds. The amplification reaction included 1×Perkin Elmer PCR buffer, 1.5 mM $MgCl_2$, 330 ng primer 22F, 330 ng primer 299R, 320 nM NTPs, 0.5 U Taq polymerase, and 1 μl from the first PCR amplifications utilizing primer pairs 19F/312R and 22F/312R. An aliquot from each reaction was separated on an agarose gel and ethidium bromide staining indicated that both reactions gave a 277 bp product. The amplification product was purified with QIAquick® PCR Purification kit and eluted into 40 μl $H_2O$.

The fragment was subcloned into pCR3.1 T/A vector (Invitrogen) in separate reactions that included 1 μl PCR product, 1 μl 10×ligation buffer, 2 μl vector, 5.5 μl $H_2O$, and 1 μl T4 DNA ligase. Ligation was carried out overnight at 15° C. Five μl of each ligation reaction was transformed into TOP10F' cells (Invitrogen) and the transformation mixture was plated. Each ligation, and a control mixture, resulted in approximately 200 colonies. Twelve colonies from each plate were picked and PCR carried out to screen for the expected insert. Results indicated that none of the colonies included an insert.

The ligation reaction was then repeated as described above except that the vector was first denatured at 65° C. for two min, and then quenched on ice. The remainder of the procedure was carried out as described above. No significant increase in number of colonies was detected in the transformation derived from the ligation of vector and PCR fragment compared to the transformation using vector alone.

While these experiments generated PCR products of the correct size, they failed to produce a cDNA clone representing the sequences of AI050717. Therefore, a different approach was undertaken using a Marathon® cDNA cloning system (Clontech) wherein PCR reactions were carried out to extend the sequences in AI050717 at the same time as attempting to obtain the full length AI050717 clone.

Using primers described above designed to amplify an AI1050717 sequence, PCR was carried out to extend the EST 3' sequence in order to determine if the EST was part of a cDNA containing a functional kinase domain. PCR was carried out using primer pair 19F and AP1 (Marathon cDNA Cloning System, Clontech) with Marathon® testis cDNA as template.

| AP-1 | CCATCCTAATACGACTCACTATAGGGC | SEQ ID NO:13 |
|---|---|---|

A stock reaction mixture was prepared including 36.5 μl $H_2O$, 5 μl 10×cDNA polymerase buffer, 0.5 μl 20 mM dNTPs, and 1 μl Advantage® polymerase. Two reactions were set up, each including a constant amount of AP1 primer, but one including 250 ng 19F primer (reaction 1), and another including 500 ng 19F primer (reaction 2). Amplification conditions included a first incubation at 94° C. for five min, followed by 30 cycles of 94° C. for 30 sec, 60° C. for 30 sec, and 68° C. for two min. An aliquot from each reactions was removed and separated on an agarose gel and staining indicated smears in all three lanes.

PCR was then repeated using primer 22F and AP1 and template DNA from the first reactions 1 and 2. Stock reaction mixture included 93 μl $H_2O$, 15 μl 10×cDNA polymerase buffer, 1.5 μl 20 mM dNTPs, and 3 μl Advantage® polymerase. Each reaction included 37.5 μl of the stock mixture and either (i) 5 μl primer 22F, 1 μl primer AP1, and 1 μl reaction 1, (ii) 5 μl primer 22F, 1 μl primer AP1, and 1 μl reaction 2, and (iii) 5 μl primer 22F, 5 μl 299R, and 1 μl reaction 1. Reaction conditions included an initial incubation at 94° C. for five min, followed by 30 cycles of 94° C. for 30 sec, 55° C. for 30 sec, and 68° C. for 30 sec. Agarose gel separation of the amplification products still showed smears in lanes from reactions (i) and (ii), while a band of approximately 300 fragment was detected in the reaction (iii) which was presumed to represent the sequences in the AI050717 EST.

In an attempt to clone this approximately 300 bp fragment, PCR was repeated using amplification products from the previously described reactions using Marathon® and Quickclone DNA as template. Each amplification reaction included 1 μl from either of the previous the Marathon® or Quickclone reactions, 5 μl primer 22F, 5 μl primer 299R, 5 μl 10×cDNA polymerase buffer, 0.4 μl 20 mM dNTPs, and 1 μl polymerase. Reaction conditions included an initial incubation at 94° C. for five min, followed by 30 cycles of 94° C. for 30 sec, 55° C. for 30 sec, and 68° C. for 30 sec. Ligation into pCR3.1 was carried out at 15° C. overnight using the amplification products with 2 μl heat denatured vector, 1 μl 10×ligation buffer, 5.5 μl H$_2$O and 1 μl ligase. Transfections with each reaction mixture were carried out, the transfection mixtures plated, colonies picked and plasmid minipreps carried out on the picked colonies. Plasmid from each miniprep was digested with EcoRI and separated on agarose gel. All picked colonies were found to include an insert of the expected size. Sequence analysis confirmed that this insert contained sequence from nucleotide 22 to 299 of AI050717.

Extension of the AI050717 Clone

In an attempt to isolate a more complete cDNA clone including sequences in AI050717, additional PCR amplifications were carried out using a testis cDNA library as template.

Primers 19F, 22F, 299R, and 312R were redesigned to have higher melting temperatures for use at high annealing temperatures required for Touchdown® PCR. In Touchdown® PCR, the initial annealing temperature prior to amplification at 72° C. serves to increase the specificity of annealing of the primers to the cDNA of interest. The temperature is then decreased to allow for an increase in the specific PCR product. The rediesigned primers are set out in SEQ ID NOs: 14 to 17.

```
19Fext    GGGCGGAACCATCACAATCTTACC    SEQ ID NO:14

22Fext    CGGACCCATCACAATCTTACCGACT   SEQ ID NO:15

299Rext   CGTTGTTGCCATCGTTTGTAAAGAC   SEQ ID NO:16

312Rext   TAAGGCAGCTTCCCGTTGTTGCCA    SEQ ID NO:17
```

A stock reaction mixture was prepared including 94.5 μl H$_2$O, 15 μl 10×cDNA polymerase buffer, 1.5 μl dNTPs, and 3 μl Advantage® polymerase. Reactions included 38 μl of the stock mixture and either (i) 1 μl testis Marathon® cDNA, 5 μl primer 19Fext, and 1 μl primer AP1 (the 3' reaction), or (ii) 1 μl testis Marathon® cDNA, 5 μl primer 299Rext, and 1 μl primer AP1 (the 5' reaction). Touchdown® PCR was performed under conditions including an initial incubation at 94° C. for one min, followed by five cycles of 94° C. for 30 sec and 72° C. for three min, five cycles of 94° C. for 30 sec and 70° C. for three min, 25 cycles of 94° C. for 30 sec and 68° C. for three min, then a holding step at 4° C. An aliquot from each reaction was separated on an agarose gel and no amplification products were detected upon staining.

The PCR was repeated using nested primers and DNA from the previous 3' and 5' reactions as template. A stock reaction mixture was first prepared including 94.5 μl H$_2$O, 15 μl 10×cDNA polymerase PCR buffer, 1.5 μl 20 mM dNTPs and 3 μl Advantage® polymerase. Each amplification included 38 μl of the stock mixture and either (i) 1 μl of the previous 3' reaction mixture, 5 μl primer 22Fext and 1 μl primer AP2 (for the 3' extension, this primer anneals to the 3' end of all cDNAs in a Marathon® library), (ii) 1 μl of the previous 5 ' reaction mix, 5 μl primer 19AS, and 1 μl primer AP2 (the 5' extension), or (iii) 1 μl of the previous 3 ' reaction mix, 5 μl primer 22Fext, and 5 μl primer 299Rext (the control reaction).

```
AP-2    ACTCACTATAGGGCTCGAGCGGC    SEQ ID NO:18
```

Amplification conditions were as described in the above Touchdown® PCR. Results indicated that the control reaction produced significant product, but smears were detected in the 3' and 5' reaction lanes. When the PCR was repeated using 2 μl of each primer, the same results were detected.

Amplification products were then ligated into pCR3.1 T/A vector in a reaction carried out as described above, the ligation products were transformed into TOP10F' cells, and the cells were plated. In transformation with the vector alone, approximately 200 colonies were detected, while with transformation with the ligation products from the 3' and 5' amplifications, approximately 200 and 150 colonies, respectively, were detected. In view of the high numbers of colonies observed in the absence of insert, the PCRs, ligations, transfections and platings were repeated, and the same results were obtained in the second attempt.

Colonies were then screened for plasmids bearing inserts using PCR with primers 22Fext and 299Rext. A stock reaction mixture was prepared including 100 μl Perkin Elmer PCR buffer, 100 μl 10×MgCl$_2$, 8 μl 20 mM dNTPs, 100 μl primer 22Fext, 100 μl 299Rext, 10 μl AmpliTaq® polymerase, and 582 μl H$_2$O. Forty eight colonies from the 3' reaction were individually placed in 20 μl of the stock reaction mixture, and PCR performed under conditions including an initial incubation at 94° C. for one min, followed by 35 cycles of 94° C. for 30 sec, 60° C. for 30 sec, and 72° C. for 30 sec, and a final hold at 4° C. The reaction products were separated on agarose gels and all colonies picked were found to include inserts.

Twenty colonies arising from the 3' extension reaction were picked, the cells grown overnight in two ml media, and plasmids isolated from the cells using a Wizard® Miniprep kit. Isolated plasmids were digested with EcoRI and the digestion products were separated on an agarose gel. Plasmids were precipitated from those preparations showing the largest inserts on the gel and the inserts were sequenced.

EXAMPLE 2

Extension of the Atr-2 cDNA 3' of the AI050717 Sequence

3' Extension

Sequence analysis of the 3' extended cDNAs showed that clone 2 (SEQ ID NO: 43), which contained an approximately 1.2 kb insert, contained sequences at one end that were similar to those found at the ends of the kinase domain of PIK-related kinases and were highly related to the *C. elegans* PIK (CE08808). In particular, the predicted amino acid sequence encoded by this clone demonstrated that the kinase domain contained homologous amino acids found in the PIK-related kinases that have protein kinase activity.

This observation was different from what was found in TRRAP and Tra1, both of which lack some of the conserved amino acids and are therefore thought to lack protein kinase activity.

In order to determine if the AI050717 sequences and the kinase domains sequences were contiguous, several more primers were designed to amplify the product directly.

```
Primer 15158
CCACCTCCACCAATAGAGAGCACCAGC     SEQ ID NO:19

Primer 15156
GCTCTGCTTGCTCTCGGCCTGCTG        SEQ ID NO:20

Primer 15157
GGACTTGCTCGTCTTGCTCTCGGC        SEQ ID NO:21
```

PCR amplification was carried out in reactions containing 5 μl Marathon® testis cDNA, 100 ng each primer pair 22Fext and 15157 or 22Fext and 15158, 1×cDNA polymerase reaction buffer, 0.2 mM dNTPs, 1 μl Advantage cDNA polymerase mix, and 39.5 μl $H_2O$. Touchdown® PCR was performed as previously described. A 10 μl aliquot of each reaction mixture was separated on a 2% agarose gel and results showed that both reactions yielded products of approximately 1 kb. A 2 μl aliquot was removed from each reaction and ligated into pCR3.1 TA cloning vector at 14° C. for 20 hrs and the ligation mixtures transformed into TOP10F' bacteria. Nine colonies from each ligation were picked, cultures grown, and plasmid DNA isolated. The plasmid DNA was digested with EcoRI and most clones were found to contain an insert of the expected size.

Sequence analysis demonstrated that the PCR product generated from primers 22Fext and 15157 yielded the largest clone, which was designated 22F/57. The predicted amino acid sequence demonstrated that this clone contained all sequences found in the kinase domain of PIK-related kinases.

To further extend the 3' end of the clone, a primer was designed based on the 3' end of clone 22F157.

```
3'E2F    GTCTATGGTGGAGGTGGCCAGCAG.     SEQ ID NO:22
```

This primer and the AP2 primer were used in nested PCR to amplify additional cDNA sequences 3' to 22F/57. A 50 μl PCR reaction mix was prepared containing 0.5 μl the reaction mixture generated by PCR of Marathon® testis cDNA with primers 19F and AP1, 1×cDNA polymerase reaction buffer, 0.2 mM dNTPs, 100 ng each of the primers 3'E2F and AP2, and 1 μl Advantage® polymerase mix. Touchdown® PCR was performed as previously described. Amplification products were separated on an agarose gel and ranged in size from approximately 200 bp to approximately 3 kb. Bands representing the highest molecular weight products were excised from the gel, purified, and ligated into pCR2.1® using a TOPO TA cloning® vector. The resulting construct was transformed into TOP10 cells and one-tenth of the transformation mixture was plated onto agar plates. When no colonies were obtained, the remainder of the transformation mix was plated and five colonies were subsequently isolated.

PCR was repeated using 0.5 μl and 1 μl of template and either 1 or 2 μl of primer 3'E2F. Touchdown® PCR with performed with the first five cycles at 75° C. instead of 72° C. Reaction products were separated on an agarose gel and showed a distribution ranging from about 100 bp to 3 kb. Approximately 0.5 μl of the reaction mixture generated using 0.5 μl of template and 2 μl of 3'E2F was ligated into pCR2.1® using a TOPO TA® cloning vector. The ligation mixture was transformed into TOP10 bacteria and the bacteria plated onto agar plates. The reaction yielded hundreds of colonies.

These colonies and the colonies generated by ligation of the gel purified PCR products described above were screened for inserts using PCR. Five colonies were identified that contained inserts and plasmid DNA was prepared from each. Two of the clones, 3'E2F-1 and 3'E2F-28 contained inserts of about 1.8 kb.

Sequence analysis of the clones demonstrated that the 3'E2F-28 clone (SEQ ID NO: 41) showed very high sequence homology, at both nucleotide and amino acid levels, to a partial cDNA sequence designated KIAA0421 found in the GenBank® database (Accession Number AB007881). The KIAA clones were identified as part of a sequencing project to identify large cDNAs in the brain [Ishikawa et al., *DNA Res.* 4:307–313(1997)]. KIAA0421 was described as a 5717 bp cDNA isolated from a human male brain cDNA library, and encoding a protein related (by amino acid homology) to Lambda/iota Interacting Protein (LIP) [Dias-Meco et al., *Mol. Cell Biol.*, 16:105–114(1996)], a protein that interacts with the atypical protein kinase C isotype λ/1. KIAA0421 sequences surrounding the LIP-related region are similar to sequences in the kinase domains of PIK-related kinases; the KIAA0421 region upstream of the LIP-homologous domain is identical to the kinase domain of Atr-2 and the sequence downstream of the LIP domain is most similar to the carboxy terminus of the *C. elegans* PIK-related kinase that is most closely related to Atr-2. These clones may present the 3' end of the Atr-2 coding sequence.

In an attempt to isolate clones that contained these sequences, several primers were designed.

```
KIDrev    GATGTCAATCTTTCGCCAAGCTATGG    SEQ ID NO:23

SLQrev    GCTGCAGGCTTGTCTTACAAC         SEQ ID NO:24

MCSrev    GCAAGCTCTAACTCAGACACTG        SEQ ID NO:25

SSArev    GCAGATGACGTTGGACTCGAAC        SEQ ID NO:26

MARQrev   CTACTGTCTTGCCATTCACACC        SEQ ID NO:27
```

PCR reactions were prepared with using 100 ng of each of these primers in combination with the 369f primer, 2.5 μl Marathon® testis cDNA, 1×cDNA polymerase buffer, 0.2 mM dNTPs and 1 μl Advantage® polymerase. Touchdown® PCR was performed and the products were separated on a 1.2% agarose gel. Amplification products were obtained from reactions containing KIDrev, MCSrev and MARQrev primers but not from reactions using SLQrev and SSArev primers. Further, only the amplification product from the reaction containing the KIDrev primer was the expected size; all other amplification products were smaller than expected. Two μl of the products from each reaction was ligated into pCR2.1® using a TOPO TA cloning® kit (Invitrogen), each ligation mixture was transformed into TOP10, and the transformed cells were plated on agar plates. Plasmid DNA was isolated from these colonies and the sequences was analyzed.

Sequence analysis demonstrated that the clones derived from the 369f/KIDrev amplification started and ended at the expected positions with respect to the sequence of KIAA0421. The amplification products from PCR using the 369f/MARQrev primers started at sequences farther downstream than expected, but ended at the position predicted by the design of the primers. The products derived from PCR using the 369f/MCSrev primers showed no homology to KIAA0421, suggesting that the primers did not anneal in a sequence-specific manner. Two additional primers, RLLfor and TRTrev, were designed to repeat the PCR in order to obtain sequences of this region.

```
RLLfor  CAGACTACTACATGCTCAGTACGG    SEQ ID NO:28

TRTrev  CCAGGTTTATGGCTTCTGCAGTTCTTG SEQ ID NO:29
```

PCR reactions were prepared containing using 100 ng each of RLLfor and TRTrev primers, 2.5 µl Marathon® testis cDNA, 1×cDNA polymerase buffer, 0.2 mM dNTPs and 1 µl Advantage® polymerase. Touchdown® PCR was carried out, the products were separated on a 1.2% agarose gel, and a product of the expected size was obtained. Two µl of these products was ligated to pCR2.1® using a TOPO TA cloning® kit (Invitrogen), the ligation mixture was transformed into TOP10 bacteria, and the transformed cells were plated on agar. Plasmid DNA was isolated from these colonies and the sequences determined. These clones contained the expected sequences as predicted by the primers used in the reaction.

5' Extension

In order to extend the 5' AI050717 sequence, a first PCR was carried out in a reaction containing 100 ng each of primers 299ext and AP1, 1 ng of Marathon® testis cDNA, 1×cDNA polymerase buffer, 0.2 mM dNTPs and 1 µl Advantage® polymerase. Touchdown® PCR was performed as described above. A second nested PCR was then performed on the products of the first PCR using 19AS, an anti-sense primer that corresponded to the 5' sequence of AI050717.

```
Primer 19AS  GGTAAGATTGTGATGGTTCCGCCC SEQ ID NO:30
```

The nested PCR reaction mixture contained 100 ng each of primers 19AS and AP2, 1 µl of the primary PCR reaction (above), 1×cDNA polymerase buffer, 0.2 mM dNTPs and 1 µl Advantage® polymerase. Touchdown® PCR was performed and the products were separated on an agarose gel. A smear ranging in size from 500 bp to 6 kb was observed. Approximately two µl of the reaction mix was ligated into pCR3.1 for 20 hours at 15° C. and the ligation mixture transformed into TOP10F' E. coli. Eighteen colonies were cultured, and plasmid DNA was prepared and digested with EcoRI. Five clones contained inserts released by EcoRI ranging from 200 to 500 bp in size. Sequence analysis of these clones demonstrated that the longest clone containing sequences contiguous with Atr-2 was 243 bp in length. This sequence was used to design another primer, designated 5'E2R, for extending the 5' end of Atr-2.

```
5'E2R    GCACGTTTCTGTGCTCTCTGTTGC SEQ ID NO:31
```

Nested PCR was carried out in a reaction containing 100 ng each of primers 5'E2R and AP2, 1 µl of the PCR reaction derived from the PCR on testis cDNA with primer pair 299Rext and AP1 (SEQ ID NOs: 16 and 13), 1×cDNA polymerase buffer, 0.2 mM dNTPs and 1 µl Advantage® polymerase. Touchdown® PCR was performed and the products were separated on an agarose gel. A smear was observed on the gel with a prominent band at 600 bp and a minor hand at about 1 kb. Two µl of the reaction mixture was ligated into pCR3.1, and the ligation mixture transformed into TOP10F' bacteria. After plating, 30 colonies were screened for inserts using PCR with the M13 vector primer and primer 5'E2R. Most colonies contained inserts. The colonies containing the largest inserts were cultured and plasmid DNA subjected to sequencing.

Sequence analysis demonstrated that clone 5'E2#2 contained the largest insert and showed significant homology to the C. elegans PIK-related clone and FRAP. Since this cDNA showed an open reading frame through its entire sequence, it was expected that the clone did not encode an initiating methionine. As a result, another primer designated STDrev was designed to further extend the 5' end of the cDNA.

```
STDrev: GGCCATCCACAATCATGTCATCAGTGCTC SEQ ID NO:32
```

Touchdown® PCR was carried out in a mixture containing 100 ng of 5'E2R and AP1, 1 µl Marathon® testis cDNA, 1×cDNA polymerase buffer, 0.2 mM dNTPs and 1 µl Advantage® polymerase. One µl of the first amplification mixture was used as template in a second nested Touchdown PCR reaction containing 100 ng each of primers STDrev and AP2, 1×cDNA polymerase buffer, 0.2 mM dNTPs and 1 µl Advantage® polymerase and amplification products were separated on an agarose gel. A smear ranging from 200 bp to 2 kb was observed, with prominent bands at 200 bp, 600 bp and 1 kb. Two µl of the amplification mixture was ligated into vector pCR2.1® using a TOPO TA cloning® kit (Invitrogen), the ligation mixture transformed into TOP10, and the transformed bacteria plated on agar plates. Sixteen colonies were isolated and plasmid DNA prepared and digested with EcoRI to determine insert sizes. Five plasmids containing the largest inserts were sequenced.

Sequence analysis of these clones revealed that the longest clone, 5'E3#1 (SEQ ID NO: 42) contained about 1200 bp of additional Atr-2-encoding sequence. Blastx analysis of the predicted amino acid sequence of the clones demonstrated that none of the clones showed significant homology to any sequences in the nonredundant database of GenBank®. The fact that the longest clone from this PCR included an open reading frame suggested that this clone did not contain the initiating methionine residue.

In an effort to identify additional 5' sequences, another primer, PIRrev, was designed for use in RACE reactions.

```
PIRrev CTAATTCCATGAGATGGCTTCTAATTGG   SEQ ID NO:33
```

A PCR reaction was prepared containing 100 ng of PIRrev and AP2 primers, 1 µl of the amplification product from PCR using primers STDrev and AP1, 1×cDNA polymerase buffer, 0.2 mM dNTPs and 1 µl Advantage® polymerase. Touchdown® PCR was performed and the products were separated on a 1.2% agarose gel. A smear was detected ranging from 200 bp to 2 kb Two µl were ligated into pCR2.1® using a TOPO TA® cloning kit (Invitrogen), the ligation mixture was transformed into TOP10 bacteria, and the transformed cells were plated on agar. Eighteen colonies were selected for plasmid preparation and the sequence of five plasmid DNAs, each containing EcoRI fragments larger than 0.5 kb, was analyzed. The largest of these clones contained approximately 800 bp. Blastx analysis revealed significant homology to two partial coding sequences in the nonredundant database, KIAA0020 (accession number AAC31670) and a sequence obtained by sequencing artificial chromosomes derived from human chromosome 16 (human Chromosome 16 BAC clone CIT987-SK-A-61E3, accession number AC003007). The homology to the chromosome 16 clone correlated with chromosomal mapping data demonstrating the localization of Atr-2 to chromosome 16p12 (see Example 4).

Using this sequence, another primer designated CECrev, was designed to further extend the 5' sequence.

```
CECrev CGGCAATTGAGATGTAGCACTCAC    SEQ ID NO:34
```

A PCR reaction was prepared containing 100 ng of CECrev and AP2, 1 μl of the product derived from PCR with primers STD rev and AP1, 1×cDNA polymerase buffer, 0.2 mM dNTPs and 1 μl Advantage® polymerase. Touchdown® PCR was performed and the products were separated on a 1.2% agarose gel. A smear of products ranging from 200 bp to 8 Kb was observed. Two μl of the reaction was ligated to pCR2.1® using a TOPO TA® cloning kit (Invitrogen), the ligation mixture was transformed into TOP10 cells, and the cells were plated on agar. Eighteen white colonies were selected and DNA from clones with the five largest EcoRI inserts were sequenced. These clones also showed significant homology to KIAA0220 and the chromosome 16 BAC clone, but none encoded the initiating methionine.

In a further effort to isolate sequences including the start codon, another primer, MTWfor, was designed using the sequence data obtained from the KIAA0220 and chromosome 16 BAC clones to span the initiating methionine.

```
MTWfor ATGACTTGGGCTTTGGAAGTAGCTGTTC    SEQ ID NO:35
```

Touchdown® PCR was carried out using 100 ng each of MTWfor and PIRrev, 1 μl Marathon testis cDNA, 1×cDNA polymerase buffer. 0.2 mM dNTPs and 1 μl Advantage® polymerase, and a product of approximately 2 kb was obtained. Two μl of the reaction was ligated into pCR2.1® using a TOPO TA® cloning kit (Invitrogen), the ligation mixture was transformed into TOP10 bacteria, and the transformed cells were plated on agar. Six white colonies were selected and restriction digestion demonstrated that five of the six contained 2 kb inserts. Sequence analysis on three of the clones indicated that they encoded the initiating methionine of the KIAA0220 and chromosome 16 BAC clones and also contained sequences previously found in the Atr-2-encoding sequence.

In order to confirm that the combined cDNA encoded a single Atr-2 coding region, PCR was carried out to generate two overlapping clones spanning the complete protein coding region. A new primer, MTWfor2, was synthesized as a forward primer to amplify the 5' end of the cDNA.

```
MTWfor2
       GGACACGAGGAAACTGTTAATGACTTGGGC    SEQ ID NO:36
```

Separate amplification reactions were carried out using 100 ng of primers MTWfor2/312rev-ext and primers 22Fext/MRQrev, 5 μl Marathon® testis cDNA, 1×cDNA polymerase buffer, 0.2 mM dNTPs and 1 μl Advantage® polymerase. Touchdown® PCR was performed and the products were separated on a 1.2% agarose gel. Amplification products of the ekpected size were observed, along with a smear of smaller size products. The bands of the expected size were isolated and the DNA eluted and ligated into pCR2.1® using a TOPO TA® cloning kit (Invitrogen). The ligation reaction was used to transform TOP10 bacteria and the bacteria were plated on agar. Plasmid DNA was isolated from resulting colonies and sequences of three individual clones from each ligation reaction were analyzed.

The sequences from three Atr-2 mtw-312rev clones are set out in SEQ ID NOs: 6, 7, and 8, and the sequences from three Atr-2 22F-MARQ clones are set out in SEQ ID NOs: 3, 4, and 5, respectively, were used to deduce a consensus cDNA sequence encoding Atr-2. Clones p22F-MARQ.3 and pMTW-312R.5 were deposited on Oct. 1, 1999, under terms of the Budapest Treaty with the American Type Culture Collection, 10801 University Blvd., Manassas, Va. 20110-2209, and assigned Accession Numbers PTA-810 and PTA-811, respectively. The consensus poly-nucleotide and deduced amino acid sequences are set out in SEQ ID NOs: 1 and 2, respectively. The entire Atr-2-encoding clone was 8838 bp in length and predicted to encode a protein of 2930 amino acids. PFAM analysis, a program designed to identify proteins motifs, identified the PIK-related kinase domain but no other motifs.

The Atr-2 protein coding domain begins with a methionine residue at nucleotide 31 and ends with a stop codon at nucleotide 8821. The full length protein is 2930 amino acids in length. Amino acids 1 to 546 are 95% identical to the protein encoded by KIAA0220. Further, amino acids 1629 to 2930 are 100% identical to KIAA0421 and amino acids 2152 to 2930 are 100% identical to the Lambda/iota interacting protein, LIP. The PIK-related kinase domain is between amino acid residues 1413 to 1695 and there is between 39% and 48% identity in this region with the kinase domains of the PIK-related kinases FRAP, Tor1, Tor2, and the C. elegans PIK-related kinase SMG-1 (Table 1). In addition, the carboxy termini of these proteins also show a significant degree of conservation (Table 1). Interestingly in Atr-2, the kinase domain is separated from the carboxy terminus by a large sequence which includes the LIP domain.

TABLE 1

Atr-2 Amino Acid Homologies

| | Percent Amino Acid Identity | |
|---|---|---|
| | Kinase Domain | Carboxy Terminus |
| C. elegans SMG-1 | 48 | 36 |
| S. cerevisiae FRAP | 37 | 42 |
| S. cerevisiae Tor1p | 37 | 40 |
| Human Tor2p | 39 | 42 |
| Human Atr | 33 | 28 |
| Human Atm | 33 | 37 |
| Human DNAPK | 25 | ND |

Atr-2 is most closely related to the C. elegans protein SMG-1. Mutants of the SMG-1 gene indicate that the encoded protein is involved in mRNA surveillance in a pathway called nonsense mediated mRNA decay (NMD). Proteins ion this pathway appear to monitor aberrant mRNAs and target them for elimination to avoid translation of deleterious proteins [Culbertson, et al., Trends in Genet. 15:74–80 (1999)]. SMG-2, another C. elegans protein involved in this pathway is phosphorylated in cells and its phosphorylation is dependent on SMG-1 [Page, et al., Mol. Cell. Biol 9:5943–5951(1999)].

There are many human diseases and cancers in which mutations in genes lead to premature chain termination presumably through the NMD pathway. These diseases include ataxia-telangiectasia, breast cancers caused by mutation in the BRCA-1 gene, β-thalassemia, Marfin syndrome, and gyrate dystrophy. It is possible that inhibition of the NMD pathway could lead to the production and accumulation of the particular gene products thus alleviating the symptoms of these disease. Alternatively, in diseases in which truncated proteins are produced and bock protein activity by acting in a dominant negative fashion, gene therapy using proteins in the NMD pathway may be of therapeutic value. The similarity between Atr-2 and SMG-1 indicates that Atr-2 may be involved in the onset or maintenance of any of these disease states.

EXAMPLE 3

Northern Analysis

In order to assess expression of Atr-2, hybridization with Multiple Tissue Northern blots (Clontech) was performed. A stock hybridization mixture was prepared including 5×SSPE, 10×Denhardt's, 100 µg/ml salmon sperm DNA, 50% formamide and 2% SDS. Prehybridization in this mixture was first carried out for five hours at 42° C. A hybridization probe was prepared using PCR in a reaction containing 4 µl 10 Perkin Elmer PCR buffer, 4 µl 10 MgCl$_2$, 4 µl 2 mM dATP and dGTP and 10 µM dCTP and dTTP, 10 µCi each $^{32}$P-αCTP and $^{32}$P-αTTP, 1 µl primer 22F, 1 µl 299R, 1 µl template DNA from human testis PCR reaction derived from primers 19F and 312R (Example 1) and 24.5 µl H$_2$O. Reaction conditions included an initial incubation at 94° C. for five min, followed by 25 cycles of 94° C. for 15 sec, 60° C. for 15 sec, and 72° C. for 30 sec. Unincorporated nucleotides were removed from the reaction mixture using a NucTrap® column, pre-wet with 70 µl STE. The PCR mixture was removed from under the oil film, the volume brought up to 70 µl with STE, and the resulting mixture applied to the column. The column was eluted with 70 µl STE twice, radioactivity was determined using a 2 µl aliquot, the remaining probe boiled, and 25 µl of the probe added to the prehybrization mixture. Hybridization was carried out overnight at 42° C. The blot was washed one time for 15 min at room temperature in 2×SSC/0.1% SDS, and twice for 15 min at 55° C. in 0.1×SSC/0.1% SDS. Autoradiography was carried out four days.

Results indicated low levels of message greater than 9.5 kb in all tissues tested, with slightly higher levels in skeletal muscle, heart peripheral blood, thymus, and spleen.

EXAMPLE 4

Chromosomal Localization of the Atr-2 Gene

In an attempt to determine whether Atr-2 was associated with any known disease genes, chromosome mapping of Atr-2 was carried out using the Stanford Radiation Hybrid Panel (Research Genetics, Huntsville Ala.).

In this method, a human lymphoblastoid RM cell line was irradiated with 10,000 rad of X-rays and fused with a non-irradiated thymidine-resistant hamster cell line (A3). Fusion created 83 independent somatic hybrid cell lines containing chromosomes lacking successive regions with about 500 kb resolution. The radiation hybrids were screened for the presence of Atr-2 by PCR.

To determine whether the PCR primers chosen for the screen would hybridize to human DNA and not hamster DNA, a first PCR reaction was performed using either human (RM) or hamster (A3) genomic DNA. A reaction mixture was prepared containing 100 ng each of primer 22F and either of primers 299R or 312R, 1×AmpliTaq® buffer, 1.5 mM MgCl$_2$, 0.16 mM dNTPs, 0.25 U AmpliTaq® and 100 ng of genomic DNA. PCR was carried out with an initial cycle at 94° C. for 30 sec, followed by 30 cycles of 94° C. for 30 sec, 55° C. for 30 sec, 72° C. for 30 sec, a cycle of 72° C. for 7 min and a final 4° C. hold cycle. The products from these reaction were separated on an agarose gel.

PCR of the human genomic DNA yielded a strong band at about 750 bp that was also present, although in lower amounts, in the hamster genomic DNA. These bands were gel purified and sequenced with the 22F and 299R primers. Sequence analysis indicated that the amplification product contained Atr-2 sequences separated by intron sequences.

To an attempt tp eliminate the PCR product seen in the hamster DNA, the reaction was repeated using Advantage® polymerase and Touchdown® PCR. PCR was carried out in a reaction mixture containing 100 ng of either human or hamster genomic DNA, 100 ng each of primer 22Fext and either of primers 299Rext or 312Rext, 1×cDNA polymerase buffer, 0.2 mM dNTPs, and 1U Advantage® polymerase. Touchdown® PCR was carried out with an initial cycle of 94° C. for one min followed by five cycles of 94° C. for 30 sec and 75° C. for 2.5 min, five cycles of 94° C. for 30 sec and 70° C. for 2.5 min, 25 cycles of 94° C. for 30 sec and 60° C. for 2.5 min, and a final holding step at 4° C. The reaction products were separated on an agarose gel which revealed a major band of about 750 bp in the human genomic DNA sample with either set of primers, but only trace amounts of the same size product in the hamster DNA. These PCR conditions were then used to screen the radiation panel and the amplification products were separated on agarose gels. The resulting pattern of PCR products was forwarded to the radiation hybrid server at the Stanford Human Genome Center (rhserver@shgc.stanford.com) for analysis.

Atr-2 mapped to chromosome 16. The sequence mapped closest to SHGC-20000942, SHGC-9643 and SHGC-37696. Search of the chromosome 16 with these markers revealed that this location is 16p12. This chromosomal location correlates with the identity of the 5' end of the Atr-2 coding sequence with a partial sequence derived from sequencing of chromosome 16 (see Example 1).

EXAMPLE 5

Production of Antibodies to Atr-2

In an effort to generate antibodies that recognize Atr-2, two regions of Atr-2 were expressed as GST fusion proteins. The first fusion construct encoded the entire kinase domain, a region comprised of both conserved amino acids and unique amino acids in comparison to kinase domains of other PIK-related kinases Sequences amplified in PCR using primers 22f and 15157 were ligated into the EcoRI site of pGEX-3x and the ligation mixture was used to transform the bacterial strain, TOP10F'. Six colonies were generated and sequence analysis of the clones revealed that the Atr-2 protein coding sequences were in-frame with GST coding sequences, suggesting that a GST-Atr-2 fusion protein should be produced from the transformed bacteria upon induction with IPTG. Induction of these bacteria, however, did not show large amounts of GST-Atr-2 fusion protein.

In an effort to improve expression, the pGEX-Atr-2 plasmid was transformed into the bacterial strain, BL21 Supercodon (Stratagene). The GST fusion protein is purified using glutathione agarose and used as immunogen in mice and rabbits to generate monoclonal antibodies and polyclonal antibodies.

The second GST fusion construct encoded sequences within the kinase domain of Atr-2 that are unique to Atr-2 when compared to Atr, Atm, DNA-PK, FRAP, and TRRAP. Two primers, MFA-F and TQS-R, were designed.

| | | |
|---|---|---|
| MFA-F | CATGTTTGCTACAATTAATCGCCAAG | SEQ ID NO:37 |
| TQS-R | GACTGCGTAACTCTCCACCATTC | SEQ ID NO:38 |

A 50 µl PCR reaction was prepared containing 100 ng each of MFA-F and TQS-R primers, 75 ng pCR2.1®, primers 22F/57, 1×cDNA polymerase buffer, 0.2 mM dNTPs and 1 µl Advantage® polymerase. PCR included an initial denaturation cycle at 94° C. for 30 sec, followed by 25 cycles of: 60° C. for 30 sec and 72° C. for one min, and a final holding step at 4° C. A PCR product of approximately 450 bp was obtained, the fragment was ligated into pCR2.1® using the TOPO TA cloning® system and the ligation mixture was transformed into TOP10. Twelve colonies were chosen for plasmid preparation and one was found to include an EcoRI fragment of the correct size. Sequence analysis showed that there was a single nucleotide difference that resulted in changing a valine residue to an asparagine residue. As this change was unlikely to affect antibody production, this clone, called pCR2.1MFA/TQS, was selected for further cloning.

The pCR2.1MFA/TQS expression construct was digested with EcoRI and subcloned into the EcoRI site of pGEX-3x to give plasmid pGEX-MFA/TQS. The ligation mixtures were transformed into TOPIOF' and approximately 250 colonies were obtained. Eleven colonies were chosen for plasmid preparation and three appeared to have inserts of the correct size. Induction of these bacteria containing this plasmid however, did not result in large amounts of GST fusion protein.

In an effort to improve expression, the pGEX-MFA/TQS plasmid was transformed into the bacterial strain, BL21 Supercodon (Stratagene). The GST fusion protein is purified using glutathione agarose and used as immunogen in mice and rabbits to generate monoclonal antibodies and polyclonal antibodies.

EXAMPLE 6

Expression of Atr-2 in Mammalian Cells

In order to determine whether Atr-2 encoded a protein with kinase activity, a region containing the putative kinase domain was subcloned into the mammalian expression vector, pCIneo (Promega, Madison, Wis.). PCR was carried out using 2.5 µl Marathon® testis cDNA (Clontech), 1×cDNA polymerase buffer, 0.2 mM dNTPs, 1 µl Advantage® polymerase, and 100 ng each of primers atr2-STDF an atr2-3'KQS . Touchdown® PCR was carried out as described above. To add a FLAG® epitope tag, 1 µl of the resulting PCR reaction was used in a nested PCT using primer ATR2-TLRfor (SEQ ID NO: 39), which includes nucleotides encoding the FLAG® peptide sequences and ATR-2 specific nucleotides, and primer ATR2-KDrev (SEQ ID NO: 40).

selected colonies using primers ATR2TLRfor and ATR2KDrev in order to screen for the Atr2 insert.

Colonies were picked into 40 µl water and 5 µl of the resulting mixture was added to 20 µl of a PCR mixture containing 100 ng each primer, 0.2 mM dNTPs, 1×AmpliTaq® reaction buffer, 1.5 mM MgCl$_2$, and 1 U AmpliTaq® polymerase. Reaction conditions included an initial incubation at 94° C. for five min, followed by 30 cycles of 94° C. for 45 sec, 55° C. for 45 sec, 72° C. for 45 sec, a next step at 72° C. for 10 min, and a final holding step at 4° C. Reaction products were separated on an agarose gel.

Five reactions resulted in a band of the correct size and the sequence of the bands from two of these reactions was confirmed. One clone, A3, was determined to have the correct sequence and designated pCIneoFLAGATR2. This clone was transfected into 293T cells using Superfect® reagent (QIAGEN) according to the manufacturer's suggested protocol. Cells were harvested at 48 hr following transfection and lysed in 0.25 ml of lysis buffer containing 20 mM HEPES, pH 7.5, 1 mM Na$_3$VO$_4$, 5 mM NaF, 25 mM β-glycerophosphate, 2 mM EGTA, 2 mM EDTA, 0.5% Triton® X-100, 1 mM DDT and 1 tablet protease inhibitor cocktail (Boehringer Mannheim) for each 10 ml of lysis buffer. Cell lysates were immunoprecipitated using 1 µg anti-FLAG® M2 antibody (Sigma) for 2 hr at 4° C. Twenty µl protein A beads (Pierce) were incubated with the lysate-antibody mixture for an additional 2 hr at 4° C. The beads were washes twice with lysis buffer, followed by three washed in PBS. To confirm expression of the FLAG®-tagged Atr-2 protein, one third of the immunoprecipitation was separated on a Novex gel. Proteins were transferred to a PVDF membrane and the membrane was blocked in 5% milk/TBS/0.5% Tween-20 for one hr at room temperature. The membrane was incubated first with the anti-FLAG® M2 antibody and then with a secondary anti-mouse IgG-horse radish peroxidase (HRP) conjugated antibody. (Santa Cruz Biotechnology SC-2005). The membrane was washed three times in TBS with 0.05% Tween-20 and enhanced chemiluminescence reagents (New England Nuclear) identified a proteins with the expected size of 73 kDa.

Full length and truncated versions of Atr-2 is expressed in a baculovirus vector in SF9 insect cells. The coding region of Atr-2 contained within pCIneo FLAGAtr-2 was reconstructed into baculovirus vectors. To construct a plasmid that expressed recombinant Atr-2 in baculovirus, pCIneoFLA-GATR2 was digested with BamHI and SalI, and pFastBac (Gibco BRL) previously digested with the same two

```
ATR2-TLRfor  CTAGCTAGCGGATCCGAATCACACAGCTCACCACCATGGACT-    SEQ ID NO:39
             ATAAAGATGACGATGACAAGGGAACATTGCTGCGGTTGCTC ATR2-KDrev   GCGTGTCAGACTCATCCTGCTGTCCAGTCCACCAG            SEQ ID NO:40
```

The nested PCR was carried in a 50 µl reaction with AmpliTaq® polymerase (Perkin Elmer) under the following condition: 94° C. for 5 min, followed by 25 cycles of 94° C. for 30 sec, 55° C. for 30 sec, 72° C. for 30 sec, a final step of 72° C. for 7 min, and a final holding step at 4° C. The amplification products were separated using a low melting point agarose gel and a band of 2034 bp was isolated and purified using a QIAquick® extraction kit (QIAGEN). The fragment was digested with NheI and SalI and ligated into the mammalian expression vector pCIneo previously digested with the same two enzymes. The ligation reaction was transformed into E. coli strain XL1 blue (Stratagene) and the cells were plated. PCR was carried out on 30 enzymes. The resulting expression construct was transformed into the bacterial strain, XL1 Blue (Stratagene). The resulting plasmid is recombined into a hybrid plasmid-baculovirus, called a bacmid, in bacteria and transfected into the insect cell line, SF9. Once expressed in insect cells, a monoclonal antibody that recognizes the FLAG® tag (Eastman Kodak) is used to purify large quantities of the FLAG®-Atr-2 fusion protein. Activity of the protein is assayed as follows.

Infected insect cells are harvested 24–48 hours post-infection and lysed in lysis buffer (see above). Expressed FLAG®-Atr-2 fusion protein is purified using a column containing anti-FLAG® M2 affinity resin (Sigma). The column is washed with 20 column volumes of lysis buffer and then with 5 column volumes of 0.5 M lithium chloride, 50 mM Tris, pH 7.6, and 1 mM DTT. The column is eluted with either 0.1 M glycine, pH 3.0, followed by neutralization, or by competitive elution with the FLAG® peptide. The activity of the kinase is determined by performing a kinase assay.

Purified protein is incubated in optimal buffer conditions such as, 10 mM Hepes, pH 7.4, 10 mM $MnCl_2$, 50 mM NaCl, 10 mM $MgCl_2$, and 0.5 mM DTT. The reaction is carried out in the presence or absence of an exogenous substrate, such as lipid or peptide, along with 5 µCi γ-$^{32}$P-ATP (4 Ci/mM) for 10 minutes at 30° C.

The enzymatic assay is also used to screen for potential inhibitor or activator compounds. Small molecule chemical libraries, peptide and peptide mimetics, defined chemical entities, oligonucleotides, and natural product libraries (as described herein) are screened for modulators of kinase activity.

EXAMPLE 7

ATR-2 Kinase Activity

In order determine if the Atr-2 fragment subcloned in Example 6 possessed kinase activity, 293T cells were transfected with the pCIneoFLAGATR2 expression construct (Example 6) using Superfect® (QIAGEN). After 48 hr, cells were harvested and lysed in 0.5 ml lysis buffer (Example 6), and the lysates were precleared by incubation with 50 µl protein A beads for 2 hr at 4° C. The supernatant was immunoprecipitated with 6 µg anti-M2 antibody for one hr at 4° C. and the sample was divided into five aliquots. One hundred µl of the mixture was combined with 10 µl protein A beads for three hr at 4° C., after which the beads were washed twice with lysis buffer and three times in kinase buffer containing 10 mM HEPES, pH 7.4, 10 mM $MnCl_2$, 50 mM NaCl, 10 mM $MgCl_2$, and 5 mM DTT.

In the kinase assay, 10 µl protein A beads was mixed with 10 µl PKA and PKC inhibitors from a p79$^{S6}$ kinase assay kit (Upstate Biotechnology Inc., Lake Placid, N.Y.) and 10 µl ATP mixture: containing kinase buffer (above) with 10 mM ATP, 3 µCi $^{32}$P-ATP, plus or minus 6 µl myelin basic protein as substrate. Reactions were incubated at 30° C. for 30 min and 20 µl of the reaction mixture was spotted onto P81 paper. The P81 paper was washed three times in 150 mM phosphoric acid and dried, and Cerenkov radiation measured.

The results demonstrated that the 73 kDa Atr-2 truncated protein encoded kinase activity that was able to phosphorylate the Atr-2 protein itself and the exogenous myelin basic protein substrate. Further, the Atr-2 kinase did not phosphorylate PHAS-1 or histone H1, suggesting substrate specificity for the kinase.

Numerous modifications and variations in the invention as set forth in the above illustrative examples are expected to occur to those skilled in the art. Consequently only such limitations as appear in the appended claims should be placed on the invention.

What is claimed is:

1. A purified and isolated mature Atr-2 polypeptide comprising the amino acid sequence set out in SEQ ID NO: 2.

2. A purified and isolated mature Atr-2 polypeptide encoded by a polynucleotide comprising the sequence set out in SEQ ID NO: 1.

3. A purified and isolated Atr-2 polypeptide with kinase activity encoded by a polynucleotide selected from the group consisting of a) the polynucleotide set out in SEQ ID NO:1;

b) a polynucleotide encoding the polypeptide encoded by the polynucleotide of (a); and c) polynucleotides that hybridizes to the complete complement of the polynucleotide of (a) or (b) under moderately stringent conditions, said conditions including a final wash in 2× to 3×SSC/0.1% SDS at 65° C. to 75° C.

* * * * *

UNITED STATES PATENT AND TRADEMARK OFFICE
CERTIFICATE OF CORRECTION

PATENT NO. : 6,815,532 B2
DATED : November 9, 2004
INVENTOR(S) : Kate Loughney et al.

It is certified that error appears in the above-identified patent and that said Letters Patent is hereby corrected as shown below:

Column 1,
Line 18, please delete "Tetrapeptide]" and insert -- Tetrapeptide$^1$ --.

Column 2,
Line 7, please delete "Immubilized" and insert -- Immobilized --.

Column 11,
Line 50, please delete "contemplated" and insert -- contemplated, --.

Column 13,
Line 12, please delete "NQ" and insert -- N Q --.

Column 14,
Line 7, please delete "Gin" and insert -- Gin, --.

Column 15,
Line 43, please delete "or the DNA" and insert -- of the DNA --.

Column 19,
Lines 44-45, please delete "nucleotide" and insert -- nucleotides --.

Column 20,
Line 52, please delete "25-20" and insert -- 25-30 --.
Line 60, please delete "mutatnt" and insert -- mutant --.

Column 23,
Line 2, please delete "form or Atr-2" and insert -- form of Atr-2 --.
Line 12, please delete "P13" and insert -- PI3 --.
Line 16, please delete "X83368)." and insert -- X83368), --.

Column 24,
Line 43, please delete "AI1050717" and insert -- AI050717 --.

Column 25,
Line 44, please delete "rediesigned" and insert -- redesigned --.

Column 27,
Line 39, please delete "22F157" and insert -- 22F/57 --.
Line 62-63, please delete "PCR with performed" and insert -- PCR was performed --.

UNITED STATES PATENT AND TRADEMARK OFFICE
CERTIFICATE OF CORRECTION

PATENT NO. : 6,815,532 B2
DATED : November 9, 2004
INVENTOR(S) : Kate Loughney et al.

It is certified that error appears in the above-identified patent and that said Letters Patent is hereby corrected as shown below:

Column 28,
Line 24, please delete "$\lambda/1$" and insert -- $\lambda/_1$ --

Column 29,
Line 64, please delete "hand" and insert -- band --.

Column 30,
Line 51, please delete "kb" and insert -- kb. --.

Column 31,
Line 27, please delete "GTTC" and insert -- GTTG --.
Line 29, please delete "Marathon" and insert -- Marathon® --.
Line 30, please delete "buffer." and insert -- buffer, --.
Line 57, please delete "ekpected" and insert -- expected --.

Column 32,
Line 66, please delete "bock" and insert -- block --.

Column 34,
Line 3, please delete "tp" and insert -- to --.
Line 40, please delete "kinases" and insert -- kinases. --.

Column 35,
Line 18, please delete "TOPIOF" and insert -- TOP1OF' --.

Column 36,
Line 28, please delete "washes" and insert -- washed --.
Line 29, please delete "washed" and insert -- washes --.
Line 40, please delete "proteins" and insert -- protein --.
Lines 43 and 45, please delete "pClneo" and insert -- pCIneo --.

Column 38,
Line 13, please delete "mixture:" and insert -- mixture --.

UNITED STATES PATENT AND TRADEMARK OFFICE
CERTIFICATE OF CORRECTION

PATENT NO. : 6,815,532 B2
DATED : November 9, 2004
INVENTOR(S) : Kate Loughney et al.

It is certified that error appears in the above-identified patent and that said Letters Patent is hereby corrected as shown below:

Column 110,
Line 24, please delete "hybridizes" and insert -- hybridize --.

Signed and Sealed this

Seventeenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,815,532 B1
DATED : November 9, 2004
INVENTOR(S) : Kate Loughney et al.

It is certified that error appears in the above-identified patent and that said Letters Patent is hereby corrected as shown below:

Title page, Item [54] and Column 1, line 2,
Title, "IL-1RA FC" should be -- IL-1Ra Fc --, Title page,
Item [75], Inventors, "Moorpark" should be -- Thousand Oaks --,
Item [56], References Cited, OTHER PUBLICATIONS, "Prieur et al." reference, "juvenille" should be -- juvenile --, Column 3,
Line 41, "amnidated' should be -- amidated --, Column 5,
Line 18, "5 sequence" should be -- sequence --,
Line 24, "residues 10" should be -- residues --, Column 6,
Line 62, "agnostic' should be -- agonistic --, Column 7,
Line 1, "OPC" should be -- OPG --, Column 8,
Line 6, "WO 9 15 96/23067" should be -- WO 96/23067 --,
Line 11, "a interleukin" should be -- interleukin --,
Line 35, "nirmetic" should be -- mimetic --,
Line 37, "1696-10 9," should be -- 1696-9, --,
Line 56, "hydrobromide;" should be -- hydrobromide; --, Column 9,
Line 7, "Land" should be -- L1 and --,
Line 23, "F'is" should be -- F' is --,
Line 32, "GCSF" should be -- G-CSF --,
Line 42, "15 any site" should be -- any site --, Column 10,
Line 44, "4and5." should be -- 4 and 5. --, Column 11,
Line 28, "(Gly)," should be -- (Gly)4, --,
Line 33, "(CH2)5" should be -- (CH2)s --,
Line 36, "(e.g., C, Cj" should be -- (e.g., C1-C6) --,

UNITED STATES PATENT AND TRADEMARK OFFICE
CERTIFICATE OF CORRECTION

PATENT NO. : 6,815,532 B1
DATED : November 9, 2004
INVENTOR(S) : Kate Loughney et al.

It is certified that error appears in the above-identified patent and that said Letters Patent is hereby corrected as shown below:

Column 11 (cont'd),
Line 36, "NH2" should be -- NH2 --,
Line 52, "Such L:L derivatives" should be -- Such derivatives --,
Line 53, "and A; 15 the like of" should be -- and the like of --, Column 12,
Line 50, 10 succinic" should be –succinic--,
Lines 53-54, "picolinimnidate;" should be -- picolinimidate; --, Column 13,
Line 3, "N-acetylirmidizole" should be -- N-acetylimidizole --,
Line 7, "carbodimi des" should be -- carbodilmides --,
Line 13, "Glutarinyl" should be -- Glutaminyl --,
Line 24, "cross-lining" should be -- cross-linking --.
Line 26, "N-hydroxysuccinimnide" should be -- N-hydroxysuccinimide --,
Line 29, "(succimnidylpropionate)," should be -- (succinimidyipropionate), --, Column 15,
Line 44, "Tris-HCI" should be -- Tris-HCI --,
Line 46, "TWEEDTM" should be -- TWEENTM --, Column 16,
Line 4, "(endothelin-2 0 1);" should be -- (endothelin-1); --,
Line 7, "(al-proteinase);" should be -- (αl-proteinase); --,
Line 9, "Delivery II. (indent) Keystone, Colo .° should be -- Delivery II, Keystone, Colo. --,
Line 21, "nebuizer; should be -- nebulizer, --.
Line 22, "Colo." should be -- Colo.; --,
Line 24, "N.C" should be -- N.C.: --, Column 17,
Line 53, "FcOsteoprotegrin" should be -- Fc-Osteoprotegrin --,
Line 59, "ammnonium" should be -- ammonium --, Column 18,
Line 23, "CuCl2," should be -- CuCI2, --,
Line 24, "CuCl2," should be -- CuCI2 --,
Line 48, "60 ° C" should be -- 60°C. --,
Line 51, "APIGO" should be -- AP100 --,
Line 54, "1OmM" should be -- 10mM --,
Lines 55-56, "50 m M CuCl, (final pH 4)." should be -- 50 mM CuCl2, (final pH~4). --,

UNITED STATES PATENT AND TRADEMARK OFFICE
CERTIFICATE OF CORRECTION

PATENT NO.    : 6,815,532 B1
DATED         : November 9, 2004
INVENTOR(S)   : Kate Loughney et al.

It is certified that error appears in the above-identified patent and that said Letters Patent is hereby corrected as shown below:

Column 18 (cont'd),
Line 58, "HCI" should be -- MCI --,
Line 59, "1$\mu$L" should be -- $\mu$L --,
Line 60, "(10 my)" should be -- (10 mM) --,
Line 66, "GdHCI" should be -- GdHCI --,
Lines 66-67, "37°C" should be -- 37° C. --, Column 19,
Line 1, "Discussion Cyanylation" should be -- Discussion (Indent and begin new paragraph) Cyanylation --,
Line 9, "no-longer" should be -- no longer --,
Line 9, "CuC1." should be -- CuCl2. --,
Line 11, "CuCL" should be -- CuCl2 --,
Lines 38 and 54, "Fc OPG" should be -- Fc-OPG --, Column 20,
Lines 8, 20 and 22, "Fc OPG" should be -- Fc-OPG --,
Line 12, "B1/min" should be -- B/min --,
Line 14, "Bimin" should be -- B/min --,
Line 15, "60° C" should be -- 60° C. --,
Line 19, "29 DC" should be -- 29° C. --,
Line 20, "CuC2" should be -- CuCl2 --,
Line 37, "urless" should be -- unless --, Column 25,
Line 20, "domain" should be -- domain; --, Column 26,
Line 16, "CuCIl2." should be -- CuCl2. --,

UNITED STATES PATENT AND TRADEMARK OFFICE
CERTIFICATE OF CORRECTION

PATENT NO. : 6,815,532 B1
DATED : November 9, 2004
INVENTOR(S) : Kate Loughney et al.

It is certified that error appears in the above-identified patent and that said Letters Patent is hereby corrected as shown below:

Column 26 (cont'd),
Line 17, "dormain" should be -- domain --,

Signed and Sealed this

Twenty-eighth Day of June, 2005

JON W. DUDAS
*Director of the United States Patent and Trademark Office*

SEQUENCE LISTING

<160> NUMBER OF SEQ ID NOS: 43

<210> SEQ ID NO 1
<211> LENGTH: 8838
<212> TYPE: DNA
<213> ORGANISM: Homo sapiens
<220> FEATURE:
<221> NAME/KEY: CDS
<222> LOCATION: (31)..(8820)
<223> OTHER INFORMATION:

<400> SEQUENCE: 1

```
ggacacgagg aaactgttaa tgacttgggc atg act tgg gct ttg gaa gca gct         54
                                 Met Thr Trp Ala Leu Glu Ala Ala
                                  1               5 gtt tta atg aag aag tct gaa aca tac gca cct tta ttc tct ctt ccg         102
Val Leu Met Lys Lys Ser Glu Thr Tyr Ala Pro Leu Phe Ser Leu Pro
    10                  15                  20 tct ttc cat aaa ttt tgc aaa ggc ctt tta gcc aac act ctc gtt gaa         150
Ser Phe His Lys Phe Cys Lys Gly Leu Leu Ala Asn Thr Leu Val Glu
25                  30                  35                  40 gat gtg aat atc tgt ctg cag gca tgc agc agt cta cat gct ctg tcc         198
Asp Val Asn Ile Cys Leu Gln Ala Cys Ser Ser Leu His Ala Leu Ser
                    45                  50                  55 tct tcc ttg cca gat gat ctt tta cag aga tgt gtc gat gtt tgc cgt         246
Ser Ser Leu Pro Asp Asp Leu Leu Gln Arg Cys Val Asp Val Cys Arg
                60                  65                  70 gtt caa cta gtg cac agt gga act cgt att cga caa gca ttt gga aaa         294
Val Gln Leu Val His Ser Gly Thr Arg Ile Arg Gln Ala Phe Gly Lys
            75                  80                  85 ctg ttg aaa tca att cct tta gat gtt gtc cta agc aat aac aat cac         342
```

-continued

| | | |
|---|---|---|
| Leu Leu Lys Ser Ile Pro Leu Asp Val Val Leu Ser Asn Asn Asn His<br>      90                        95                            100 | | |
| aca gaa att caa gaa att tct tta gca tta aga agt cac atg agt aaa<br>Thr Glu Ile Gln Glu Ile Ser Leu Ala Leu Arg Ser His Met Ser Lys<br>105                     110                  115                  120 | | 390 |
| gca cca agt aat aca ttc cac ccc caa gat ttc tct gat gtt att agt<br>Ala Pro Ser Asn Thr Phe His Pro Gln Asp Phe Ser Asp Val Ile Ser<br>                        125                  130                  135 | | 438 |
| ttt att ttg tat ggg aac tct cat aga aca ggg aag gac aat tgg ttg<br>Phe Ile Leu Tyr Gly Asn Ser His Arg Thr Gly Lys Asp Asn Trp Leu<br>                  140                  145                  150 | | 486 |
| gaa aga ctg ttc tat agc tgc cag aga ctg gat aag cgt gac cag tca<br>Glu Arg Leu Phe Tyr Ser Cys Gln Arg Leu Asp Lys Arg Asp Gln Ser<br>          155                  160                  165 | | 534 |
| aca att cca cgc aat ctc ctg aag aca gat gct gtc ctt tgg cag tgg<br>Thr Ile Pro Arg Asn Leu Leu Lys Thr Asp Ala Val Leu Trp Gln Trp<br>          170                  175                  180 | | 582 |
| gcc ata tgg gaa gct gca caa ttc act gtt ctt tct aag ctg aga acc<br>Ala Ile Trp Glu Ala Ala Gln Phe Thr Val Leu Ser Lys Leu Arg Thr<br>185                     190                  195                  200 | | 630 |
| cca ctg ggc aga gct caa gac acc ttc cag aca att gaa ggt atc att<br>Pro Leu Gly Arg Ala Gln Asp Thr Phe Gln Thr Ile Glu Gly Ile Ile<br>                        205                  210                  215 | | 678 |
| cga agt ctc gca gct cac aca tta aac cct gat cag gat gtt agt cag<br>Arg Ser Leu Ala Ala His Thr Leu Asn Pro Asp Gln Asp Val Ser Gln<br>                  220                  225                  230 | | 726 |
| tgg aca act gca gac aat gat gaa ggc cat ggt aac aac caa ctt aga<br>Trp Thr Thr Ala Asp Asn Asp Glu Gly His Gly Asn Asn Gln Leu Arg<br>          235                  240                  245 | | 774 |
| ctt gtt ctt ctt ctg cag tat ctg gaa aat ctg gag aaa tta atg tat<br>Leu Val Leu Leu Leu Gln Tyr Leu Glu Asn Leu Glu Lys Leu Met Tyr<br>          250                  255                  260 | | 822 |
| aat gca tac gag gga tgt gct aat gca tta act tca cct ccc aag gtc<br>Asn Ala Tyr Glu Gly Cys Ala Asn Ala Leu Thr Ser Pro Pro Lys Val<br>265                     270                  275                  280 | | 870 |
| att aga act ttt ttc tat acc aat cgc caa act tgt cag gac tgg cta<br>Ile Arg Thr Phe Phe Tyr Thr Asn Arg Gln Thr Cys Gln Asp Trp Leu<br>                        285                  290                  295 | | 918 |
| acg cgg att cga ctc tcc atc atg agg gta gga ttg ttg gca ggc cag<br>Thr Arg Ile Arg Leu Ser Ile Met Arg Val Gly Leu Leu Ala Gly Gln<br>                  300                  305                  310 | | 966 |
| cct gca gtg aca gtg aga cat ggc ttt gac ttg ctt aca gag atg aaa<br>Pro Ala Val Thr Val Arg His Gly Phe Asp Leu Leu Thr Glu Met Lys<br>          315                  320                  325 | | 1014 |
| aca acc agc cta tct cag ggg aat gaa ttg gaa gta acc att atg atg<br>Thr Thr Ser Leu Ser Gln Gly Asn Glu Leu Glu Val Thr Ile Met Met<br>          330                  335                  340 | | 1062 |
| gtg gta gaa gca tta tgt gaa ctt cat tgt cct gaa gct ata cag gga<br>Val Val Glu Ala Leu Cys Glu Leu His Cys Pro Glu Ala Ile Gln Gly<br>345                     350                  355                  360 | | 1110 |
| att gct gtc tgg tca tca tct att gtt gga aaa aat ctt ctg tgg att<br>Ile Ala Val Trp Ser Ser Ser Ile Val Gly Lys Asn Leu Leu Trp Ile<br>                  365                  370                  375 | | 1158 |
| aac tca gtg gct caa cag gct gaa ggg agg ttt gaa aag gcc tct gtg<br>Asn Ser Val Ala Gln Gln Ala Glu Gly Arg Phe Glu Lys Ala Ser Val<br>                  380                  385                  390 | | 1206 |
| gag tac cag gaa cac ctg tgt gcc atg aca ggt gtt gat tgc tgc atc<br>Glu Tyr Gln Glu His Leu Cys Ala Met Thr Gly Val Asp Cys Cys Ile<br>          395                  400                  405 | | 1254 |

```
tcc agc ttt gac aaa tcg gtg ctc acc tta gcc aat gct ggg cgt aac      1302
Ser Ser Phe Asp Lys Ser Val Leu Thr Leu Ala Asn Ala Gly Arg Asn
    410             415                 420 agt gcc agc ccg aaa cat tct ctg aat ggt gaa tcc aga aaa act gtg      1350
Ser Ala Ser Pro Lys His Ser Leu Asn Gly Glu Ser Arg Lys Thr Val
425             430                 435                 440 ctg tcc aaa ccg act gac tct tcc cct gag gtt ata aat tat tta gga      1398
Leu Ser Lys Pro Thr Asp Ser Ser Pro Glu Val Ile Asn Tyr Leu Gly
                445                 450                 455 aat aaa gca tgt gag tgc tac atc tca att gcc gat tgg gct gct gtg      1446
Asn Lys Ala Cys Glu Cys Tyr Ile Ser Ile Ala Asp Trp Ala Ala Val
            460                 465                 470 cag gaa tgg cag aac gct atc cat gac ttg aaa aag agt acc agt agc      1494
Gln Glu Trp Gln Asn Ala Ile His Asp Leu Lys Lys Ser Thr Ser Ser
        475                 480                 485 act tcc ctc aac ctg aaa gct gac ttc aac tat ata aaa tca tta agc      1542
Thr Ser Leu Asn Leu Lys Ala Asp Phe Asn Tyr Ile Lys Ser Leu Ser
    490                 495                 500 agc ttt gag tct gga aaa ttt gtt gaa tgt acc gag cag tta gaa ttg      1590
Ser Phe Glu Ser Gly Lys Phe Val Glu Cys Thr Glu Gln Leu Glu Leu
505                 510                 515                 520 tta cca gga gaa aat atc aat cta ctt gct gga gga tca aaa gaa aaa      1638
Leu Pro Gly Glu Asn Ile Asn Leu Leu Ala Gly Gly Ser Lys Glu Lys
                525                 530                 535 ata gac atg aaa aaa ctg ctt cct aac atg tta agt ccg gat ccg agg      1686
Ile Asp Met Lys Lys Leu Leu Pro Asn Met Leu Ser Pro Asp Pro Arg
            540                 545                 550 gaa ctt cag aaa tcc att gaa gtt caa ttg tta aga agt tct gtt tgt      1734
Glu Leu Gln Lys Ser Ile Glu Val Gln Leu Leu Arg Ser Ser Val Cys
        555                 560                 565 ttg gca act gct tta aac ccg ata gaa caa gat cag aag tgg cag tct      1782
Leu Ala Thr Ala Leu Asn Pro Ile Glu Gln Asp Gln Lys Trp Gln Ser
    570                 575                 580 ata act gaa aat gtg gta aag tac ttg aag caa aca tcc cgc atc gct      1830
Ile Thr Glu Asn Val Val Lys Tyr Leu Lys Gln Thr Ser Arg Ile Ala
585                 590                 595                 600 att gga cct ctg aga ctt tct act tta aca gtt tca cag tct ttg cca      1878
Ile Gly Pro Leu Arg Leu Ser Thr Leu Thr Val Ser Gln Ser Leu Pro
                605                 610                 615 gtt cta agt acc ttg cag ctg tat tgc tca tct gct ttg gag aac aca      1926
Val Leu Ser Thr Leu Gln Leu Tyr Cys Ser Ser Ala Leu Glu Asn Thr
            620                 625                 630 gtt tct aac aga ctt tca aca gag gac tgt ctt att cca ctc ttc agt      1974
Val Ser Asn Arg Leu Ser Thr Glu Asp Cys Leu Ile Pro Leu Phe Ser
        635                 640                 645 gaa gct tta cgt tca tgt aaa cag cat gac gtg agg cca tgg atg cag      2022
Glu Ala Leu Arg Ser Cys Lys Gln His Asp Val Arg Pro Trp Met Gln
    650                 655                 660 gca tta agg tat act atg tac cag aat cag ttg ttg gag aaa att aaa      2070
Ala Leu Arg Tyr Thr Met Tyr Gln Asn Gln Leu Leu Glu Lys Ile Lys
665                 670                 675                 680 gaa caa aca gtc cca att aga agc cat ctc atg gaa tta ggt cta aca      2118
Glu Gln Thr Val Pro Ile Arg Ser His Leu Met Glu Leu Gly Leu Thr
                685                 690                 695 gca gca aaa ttt gct aga aaa cga ggg aat gtg tcc ctt gca aca aga      2166
Ala Ala Lys Phe Ala Arg Lys Arg Gly Asn Val Ser Leu Ala Thr Arg
            700                 705                 710 ctg ctg gca cag tgc agt gaa gtt cag ctg gga aag acc acc act gca      2214
Leu Leu Ala Gln Cys Ser Glu Val Gln Leu Gly Lys Thr Thr Thr Ala
        715                 720                 725
```

-continued

```
cag gat tta gtc caa cat ttt aaa aaa cta tca acc caa ggt caa gtg    2262
Gln Asp Leu Val Gln His Phe Lys Lys Leu Ser Thr Gln Gly Gln Val
    730                 735                 740 gat gaa aaa tgg ggg ccc gaa ctt gat att gaa aaa acc aaa ttg ctt    2310
Asp Glu Lys Trp Gly Pro Glu Leu Asp Ile Glu Lys Thr Lys Leu Leu
745                 750                 755                 760 tat aca gca ggc cag tca aca cat gca atg gaa atg ttg agt tct tgt    2358
Tyr Thr Ala Gly Gln Ser Thr His Ala Met Glu Met Leu Ser Ser Cys
                765                 770                 775 gcc ata tct ttc tgc aag tct gtg aaa gct gaa tat gca gtt gct aaa    2406
Ala Ile Ser Phe Cys Lys Ser Val Lys Ala Glu Tyr Ala Val Ala Lys
            780                 785                 790 tca att ctg aca ctg gct aaa tgg atc cag gca gaa tgg aaa gag att    2454
Ser Ile Leu Thr Leu Ala Lys Trp Ile Gln Ala Glu Trp Lys Glu Ile
        795                 800                 805 tca gga cag ctg aaa cag gtt tac aga gct cag cac caa cag aac ttc    2502
Ser Gly Gln Leu Lys Gln Val Tyr Arg Ala Gln His Gln Gln Asn Phe
    810                 815                 820 aca ggt ctt tct act ttg tct aaa aac ata ctc act cta ata gaa ctg    2550
Thr Gly Leu Ser Thr Leu Ser Lys Asn Ile Leu Thr Leu Ile Glu Leu
825                 830                 835                 840 cca tct gtt aat acg atg gaa gaa gag tat cct cgg atc gag agt gaa    2598
Pro Ser Val Asn Thr Met Glu Glu Glu Tyr Pro Arg Ile Glu Ser Glu
                845                 850                 855 tct aca gtg cat att gga gtt gga gaa cct gac ttc att ttg gga cag    2646
Ser Thr Val His Ile Gly Val Gly Glu Pro Asp Phe Ile Leu Gly Gln
            860                 865                 870 ttg tat cac ctg tct tca gta cag gca cct gaa gta gcc aaa tct tgg    2694
Leu Tyr His Leu Ser Ser Val Gln Ala Pro Glu Val Ala Lys Ser Trp
        875                 880                 885 gca gcg ttg gcc agc tgg gct tat agg tgg ggc aga aag gtg gtt gac    2742
Ala Ala Leu Ala Ser Trp Ala Tyr Arg Trp Gly Arg Lys Val Val Asp
    890                 895                 900 aat gcc agt cag gga gaa ggt gtt cgt ctg ctg cct aga gaa aaa tct    2790
Asn Ala Ser Gln Gly Glu Gly Val Arg Leu Leu Pro Arg Glu Lys Ser
905                 910                 915                 920 gaa gtt cag aat cta ctt cca gac act ata act gag gaa gag aaa gag    2838
Glu Val Gln Asn Leu Leu Pro Asp Thr Ile Thr Glu Glu Glu Lys Glu
                925                 930                 935 aga ata tat ggt att ctt gga cag gct gtg tgt cgg ccg gcg ggg att    2886
Arg Ile Tyr Gly Ile Leu Gly Gln Ala Val Cys Arg Pro Ala Gly Ile
            940                 945                 950 cag gat gaa gat ata aca ctt cag ata act gag agt gaa gac aac gaa    2934
Gln Asp Glu Asp Ile Thr Leu Gln Ile Thr Glu Ser Glu Asp Asn Glu
        955                 960                 965 gaa gat gac atg gtt gat gtt atc tgg cgt cag ttg ata tca agc tgc    2982
Glu Asp Asp Met Val Asp Val Ile Trp Arg Gln Leu Ile Ser Ser Cys
    970                 975                 980 cca tgg ctt tca gaa ctt gat gaa agt gca act gaa gga gtt att aaa    3030
Pro Trp Leu Ser Glu Leu Asp Glu Ser Ala Thr Glu Gly Val Ile Lys
985                 990                 995                 1000 gtg tgg agg aaa gtt gta gat aga ata ttc agc ctg tac aaa ctc       3075
Val Trp Arg Lys Val Val Asp Arg Ile Phe Ser Leu Tyr Lys Leu
                1005                1010                1015 tct tgc agt gca tac ttt act ttc ctt aaa ctc aac gct ggt caa       3120
Ser Cys Ser Ala Tyr Phe Thr Phe Leu Lys Leu Asn Ala Gly Gln
                1020                1025                1030 att cct tta gat gag gat gac cct agg ctg cat tta agt cac aga       3165
Ile Pro Leu Asp Glu Asp Asp Pro Arg Leu His Leu Ser His Arg
```

```
                             1035                    1040                    1045
         gtg gaa cag agc act gat gac atg att gtg atg gcc aca ttg cgc          3210
         Val Glu Gln Ser Thr Asp Asp Met Ile Val Met Ala Thr Leu Arg
                         1050                    1055                    1060 ctg ctg cgg ttg ctc gtg aag cac gct ggt gag ctt cgg cag tat          3255
         Leu Leu Arg Leu Leu Val Lys His Ala Gly Glu Leu Arg Gln Tyr
                         1065                    1070                    1075 ctg gag cac ggc ttg gag aca aca ccc act gca cca tgg aga gga          3300
         Leu Glu His Gly Leu Glu Thr Thr Pro Thr Ala Pro Trp Arg Gly
                         1080                    1085                    1090 att att ccg caa ctt ttc tca cgc tta aac cac cct gaa gtg tat          3345
         Ile Ile Pro Gln Leu Phe Ser Arg Leu Asn His Pro Glu Val Tyr
                         1095                    1100                    1105 gtg cgc caa agt att tgt aac ctt ctc tgc cgt gtg gct caa gat          3390
         Val Arg Gln Ser Ile Cys Asn Leu Leu Cys Arg Val Ala Gln Asp
                         1110                    1115                    1120 tcc cca cat ctc ata ttg tat cct gca ata gtg ggt acc ata tcg          3435
         Ser Pro His Leu Ile Leu Tyr Pro Ala Ile Val Gly Thr Ile Ser
                         1125                    1130                    1135 ctt agt agt gaa tcc cag gct tca gga aat aaa ttt tcc act gca          3480
         Leu Ser Ser Glu Ser Gln Ala Ser Gly Asn Lys Phe Ser Thr Ala
                         1140                    1145                    1150 att cca act tta ctt ggc aat att caa gga gaa gaa ttg ctg gtt          3525
         Ile Pro Thr Leu Leu Gly Asn Ile Gln Gly Glu Glu Leu Leu Val
                         1155                    1160                    1165 tct gaa tgt gag gga gga agt cct cct gca tct cag gat agc aat          3570
         Ser Glu Cys Glu Gly Gly Ser Pro Pro Ala Ser Gln Asp Ser Asn
                         1170                    1175                    1180 aag gat gaa cct aaa agt gga tta aat gaa gac caa gcc atg atg          3615
         Lys Asp Glu Pro Lys Ser Gly Leu Asn Glu Asp Gln Ala Met Met
                         1185                    1190                    1195 cag gat tgt tac agc aaa att gta gat aag ctg tcc tct gca aac          3660
         Gln Asp Cys Tyr Ser Lys Ile Val Asp Lys Leu Ser Ser Ala Asn
                         1200                    1205                    1210 ccc acc atg gta tta cag gtt cag atg ctc gtg gct gaa ctg cgc          3705
         Pro Thr Met Val Leu Gln Val Gln Met Leu Val Ala Glu Leu Arg
                         1215                    1220                    1225 agg gtc act gtg ctc tgg gat gag ctc tgg ctg gga gtt ttg ctg          3750
         Arg Val Thr Val Leu Trp Asp Glu Leu Trp Leu Gly Val Leu Leu
                         1230                    1235                    1240 caa caa cac atg tat gtc ctg aga cga att cag cag ctt gaa gat          3795
         Gln Gln His Met Tyr Val Leu Arg Arg Ile Gln Gln Leu Glu Asp
                         1245                    1250                    1255 gag gtg aag aga gtc cag aac aac aac acc tta cgc aaa gaa gag          3840
         Glu Val Lys Arg Val Gln Asn Asn Asn Thr Leu Arg Lys Glu Glu
                         1260                    1265                    1270 aaa att gca atc atg agg gag aag cac aca gct ttg atg aag ccc          3885
         Lys Ile Ala Ile Met Arg Glu Lys His Thr Ala Leu Met Lys Pro
                         1275                    1280                    1285 atc gta ttt gct ttg gag cat gtg agg agt atc aca gcg gct cct          3930
         Ile Val Phe Ala Leu Glu His Val Arg Ser Ile Thr Ala Ala Pro
                         1290                    1295                    1300 gca gaa aca cct cat gaa aaa tgg ttt cag gat aac tat ggt gat          3975
         Ala Glu Thr Pro His Glu Lys Trp Phe Gln Asp Asn Tyr Gly Asp
                         1305                    1310                    1315 gcc att gaa aat gcc cta gaa aaa ctg aag act cca ttg aac cct          4020
         Ala Ile Glu Asn Ala Leu Glu Lys Leu Lys Thr Pro Leu Asn Pro
                         1320                    1325                    1330 gca aag cct ggg agc agc tgg att cca ttt aaa gag ata atg cta          4065
```

```
Ala Lys Pro Gly Ser  Ser Trp Ile Pro Phe  Lys Glu Ile Met Leu
        1335                 1340                 1345 agt ttg caa cag aga  gca cag aaa cgt gca  agt tac atc ttg cgt         4110
Ser Leu Gln Gln Arg  Ala Gln Lys Arg Ala  Ser Tyr Ile Leu Arg
        1350                 1355                 1360 ctt gaa gaa atc agt  cca tgg ttg gct gcc  atg act aac act gaa         4155
Leu Glu Glu Ile Ser  Pro Trp Leu Ala Ala  Met Thr Asn Thr Glu
        1365                 1370                 1375 att gct ctt cct ggg  gaa gtc tca gcc aga  gac act gtc aca atc         4200
Ile Ala Leu Pro Gly  Glu Val Ser Ala Arg  Asp Thr Val Thr Ile
        1380                 1385                 1390 cat agt gtg ggc gga  acc atc aca atc tta  ccg act aaa acc aag         4245
His Ser Val Gly Gly  Thr Ile Thr Ile Leu  Pro Thr Lys Thr Lys
        1395                 1400                 1405 cca aag aaa ctt ctc  ttt ctt gga tca gat  ggg aag agc tat cct         4290
Pro Lys Lys Leu Leu  Phe Leu Gly Ser Asp  Gly Lys Ser Tyr Pro
        1410                 1415                 1420 tat ctt ttc aaa gga  ctg gag gat tta cat  ctg gat gag aga ata         4335
Tyr Leu Phe Lys Gly  Leu Glu Asp Leu His  Leu Asp Glu Arg Ile
        1425                 1430                 1435 atg cag ttc cta tct  att gtg aat acc atg  ttt gct aca att aat         4380
Met Gln Phe Leu Ser  Ile Val Asn Thr Met  Phe Ala Thr Ile Asn
        1440                 1445                 1450 cgc caa gaa aca ccc  cgg ttc cat gct cga  cac tat tct gta aca         4425
Arg Gln Glu Thr Pro  Arg Phe His Ala Arg  His Tyr Ser Val Thr
        1455                 1460                 1465 cca cta gga aca aga  tca gga cta atc cag  tgg gta gat gga gcc         4470
Pro Leu Gly Thr Arg  Ser Gly Leu Ile Gln  Trp Val Asp Gly Ala
        1470                 1475                 1480 aca ccc tta ttt ggt  ctt tac aaa cga tgg  caa caa cgg gaa gct         4515
Thr Pro Leu Phe Gly  Leu Tyr Lys Arg Trp  Gln Gln Arg Glu Ala
        1485                 1490                 1495 gcc tta caa gca caa  aag gcc caa gat tcc  tac caa act cct cag         4560
Ala Leu Gln Ala Gln  Lys Ala Gln Asp Ser  Tyr Gln Thr Pro Gln
        1500                 1505                 1510 aat cct gga att gta  ccc cgt cct agt gaa  ctt tat tac agt aaa         4605
Asn Pro Gly Ile Val  Pro Arg Pro Ser Glu  Leu Tyr Tyr Ser Lys
        1515                 1520                 1525 att ggc cct gct ttg  aaa aca gtt ggg ctt  agc ctg gat gtg tcc         4650
Ile Gly Pro Ala Leu  Lys Thr Val Gly Leu  Ser Leu Asp Val Ser
        1530                 1535                 1540 cgt cgg gat tgg cct  ctt cat gta atg aag  gca gta ttg gaa gag         4695
Arg Arg Asp Trp Pro  Leu His Val Met Lys  Ala Val Leu Glu Glu
        1545                 1550                 1555 tta atg gag gcc aca  ccc ccg aat ctc ctt  gcc aaa gag ctc tgg         4740
Leu Met Glu Ala Thr  Pro Pro Asn Leu Leu  Ala Lys Glu Leu Trp
        1560                 1565                 1570 tca tct tgc aca aca  cct gat gaa tgg tgg  aga gtt acg cag tct         4785
Ser Ser Cys Thr Thr  Pro Asp Glu Trp Trp  Arg Val Thr Gln Ser
        1575                 1580                 1585 tat gca aga tct act  gca gtc atg tct atg  gtt gga tac ata att         4830
Tyr Ala Arg Ser Thr  Ala Val Met Ser Met  Val Gly Tyr Ile Ile
        1590                 1595                 1600 ggc ctt gga gac aga  cat ctg gat aat gtt  ctt ata gat atg acg         4875
Gly Leu Gly Asp Arg  His Leu Asp Asn Val  Leu Ile Asp Met Thr
        1605                 1610                 1615 act gga gaa gtt gtt  cac ata gat tac aat  gtt tgc ttt gaa aaa         4920
Thr Gly Glu Val Val  His Ile Asp Tyr Asn  Val Cys Phe Glu Lys
        1620                 1625                 1630
```

| | | |
|---|---|---|
| ggt aaa agc ctt aga gtt cct gag aaa gta cct ttt cga atg aca<br>Gly Lys Ser Leu Arg Val Pro Glu Lys Val Pro Phe Arg Met Thr<br>　　　　　　　1635　　　　　　　　　　1640　　　　　　　　　　1645 | | 4965 |
| caa aac att gaa aca gca ctg ggt gta act gga gta gaa ggt gta<br>Gln Asn Ile Glu Thr Ala Leu Gly Val Thr Gly Val Glu Gly Val<br>　　　　　　　1650　　　　　　　　　　1655　　　　　　　　　　1660 | | 5010 |
| ttt agg ctt tca tgt gag cag gtt tta cac att atg cgg cgt ggc<br>Phe Arg Leu Ser Cys Glu Gln Val Leu His Ile Met Arg Arg Gly<br>　　　　　　　1665　　　　　　　　　　1670　　　　　　　　　　1675 | | 5055 |
| aga gag acc ctg ctg acg ctg ctg gag gcc ttt gtg tac gac cct<br>Arg Glu Thr Leu Leu Thr Leu Leu Glu Ala Phe Val Tyr Asp Pro<br>　　　　　　　1680　　　　　　　　　　1685　　　　　　　　　　1690 | | 5100 |
| ctg gtg gac tgg aca gca gga ggc gag gct ggg ttt gct ggt gct<br>Leu Val Asp Trp Thr Ala Gly Gly Glu Ala Gly Phe Ala Gly Ala<br>　　　　　　　1695　　　　　　　　　　1700　　　　　　　　　　1705 | | 5145 |
| gtc tat ggt gga ggt ggc cag cag gcc gag agc aag cag agc aag<br>Val Tyr Gly Gly Gly Gly Gln Gln Ala Glu Ser Lys Gln Ser Lys<br>　　　　　　　1710　　　　　　　　　　1715　　　　　　　　　　1720 | | 5190 |
| aga gag atg gag cga gag atc acc cgc agc ctg ttt tct tct aga<br>Arg Glu Met Glu Arg Glu Ile Thr Arg Ser Leu Phe Ser Ser Arg<br>　　　　　　　1725　　　　　　　　　　1730　　　　　　　　　　1735 | | 5235 |
| gta gct gag att aag gtg aac tgg ttt aag aat aga gat gag atg<br>Val Ala Glu Ile Lys Val Asn Trp Phe Lys Asn Arg Asp Glu Met<br>　　　　　　　1740　　　　　　　　　　1745　　　　　　　　　　1750 | | 5280 |
| ctg gtt gtg ctt ccc aag ttg gac ggt agc tta gat gaa tac cta<br>Leu Val Val Leu Pro Lys Leu Asp Gly Ser Leu Asp Glu Tyr Leu<br>　　　　　　　1755　　　　　　　　　　1760　　　　　　　　　　1765 | | 5325 |
| agc ttg caa gag caa ctg aca gat gtg gaa aaa ctg cag ggc aaa<br>Ser Leu Gln Glu Gln Leu Thr Asp Val Glu Lys Leu Gln Gly Lys<br>　　　　　　　1770　　　　　　　　　　1775　　　　　　　　　　1780 | | 5370 |
| cta ctg gag gaa ata gag ttt cta gaa gga gct gaa ggg gtg gat<br>Leu Leu Glu Glu Ile Glu Phe Leu Glu Gly Ala Glu Gly Val Asp<br>　　　　　　　1785　　　　　　　　　　1790　　　　　　　　　　1795 | | 5415 |
| cat cct tct cat act ctg caa cac agg tat tct gag cac acc caa<br>His Pro Ser His Thr Leu Gln His Arg Tyr Ser Glu His Thr Gln<br>　　　　　　　1800　　　　　　　　　　1805　　　　　　　　　　1810 | | 5460 |
| cta cag act cag caa aga gct gtt cag gaa gca atc cag gtg aag<br>Leu Gln Thr Gln Gln Arg Ala Val Gln Glu Ala Ile Gln Val Lys<br>　　　　　　　1815　　　　　　　　　　1820　　　　　　　　　　1825 | | 5505 |
| ctg aat gaa ttt gaa caa tgg ata aca cat tat cag gct gca ttc<br>Leu Asn Glu Phe Glu Gln Trp Ile Thr His Tyr Gln Ala Ala Phe<br>　　　　　　　1830　　　　　　　　　　1835　　　　　　　　　　1840 | | 5550 |
| aat aat tta gaa gca aca cag ctt gca agc ttg ctt caa gag ata<br>Asn Asn Leu Glu Ala Thr Gln Leu Ala Ser Leu Leu Gln Glu Ile<br>　　　　　　　1845　　　　　　　　　　1850　　　　　　　　　　1855 | | 5595 |
| agc aca caa atg gac ctt ggt cct cca agt tac gtg cca gca aca<br>Ser Thr Gln Met Asp Leu Gly Pro Pro Ser Tyr Val Pro Ala Thr<br>　　　　　　　1860　　　　　　　　　　1865　　　　　　　　　　1870 | | 5640 |
| gcc ttt ctg cag aat gct ggt cag gcc cac ttg att agc cag tgc<br>Ala Phe Leu Gln Asn Ala Gly Gln Ala His Leu Ile Ser Gln Cys<br>　　　　　　　1875　　　　　　　　　　1880　　　　　　　　　　1885 | | 5685 |
| gag cag ctg gag ggg gag gtt ggt gct ctc ctg cag cag agg cgc<br>Glu Gln Leu Glu Gly Glu Val Gly Ala Leu Leu Gln Gln Arg Arg<br>　　　　　　　1890　　　　　　　　　　1895　　　　　　　　　　1900 | | 5730 |
| tcc gtg ctc cgt ggc tgt ctg gag caa ctg cat cac tat gca acc<br>Ser Val Leu Arg Gly Cys Leu Glu Gln Leu His His Tyr Ala Thr<br>　　　　　　　1905　　　　　　　　　　1910　　　　　　　　　　1915 | | 5775 |
| gtg gcc ctg cag tat ccg aag gcc ata ttt cag aaa cat cga att<br>Val Ala Leu Gln Tyr Pro Lys Ala Ile Phe Gln Lys His Arg Ile<br>　　　　　　　1920　　　　　　　　　　1925　　　　　　　　　　1930 | | 5820 |

-continued

```
gaa cag tgg aag acc tgg atg gaa gag ctc atc tgt aac acc aca    5865
Glu Gln Trp Lys Thr Trp Met Glu Glu Leu Ile Cys Asn Thr Thr
        1935                1940                1945 gta gag cgt tgt caa gag ctc tat agg aaa tat gaa atg caa tat    5910
Val Glu Arg Cys Gln Glu Leu Tyr Arg Lys Tyr Glu Met Gln Tyr
        1950                1955                1960 gct ccc cag cca ccc cca aca gtg tgt cag ttc atc act gcc act    5955
Ala Pro Gln Pro Pro Pro Thr Val Cys Gln Phe Ile Thr Ala Thr
        1965                1970                1975 gaa atg acc ctg cag cga tac gca gca gac atc aac agc aga ctt    6000
Glu Met Thr Leu Gln Arg Tyr Ala Ala Asp Ile Asn Ser Arg Leu
        1980                1985                1990 att aga caa gtg gaa cgc ttg aaa cag gaa gct gtc act gtg cca    6045
Ile Arg Gln Val Glu Arg Leu Lys Gln Glu Ala Val Thr Val Pro
        1995                2000                2005 gtt tgt gaa gat cag ttg aaa gaa att gaa cgt tgc att aaa gtt    6090
Val Cys Glu Asp Gln Leu Lys Glu Ile Glu Arg Cys Ile Lys Val
        2010                2015                2020 ttc ctt cat gag aat gga gaa gaa gga tct ttg agt cta gca agt    6135
Phe Leu His Glu Asn Gly Glu Glu Gly Ser Leu Ser Leu Ala Ser
        2025                2030                2035 gtt att att tct gcc ctt tgt acc ctt aca agg cgt aac ctg atg    6180
Val Ile Ile Ser Ala Leu Cys Thr Leu Thr Arg Arg Asn Leu Met
        2040                2045                2050 atg gaa ggt gca gcg tca agt gct gga gaa cag ctg gtt gat ctg    6225
Met Glu Gly Ala Ala Ser Ser Ala Gly Glu Gln Leu Val Asp Leu
        2055                2060                2065 act tct cgg gat gga gcc tgg ttc ttg gag gaa ctc tgc agt atg    6270
Thr Ser Arg Asp Gly Ala Trp Phe Leu Glu Glu Leu Cys Ser Met
        2070                2075                2080 agc gga aac gtc acc tgc ttg gtt cag tta ctg aag cag tgc cac    6315
Ser Gly Asn Val Thr Cys Leu Val Gln Leu Leu Lys Gln Cys His
        2085                2090                2095 ctg gtg cca cag gac tta gat atc ccg aac ccc atg gaa gcg tct    6360
Leu Val Pro Gln Asp Leu Asp Ile Pro Asn Pro Met Glu Ala Ser
        2100                2105                2110 gag aca gtt cac tta gcc aat gga gtg tat acc tca ctt cag gaa    6405
Glu Thr Val His Leu Ala Asn Gly Val Tyr Thr Ser Leu Gln Glu
        2115                2120                2125 ttg aat tcg aat ttc cgg caa atc ata ttt cca gaa gca ctt cga    6450
Leu Asn Ser Asn Phe Arg Gln Ile Ile Phe Pro Glu Ala Leu Arg
        2130                2135                2140 tgt tta atg aaa ggg gaa tac acg tta gaa agt atg ctg cat gaa    6495
Cys Leu Met Lys Gly Glu Tyr Thr Leu Glu Ser Met Leu His Glu
        2145                2150                2155 ctg gac ggt ctt att gag cag acc acc gat ggc gtt ccc ctg cag    6540
Leu Asp Gly Leu Ile Glu Gln Thr Thr Asp Gly Val Pro Leu Gln
        2160                2165                2170 act cta gtg gaa tct ctt cag gcc tac tta aga aac gca gct atg    6585
Thr Leu Val Glu Ser Leu Gln Ala Tyr Leu Arg Asn Ala Ala Met
        2175                2180                2185 gga ctg gaa gaa gaa aca cat gct cat tac atc gat gtt gcc aga    6630
Gly Leu Glu Glu Glu Thr His Ala His Tyr Ile Asp Val Ala Arg
        2190                2195                2200 cta cta cat gct cag tac ggt gaa tta atc caa ccg aga aat ggt    6675
Leu Leu His Ala Gln Tyr Gly Glu Leu Ile Gln Pro Arg Asn Gly
        2205                2210                2215 tca gtt gat gaa aca ccc aaa atg tca gct ggc cag atg ctt ttg    6720
Ser Val Asp Glu Thr Pro Lys Met Ser Ala Gly Gln Met Leu Leu
```

-continued

```
                   2220                 2225                 2230
gta gca ttc gat ggc atg ttt gct caa gtt gaa act gct ttc agc         6765
Val Ala Phe Asp Gly Met Phe Ala Gln Val Glu Thr Ala Phe Ser
                   2235                 2240                 2245 tta tta gtt gaa aag ttg aac aag atg gaa att ccc ata gct tgg         6810
Leu Leu Val Glu Lys Leu Asn Lys Met Glu Ile Pro Ile Ala Trp
                   2250                 2255                 2260 cga aag att gac atc ata agg gaa gcc agg agt act caa gtt aat         6855
Arg Lys Ile Asp Ile Ile Arg Glu Ala Arg Ser Thr Gln Val Asn
                   2265                 2270                 2275 ttt ttt gat gat gat aat cac cgg cag gtg cta gaa gag att ttc         6900
Phe Phe Asp Asp Asp Asn His Arg Gln Val Leu Glu Glu Ile Phe
                   2280                 2285                 2290 ttt cta aaa aga cta cag act att aag gag ttc ttc agg ctc tgt         6945
Phe Leu Lys Arg Leu Gln Thr Ile Lys Glu Phe Phe Arg Leu Cys
                   2295                 2300                 2305 ggt acc ttt tct aaa aca ttg tca gga tca agt tca ctt gaa gat         6990
Gly Thr Phe Ser Lys Thr Leu Ser Gly Ser Ser Ser Leu Glu Asp
                   2310                 2315                 2320 cag aat act gtg aat ggg cct gta cag att gtc aat gtg aaa acc         7035
Gln Asn Thr Val Asn Gly Pro Val Gln Ile Val Asn Val Lys Thr
                   2325                 2330                 2335 ctt ttt aga aac tct tgt ttc agt gaa gac caa atg gcc aaa cct         7080
Leu Phe Arg Asn Ser Cys Phe Ser Glu Asp Gln Met Ala Lys Pro
                   2340                 2345                 2350 atc aag gca ttc aca gct gac ttt gtg agg cag ctc ttg ata ggg         7125
Ile Lys Ala Phe Thr Ala Asp Phe Val Arg Gln Leu Leu Ile Gly
                   2355                 2360                 2365 cta ccc aac caa gcc ctc gga ctc aca ctg tgc agt ttt atc agt         7170
Leu Pro Asn Gln Ala Leu Gly Leu Thr Leu Cys Ser Phe Ile Ser
                   2370                 2375                 2380 gct ctg ggt gta gac atc att gct caa gta gag gca aag gac ttt         7215
Ala Leu Gly Val Asp Ile Ile Ala Gln Val Glu Ala Lys Asp Phe
                   2385                 2390                 2395 ggt gcc gaa agc aaa gtt tct gtt gat gat ctc tgt aag aaa gcg         7260
Gly Ala Glu Ser Lys Val Ser Val Asp Asp Leu Cys Lys Lys Ala
                   2400                 2405                 2410 gtg gaa cat aac atc cag ata ggg aag ttc tct cag ctg gtt atg         7305
Val Glu His Asn Ile Gln Ile Gly Lys Phe Ser Gln Leu Val Met
                   2415                 2420                 2425 aac agg gca act gtg tta gca agt tct tac gac act gcc tgg aag         7350
Asn Arg Ala Thr Val Leu Ala Ser Ser Tyr Asp Thr Ala Trp Lys
                   2430                 2435                 2440 aag cat gac ttg gtg cga agg cta gaa acc agt att tct tct tgt         7395
Lys His Asp Leu Val Arg Arg Leu Glu Thr Ser Ile Ser Ser Cys
                   2445                 2450                 2455 aag aca agc ctg cag cgg gtt cag ctg cat att gcc atg ttt cag         7440
Lys Thr Ser Leu Gln Arg Val Gln Leu His Ile Ala Met Phe Gln
                   2460                 2465                 2470 tgg caa cat gaa gat cta ctt atc aat aga cca caa gcc atg tca         7485
Trp Gln His Glu Asp Leu Leu Ile Asn Arg Pro Gln Ala Met Ser
                   2475                 2480                 2485 gtc aca cct ccc cca cgg tct gct atc cta acc agc atg aaa aag         7530
Val Thr Pro Pro Pro Arg Ser Ala Ile Leu Thr Ser Met Lys Lys
                   2490                 2495                 2500 aag ctg cat acc ctg agc cag att gaa act tct att gcg aca gtt         7575
Lys Leu His Thr Leu Ser Gln Ile Glu Thr Ser Ile Ala Thr Val
                   2505                 2510                 2515 cag gag aag cta gct gca ctt gaa tca agt att gaa cag cga ctc         7620
```

```
Gln Glu Lys Leu Ala   Ala Leu Glu Ser Ser   Ile Glu Gln Arg Leu
        2520                  2525                  2530 aag tgg gca ggt ggt   gcc aac cct gca ttg   gcc cct gta cta caa      7665
Lys Trp Ala Gly Gly   Ala Asn Pro Ala Leu   Ala Pro Val Leu Gln
        2535                  2540                  2545 gat ttt gaa gca acg   ata gct gaa aga aga   aat ctt gtc ctt aaa      7710
Asp Phe Glu Ala Thr   Ile Ala Glu Arg Arg   Asn Leu Val Leu Lys
        2550                  2555                  2560 gag agc caa aga gca   agt cag gtc aca ttt   ctc tgc agc aat atc      7755
Glu Ser Gln Arg Ala   Ser Gln Val Thr Phe   Leu Cys Ser Asn Ile
        2565                  2570                  2575 att cat ttt gaa agt   tta cga aca aga act   gca gaa gcc tta aac      7800
Ile His Phe Glu Ser   Leu Arg Thr Arg Thr   Ala Glu Ala Leu Asn
        2580                  2585                  2590 ctg gat gcg gcg tta   ttt gaa cta atc aag   cga tgt cag cag atg      7845
Leu Asp Ala Ala Leu   Phe Glu Leu Ile Lys   Arg Cys Gln Gln Met
        2595                  2600                  2605 tgt tcg ttt gca tca   cag ttt aac agt tca   gtg tct gag tta gag      7890
Cys Ser Phe Ala Ser   Gln Phe Asn Ser Ser   Val Ser Glu Leu Glu
        2610                  2615                  2620 ctt cgt tta tta cag   aga gtg gac act ggt   ctt gaa cat cct att      7935
Leu Arg Leu Leu Gln   Arg Val Asp Thr Gly   Leu Glu His Pro Ile
        2625                  2630                  2635 ggc agc tct gaa tgg   ctt ttg tca gca cac   aaa cag ttg acc cag      7980
Gly Ser Ser Glu Trp   Leu Leu Ser Ala His   Lys Gln Leu Thr Gln
        2640                  2645                  2650 gat atg tct act cag   agg gca att cag aca   gag aaa gag cag cag      8025
Asp Met Ser Thr Gln   Arg Ala Ile Gln Thr   Glu Lys Glu Gln Gln
        2655                  2660                  2665 ata gaa acg gtc tgt   gaa aca att cag aat   ctg gtt gat aat ata      8070
Ile Glu Thr Val Cys   Glu Thr Ile Gln Asn   Leu Val Asp Asn Ile
        2670                  2675                  2680 aag act gtg ctc act   ggt cat aac cga cag   ctt gga gat gtc aaa      8115
Lys Thr Val Leu Thr   Gly His Asn Arg Gln   Leu Gly Asp Val Lys
        2685                  2690                  2695 cat ctc ttg aaa gct   atg gct aag gat gaa   gaa gct gct ctg gca      8160
His Leu Leu Lys Ala   Met Ala Lys Asp Glu   Glu Ala Ala Leu Ala
        2700                  2705                  2710 gat ggt gaa gat gtt   ccc tat gag aac agt   gtt agg cag ttt ttg      8205
Asp Gly Glu Asp Val   Pro Tyr Glu Asn Ser   Val Arg Gln Phe Leu
        2715                  2720                  2725 ggt gaa tat aaa tca   tgg caa gac aac att   caa aca gtt cta ttt      8250
Gly Glu Tyr Lys Ser   Trp Gln Asp Asn Ile   Gln Thr Val Leu Phe
        2730                  2735                  2740 aca tta gtc cag gct   atg ggt cag gtt cga   agt caa gaa cac gtt      8295
Thr Leu Val Gln Ala   Met Gly Gln Val Arg   Ser Gln Glu His Val
        2745                  2750                  2755 gaa atg ctc cag gaa   atc act ccc acc ttg   aaa gaa ctg aaa aca      8340
Glu Met Leu Gln Glu   Ile Thr Pro Thr Leu   Lys Glu Leu Lys Thr
        2760                  2765                  2770 caa agt cag agt atc   tat aat aat tta gtg   agt ttt gca tca ccc      8385
Gln Ser Gln Ser Ile   Tyr Asn Asn Leu Val   Ser Phe Ala Ser Pro
        2775                  2780                  2785 tta gtc acc gat gca   aca aat gaa tgt tcg   agt cca acg tca tct      8430
Leu Val Thr Asp Ala   Thr Asn Glu Cys Ser   Ser Pro Thr Ser Ser
        2790                  2795                  2800 gct act tat cag cca   tcc ttc gct gca gca   gtc cgg agt aac act      8475
Ala Thr Tyr Gln Pro   Ser Phe Ala Ala Ala   Val Arg Ser Asn Thr
        2805                  2810                  2815
```

-continued

```
ggc cag aag act cag cct gat gtc atg tca cag aat gct aga aag    8520
Gly Gln Lys Thr Gln Pro Asp Val Met Ser Gln Asn Ala Arg Lys
            2820                2825                2830 ctg atc cag aaa aat ctt gct aca tca gct gat act cca cca agc    8565
Leu Ile Gln Lys Asn Leu Ala Thr Ser Ala Asp Thr Pro Pro Ser
            2835                2840                2845 acc gtt cca gga act ggc aag agt gtt gct tgt agt cct aaa aag    8610
Thr Val Pro Gly Thr Gly Lys Ser Val Ala Cys Ser Pro Lys Lys
            2850                2855                2860 gca gtc aga gac cct aaa act ggg aaa gcg gtg caa gag aga aac    8655
Ala Val Arg Asp Pro Lys Thr Gly Lys Ala Val Gln Glu Arg Asn
            2865                2870                2875 tcc tat gca gtg agt gtg tgg aag aga gtg aaa gcc aag tta gag    8700
Ser Tyr Ala Val Ser Val Trp Lys Arg Val Lys Ala Lys Leu Glu
            2880                2885                2890 ggc cga gat gtt gat ccg aat agg agg atg tca gtt gct gaa cag    8745
Gly Arg Asp Val Asp Pro Asn Arg Arg Met Ser Val Ala Glu Gln
            2895                2900                2905 gtt gac tat gtc att aag gaa gca act aat cta gat aac ttg gct    8790
Val Asp Tyr Val Ile Lys Glu Ala Thr Asn Leu Asp Asn Leu Ala
            2910                2915                2920 cag ctg tat gaa ggt tgg aca gcc tgg gtg tgaatggcaa gacagtag    8838
Gln Leu Tyr Glu Gly Trp Thr Ala Trp Val
            2925                2930
```

<210> SEQ ID NO 2
<211> LENGTH: 2930
<212> TYPE: PRT
<213> ORGANISM: Homo sapiens

<400> SEQUENCE: 2

```
Met Thr Trp Ala Leu Glu Ala Ala Val Leu Met Lys Lys Ser Glu Thr
1               5                   10                  15

Tyr Ala Pro Leu Phe Ser Leu Pro Ser Phe His Lys Phe Cys Lys Gly
                20                  25                  30

Leu Leu Ala Asn Thr Leu Val Glu Asp Val Asn Ile Cys Leu Gln Ala
            35                  40                  45

Cys Ser Ser Leu His Ala Leu Ser Ser Ser Leu Pro Asp Asp Leu Leu
        50                  55                  60

Gln Arg Cys Val Asp Val Cys Arg Val Gln Leu Val His Ser Gly Thr
65                  70                  75                  80

Arg Ile Arg Gln Ala Phe Gly Lys Leu Leu Lys Ser Ile Pro Leu Asp
                85                  90                  95

Val Val Leu Ser Asn Asn Asn His Thr Glu Ile Gln Glu Ile Ser Leu
            100                 105                 110

Ala Leu Arg Ser His Met Ser Lys Ala Pro Ser Asn Thr Phe His Pro
        115                 120                 125

Gln Asp Phe Ser Asp Val Ile Ser Phe Ile Leu Tyr Gly Asn Ser His
    130                 135                 140

Arg Thr Gly Lys Asp Asn Trp Leu Glu Arg Leu Phe Tyr Ser Cys Gln
145                 150                 155                 160

Arg Leu Asp Lys Arg Asp Gln Ser Thr Ile Pro Arg Asn Leu Leu Lys
                165                 170                 175

Thr Asp Ala Val Leu Trp Gln Trp Ala Ile Trp Glu Ala Ala Gln Phe
            180                 185                 190

Thr Val Leu Ser Lys Leu Arg Thr Pro Leu Gly Arg Ala Gln Asp Thr
        195                 200                 205
```

-continued

```
Phe Gln Thr Ile Glu Gly Ile Ile Arg Ser Leu Ala Ala His Thr Leu
    210                 215                 220
Asn Pro Asp Gln Asp Val Ser Gln Trp Thr Thr Ala Asp Asn Asp Glu
225                 230                 235                 240
Gly His Gly Asn Asn Gln Leu Arg Leu Val Leu Leu Leu Gln Tyr Leu
                245                 250                 255
Glu Asn Leu Glu Lys Leu Met Tyr Asn Ala Tyr Glu Gly Cys Ala Asn
            260                 265                 270
Ala Leu Thr Ser Pro Pro Lys Val Ile Arg Thr Phe Phe Tyr Thr Asn
        275                 280                 285
Arg Gln Thr Cys Gln Asp Trp Leu Thr Arg Ile Arg Leu Ser Ile Met
    290                 295                 300
Arg Val Gly Leu Leu Ala Gly Gln Pro Ala Val Thr Val Arg His Gly
305                 310                 315                 320
Phe Asp Leu Leu Thr Glu Met Lys Thr Thr Ser Leu Ser Gln Gly Asn
                325                 330                 335
Glu Leu Glu Val Thr Ile Met Met Val Val Glu Ala Leu Cys Glu Leu
            340                 345                 350
His Cys Pro Glu Ala Ile Gln Gly Ile Ala Val Trp Ser Ser Ser Ile
        355                 360                 365
Val Gly Lys Asn Leu Leu Trp Ile Asn Ser Val Ala Gln Gln Ala Glu
    370                 375                 380
Gly Arg Phe Glu Lys Ala Ser Val Glu Tyr Gln Glu His Leu Cys Ala
385                 390                 395                 400
Met Thr Gly Val Asp Cys Cys Ile Ser Ser Phe Asp Lys Ser Val Leu
                405                 410                 415
Thr Leu Ala Asn Ala Gly Arg Asn Ser Ala Ser Pro Lys His Ser Leu
            420                 425                 430
Asn Gly Glu Ser Arg Lys Thr Val Leu Ser Lys Pro Thr Asp Ser Ser
        435                 440                 445
Pro Glu Val Ile Asn Tyr Leu Gly Asn Lys Ala Cys Glu Cys Tyr Ile
    450                 455                 460
Ser Ile Ala Asp Trp Ala Ala Val Gln Glu Trp Gln Asn Ala Ile His
465                 470                 475                 480
Asp Leu Lys Lys Ser Thr Ser Thr Ser Leu Asn Leu Lys Ala Asp
                485                 490                 495
Phe Asn Tyr Ile Lys Ser Leu Ser Ser Phe Glu Ser Gly Lys Phe Val
            500                 505                 510
Glu Cys Thr Glu Gln Leu Glu Leu Leu Pro Gly Glu Asn Ile Asn Leu
        515                 520                 525
Leu Ala Gly Gly Ser Lys Glu Lys Ile Asp Met Lys Lys Leu Leu Pro
    530                 535                 540
Asn Met Leu Ser Pro Asp Pro Arg Glu Leu Gln Lys Ser Ile Glu Val
545                 550                 555                 560
Gln Leu Leu Arg Ser Ser Val Cys Leu Ala Thr Ala Leu Asn Pro Ile
                565                 570                 575
Glu Gln Asp Gln Lys Trp Gln Ser Ile Thr Glu Asn Val Val Lys Tyr
            580                 585                 590
Leu Lys Gln Thr Ser Arg Ile Ala Ile Gly Pro Leu Arg Leu Ser Thr
        595                 600                 605
Leu Thr Val Ser Gln Ser Leu Pro Val Leu Ser Thr Leu Gln Leu Tyr
    610                 615                 620
Cys Ser Ser Ala Leu Glu Asn Thr Val Ser Asn Arg Leu Ser Thr Glu
```

```
                    625              630              635              640
Asp Cys Leu Ile Pro Leu Phe Ser Glu Ala Leu Arg Ser Cys Lys Gln
                645              650              655
His Asp Val Arg Pro Trp Met Gln Ala Leu Arg Tyr Thr Met Tyr Gln
                660              665              670
Asn Gln Leu Leu Glu Lys Ile Lys Glu Gln Thr Val Pro Ile Arg Ser
                675              680              685
His Leu Met Glu Leu Gly Leu Thr Ala Ala Lys Phe Ala Arg Lys Arg
                690              695              700
Gly Asn Val Ser Leu Ala Thr Arg Leu Leu Ala Gln Cys Ser Glu Val
705              710              715              720
Gln Leu Gly Lys Thr Thr Ala Gln Asp Leu Val Gln His Phe Lys
                    725              730              735
Lys Leu Ser Thr Gln Gly Gln Val Asp Glu Lys Trp Gly Pro Glu Leu
                740              745              750
Asp Ile Glu Lys Thr Lys Leu Leu Tyr Thr Ala Gly Gln Ser Thr His
                755              760              765
Ala Met Glu Met Leu Ser Ser Cys Ala Ile Ser Phe Cys Lys Ser Val
770              775              780
Lys Ala Glu Tyr Ala Val Ala Lys Ser Ile Leu Thr Leu Ala Lys Trp
785              790              795              800
Ile Gln Ala Glu Trp Lys Glu Ile Ser Gly Gln Leu Lys Gln Val Tyr
                805              810              815
Arg Ala Gln His Gln Asn Phe Thr Gly Leu Ser Thr Leu Ser Lys
                820              825              830
Asn Ile Leu Thr Leu Ile Glu Leu Pro Ser Val Asn Thr Met Glu Glu
                835              840              845
Glu Tyr Pro Arg Ile Glu Ser Glu Ser Thr Val His Ile Gly Val Gly
                850              855              860
Glu Pro Asp Phe Ile Leu Gly Gln Leu Tyr His Leu Ser Ser Val Gln
865              870              875              880
Ala Pro Glu Val Ala Lys Ser Trp Ala Ala Leu Ala Ser Trp Ala Tyr
                885              890              895
Arg Trp Gly Arg Lys Val Val Asp Asn Ala Ser Gln Gly Glu Gly Val
                900              905              910
Arg Leu Leu Pro Arg Glu Lys Ser Glu Val Gln Asn Leu Leu Pro Asp
                915              920              925
Thr Ile Thr Glu Glu Lys Glu Arg Ile Tyr Gly Ile Leu Gly Gln
                930              935              940
Ala Val Cys Arg Pro Ala Gly Ile Gln Asp Glu Asp Ile Thr Leu Gln
945              950              955              960
Ile Thr Glu Ser Glu Asp Asn Glu Glu Asp Met Val Asp Val Ile
                965              970              975
Trp Arg Gln Leu Ile Ser Ser Cys Pro Trp Leu Ser Glu Leu Asp Glu
                980              985              990
Ser Ala Thr Glu Gly Val Ile Lys Val Trp Arg Lys Val Val Asp Arg
                995              1000             1005
Ile Phe Ser Leu Tyr Lys Leu Ser Cys Ser Ala Tyr Phe Thr Phe
                1010             1015             1020
Leu Lys Leu Asn Ala Gly Gln Ile Pro Leu Asp Glu Asp Asp Pro
                1025             1030             1035
Arg Leu His Leu Ser His Arg Val Glu Gln Ser Thr Asp Asp Met
                1040             1045             1050
```

-continued

```
Ile Val Met Ala Thr Leu Arg Leu Leu Arg Leu Leu Val Lys His
1055                1060               1065

Ala Gly Glu Leu Arg Gln Tyr Leu Glu His Gly Leu Glu Thr Thr
1070                1075               1080

Pro Thr Ala Pro Trp Arg Gly Ile Ile Pro Gln Leu Phe Ser Arg
1085                1090               1095

Leu Asn His Pro Glu Val Tyr Val Arg Gln Ser Ile Cys Asn Leu
1100                1105               1110

Leu Cys Arg Val Ala Gln Asp Ser Pro His Leu Ile Leu Tyr Pro
1115                1120               1125

Ala Ile Val Gly Thr Ile Ser Leu Ser Ser Glu Ser Gln Ala Ser
1130                1135               1140

Gly Asn Lys Phe Ser Thr Ala Ile Pro Thr Leu Leu Gly Asn Ile
1145                1150               1155

Gln Gly Glu Glu Leu Leu Val Ser Glu Cys Glu Gly Gly Ser Pro
1160                1165               1170

Pro Ala Ser Gln Asp Ser Asn Lys Asp Glu Pro Lys Ser Gly Leu
1175                1180               1185

Asn Glu Asp Gln Ala Met Met Gln Asp Cys Tyr Ser Lys Ile Val
1190                1195               1200

Asp Lys Leu Ser Ser Ala Asn Pro Thr Met Val Leu Gln Val Gln
1205                1210               1215

Met Leu Val Ala Glu Leu Arg Arg Val Thr Val Leu Trp Asp Glu
1220                1225               1230

Leu Trp Leu Gly Val Leu Leu Gln Gln His Met Tyr Val Leu Arg
1235                1240               1245

Arg Ile Gln Gln Leu Glu Asp Glu Val Lys Arg Val Gln Asn Asn
1250                1255               1260

Asn Thr Leu Arg Lys Glu Glu Lys Ile Ala Ile Met Arg Glu Lys
1265                1270               1275

His Thr Ala Leu Met Lys Pro Ile Val Phe Ala Leu Glu His Val
1280                1285               1290

Arg Ser Ile Thr Ala Ala Pro Ala Glu Thr Pro His Glu Lys Trp
1295                1300               1305

Phe Gln Asp Asn Tyr Gly Asp Ala Ile Glu Asn Ala Leu Glu Lys
1310                1315               1320

Leu Lys Thr Pro Leu Asn Pro Ala Lys Pro Gly Ser Ser Trp Ile
1325                1330               1335

Pro Phe Lys Glu Ile Met Leu Ser Leu Gln Gln Arg Ala Gln Lys
1340                1345               1350

Arg Ala Ser Tyr Ile Leu Arg Leu Glu Glu Ile Ser Pro Trp Leu
1355                1360               1365

Ala Ala Met Thr Asn Thr Glu Ile Ala Leu Pro Gly Glu Val Ser
1370                1375               1380

Ala Arg Asp Thr Val Thr Ile His Ser Val Gly Gly Thr Ile Thr
1385                1390               1395

Ile Leu Pro Thr Lys Thr Lys Pro Lys Lys Leu Leu Phe Leu Gly
1400                1405               1410

Ser Asp Gly Lys Ser Tyr Pro Tyr Leu Phe Lys Gly Leu Glu Asp
1415                1420               1425

Leu His Leu Asp Glu Arg Ile Met Gln Phe Leu Ser Ile Val Asn
1430                1435               1440
```

-continued

```
Thr Met Phe Ala Thr Ile Asn Arg Gln Glu Thr Pro Arg Phe His
1445                1450                1455

Ala Arg His Tyr Ser Val Thr Pro Leu Gly Thr Arg Ser Gly Leu
    1460                1465                1470

Ile Gln Trp Val Asp Gly Ala Thr Pro Leu Phe Gly Leu Tyr Lys
    1475                1480                1485

Arg Trp Gln Gln Arg Glu Ala Ala Leu Gln Ala Gln Lys Ala Gln
1490                1495                1500

Asp Ser Tyr Gln Thr Pro Gln Asn Pro Gly Ile Val Pro Arg Pro
    1505                1510                1515

Ser Glu Leu Tyr Tyr Ser Lys Ile Gly Pro Ala Leu Lys Thr Val
    1520                1525                1530

Gly Leu Ser Leu Asp Val Ser Arg Arg Asp Trp Pro Leu His Val
1535                1540                1545

Met Lys Ala Val Leu Glu Glu Leu Met Glu Ala Thr Pro Pro Asn
    1550                1555                1560

Leu Leu Ala Lys Glu Leu Trp Ser Ser Cys Thr Thr Pro Asp Glu
    1565                1570                1575

Trp Trp Arg Val Thr Gln Ser Tyr Ala Arg Ser Thr Ala Val Met
1580                1585                1590

Ser Met Val Gly Tyr Ile Ile Gly Leu Gly Asp Arg His Leu Asp
    1595                1600                1605

Asn Val Leu Ile Asp Met Thr Thr Gly Glu Val Val His Ile Asp
    1610                1615                1620

Tyr Asn Val Cys Phe Glu Lys Gly Lys Ser Leu Arg Val Pro Glu
1625                1630                1635

Lys Val Pro Phe Arg Met Thr Gln Asn Ile Glu Thr Ala Leu Gly
    1640                1645                1650

Val Thr Gly Val Glu Gly Val Phe Arg Leu Ser Cys Glu Gln Val
    1655                1660                1665

Leu His Ile Met Arg Arg Gly Arg Glu Thr Leu Leu Thr Leu Leu
    1670                1675                1680

Glu Ala Phe Val Tyr Asp Pro Leu Val Asp Trp Thr Ala Gly Gly
1685                1690                1695

Glu Ala Gly Phe Ala Gly Ala Val Tyr Gly Gly Gly Gly Gln Gln
    1700                1705                1710

Ala Glu Ser Lys Gln Ser Lys Arg Glu Met Glu Arg Glu Ile Thr
1715                1720                1725

Arg Ser Leu Phe Ser Ser Arg Val Ala Glu Ile Lys Val Asn Trp
    1730                1735                1740

Phe Lys Asn Arg Asp Glu Met Leu Val Val Leu Pro Lys Leu Asp
    1745                1750                1755

Gly Ser Leu Asp Glu Tyr Leu Ser Leu Gln Glu Gln Leu Thr Asp
    1760                1765                1770

Val Glu Lys Leu Gln Gly Lys Leu Leu Glu Glu Ile Glu Phe Leu
    1775                1780                1785

Glu Gly Ala Glu Gly Val Asp His Pro Ser His Thr Leu Gln His
1790                1795                1800

Arg Tyr Ser Glu His Thr Gln Leu Gln Thr Gln Gln Arg Ala Val
    1805                1810                1815

Gln Glu Ala Ile Gln Val Lys Leu Asn Glu Phe Glu Gln Trp Ile
    1820                1825                1830

Thr His Tyr Gln Ala Ala Phe Asn Asn Leu Glu Ala Thr Gln Leu
```

-continued

```
            1835                1840                1845

Ala Ser Leu Leu Gln Glu Ile Ser Thr Gln Met Asp Leu Gly Pro
        1850                1855                1860

Pro Ser Tyr Val Pro Ala Thr Ala Phe Leu Gln Asn Ala Gly Gln
        1865                1870                1875

Ala His Leu Ile Ser Gln Cys Glu Gln Leu Glu Gly Glu Val Gly
        1880                1885                1890

Ala Leu Leu Gln Gln Arg Arg Ser Val Leu Arg Gly Cys Leu Glu
        1895                1900                1905

Gln Leu His His Tyr Ala Thr Val Ala Leu Gln Tyr Pro Lys Ala
        1910                1915                1920

Ile Phe Gln Lys His Arg Ile Glu Gln Trp Lys Thr Trp Met Glu
        1925                1930                1935

Glu Leu Ile Cys Asn Thr Thr Val Glu Arg Cys Gln Glu Leu Tyr
        1940                1945                1950

Arg Lys Tyr Glu Met Gln Tyr Ala Pro Gln Pro Pro Thr Val
        1955                1960                1965

Cys Gln Phe Ile Thr Ala Thr Glu Met Thr Leu Gln Arg Tyr Ala
        1970                1975                1980

Ala Asp Ile Asn Ser Arg Leu Ile Arg Gln Val Glu Arg Leu Lys
        1985                1990                1995

Gln Glu Ala Val Thr Val Pro Val Cys Glu Asp Gln Leu Lys Glu
        2000                2005                2010

Ile Glu Arg Cys Ile Lys Val Phe Leu His Glu Asn Gly Glu Glu
        2015                2020                2025

Gly Ser Leu Ser Leu Ala Ser Val Ile Ile Ser Ala Leu Cys Thr
        2030                2035                2040

Leu Thr Arg Arg Asn Leu Met Met Glu Gly Ala Ala Ser Ser Ala
        2045                2050                2055

Gly Glu Gln Leu Val Asp Leu Thr Ser Arg Asp Gly Ala Trp Phe
        2060                2065                2070

Leu Glu Glu Leu Cys Ser Met Ser Gly Asn Val Thr Cys Leu Val
        2075                2080                2085

Gln Leu Leu Lys Gln Cys His Leu Val Pro Gln Asp Leu Asp Ile
        2090                2095                2100

Pro Asn Pro Met Glu Ala Ser Glu Thr Val His Leu Ala Asn Gly
        2105                2110                2115

Val Tyr Thr Ser Leu Gln Glu Leu Asn Ser Asn Phe Arg Gln Ile
        2120                2125                2130

Ile Phe Pro Glu Ala Leu Arg Cys Leu Met Lys Gly Glu Tyr Thr
        2135                2140                2145

Leu Glu Ser Met Leu His Glu Leu Asp Gly Leu Ile Glu Gln Thr
        2150                2155                2160

Thr Asp Gly Val Pro Leu Gln Thr Leu Val Glu Ser Leu Gln Ala
        2165                2170                2175

Tyr Leu Arg Asn Ala Ala Met Gly Leu Glu Glu Thr His Ala
        2180                2185                2190

His Tyr Ile Asp Val Ala Arg Leu Leu His Ala Gln Tyr Gly Glu
        2195                2200                2205

Leu Ile Gln Pro Arg Asn Gly Ser Val Asp Glu Thr Pro Lys Met
        2210                2215                2220

Ser Ala Gly Gln Met Leu Leu Val Ala Phe Asp Gly Met Phe Ala
        2225                2230                2235
```

-continued

```
Gln Val Glu Thr Ala Phe Ser Leu Leu Val Glu Lys Leu Asn Lys
    2240            2245                2250

Met Glu Ile Pro Ile Ala Trp Arg Lys Ile Asp Ile Ile Arg Glu
    2255            2260                2265

Ala Arg Ser Thr Gln Val Asn Phe Phe Asp Asp Asn His Arg
    2270            2275                2280

Gln Val Leu Glu Glu Ile Phe Phe Leu Lys Arg Leu Gln Thr Ile
    2285            2290                2295

Lys Glu Phe Phe Arg Leu Cys Gly Thr Phe Ser Lys Thr Leu Ser
    2300            2305                2310

Gly Ser Ser Ser Leu Glu Asp Gln Asn Thr Val Asn Gly Pro Val
    2315            2320                2325

Gln Ile Val Asn Val Lys Thr Leu Phe Arg Asn Ser Cys Phe Ser
    2330            2335                2340

Glu Asp Gln Met Ala Lys Pro Ile Lys Ala Phe Thr Ala Asp Phe
    2345            2350                2355

Val Arg Gln Leu Leu Ile Gly Leu Pro Asn Gln Ala Leu Gly Leu
    2360            2365                2370

Thr Leu Cys Ser Phe Ile Ser Ala Leu Gly Val Asp Ile Ile Ala
    2375            2380                2385

Gln Val Glu Ala Lys Asp Phe Gly Ala Glu Ser Lys Val Ser Val
    2390            2395                2400

Asp Asp Leu Cys Lys Lys Ala Val Glu His Asn Ile Gln Ile Gly
    2405            2410                2415

Lys Phe Ser Gln Leu Val Met Asn Arg Ala Thr Val Leu Ala Ser
    2420            2425                2430

Ser Tyr Asp Thr Ala Trp Lys Lys His Asp Leu Val Arg Arg Leu
    2435            2440                2445

Glu Thr Ser Ile Ser Ser Cys Lys Thr Ser Leu Gln Arg Val Gln
    2450            2455                2460

Leu His Ile Ala Met Phe Gln Trp Gln His Glu Asp Leu Leu Ile
    2465            2470                2475

Asn Arg Pro Gln Ala Met Ser Val Thr Pro Pro Arg Ser Ala
    2480            2485                2490

Ile Leu Thr Ser Met Lys Lys Lys Leu His Thr Leu Ser Gln Ile
    2495            2500                2505

Glu Thr Ser Ile Ala Thr Val Gln Glu Lys Leu Ala Ala Leu Glu
    2510            2515                2520

Ser Ser Ile Glu Gln Arg Leu Lys Trp Ala Gly Gly Ala Asn Pro
    2525            2530                2535

Ala Leu Ala Pro Val Leu Gln Asp Phe Glu Ala Thr Ile Ala Glu
    2540            2545                2550

Arg Arg Asn Leu Val Leu Lys Glu Ser Gln Arg Ala Ser Gln Val
    2555            2560                2565

Thr Phe Leu Cys Ser Asn Ile Ile His Phe Glu Ser Leu Arg Thr
    2570            2575                2580

Arg Thr Ala Glu Ala Leu Asn Leu Asp Ala Ala Leu Phe Glu Leu
    2585            2590                2595

Ile Lys Arg Cys Gln Gln Met Cys Ser Phe Ala Ser Gln Phe Asn
    2600            2605                2610

Ser Ser Val Ser Glu Leu Glu Leu Arg Leu Leu Gln Arg Val Asp
    2615            2620                2625
```

-continued

```
Thr Gly Leu Glu His Pro Ile Gly Ser Ser Glu Trp Leu Leu Ser
    2630            2635            2640

Ala His Lys Gln Leu Thr Gln Asp Met Ser Thr Gln Arg Ala Ile
    2645            2650            2655

Gln Thr Glu Lys Glu Gln Gln Ile Glu Thr Val Cys Glu Thr Ile
    2660            2665            2670

Gln Asn Leu Val Asp Asn Ile Lys Thr Val Leu Thr Gly His Asn
    2675            2680            2685

Arg Gln Leu Gly Asp Val Lys His Leu Leu Lys Ala Met Ala Lys
    2690            2695            2700

Asp Glu Glu Ala Ala Leu Ala Asp Gly Glu Asp Val Pro Tyr Glu
    2705            2710            2715

Asn Ser Val Arg Gln Phe Leu Gly Glu Tyr Lys Ser Trp Gln Asp
    2720            2725            2730

Asn Ile Gln Thr Val Leu Phe Thr Leu Val Gln Ala Met Gly Gln
    2735            2740            2745

Val Arg Ser Gln Glu His Val Glu Met Leu Gln Glu Ile Thr Pro
    2750            2755            2760

Thr Leu Lys Glu Leu Lys Thr Gln Ser Gln Ser Ile Tyr Asn Asn
    2765            2770            2775

Leu Val Ser Phe Ala Ser Pro Leu Val Thr Asp Ala Thr Asn Glu
    2780            2785            2790

Cys Ser Ser Pro Thr Ser Ser Ala Thr Tyr Gln Pro Ser Phe Ala
    2795            2800            2805

Ala Ala Val Arg Ser Asn Thr Gly Gln Lys Thr Gln Pro Asp Val
    2810            2815            2820

Met Ser Gln Asn Ala Arg Lys Leu Ile Gln Lys Asn Leu Ala Thr
    2825            2830            2835

Ser Ala Asp Thr Pro Pro Ser Thr Val Pro Gly Thr Gly Lys Ser
    2840            2845            2850

Val Ala Cys Ser Pro Lys Lys Ala Val Arg Asp Pro Lys Thr Gly
    2855            2860            2865

Lys Ala Val Gln Glu Arg Asn Ser Tyr Ala Val Ser Val Trp Lys
    2870            2875            2880

Arg Val Lys Ala Lys Leu Glu Gly Arg Asp Val Asp Pro Asn Arg
    2885            2890            2895

Arg Met Ser Val Ala Glu Gln Val Asp Tyr Val Ile Lys Glu Ala
    2900            2905            2910

Thr Asn Leu Asp Asn Leu Ala Gln Leu Tyr Glu Gly Trp Thr Ala
    2915            2920            2925

Trp Val
    2930

<210> SEQ ID NO 3
<211> LENGTH: 4651
<212> TYPE: DNA
<213> ORGANISM: Homo sapiens

<400> SEQUENCE: 3
gaattcgccc ttcggaacca tcacaatctt accgactaaa accaagccaa agaaacttct    60
ctttcttgga tcagatggga agagctatcc ttatcttttc aaaggactgg aggatttaca   120
tctggatgag agaataatgc agttcctatc tattgtgaat accatgtttg ctacaattaa   180
tcgccaagaa acaccccggt tccatgctcg acactattct gtaacaccac taggaacaag   240
```

-continued

```
atcaggacta atccagtggg tagatggagc cacacccTTa tttggtctTT acaaacgatg      300
gcaacaacgg gaagctgcct tacaagcaca aaaggcccaa gattcctacc aaactcctca      360
gaatcctgga attgtacccc gtcctagtga actttattac agtaaaattg gccctgcTTT      420
gaaaacagtt gggcttagcc tggatgtgtc ccgtcgggat tggcctcttc atgtaatgaa      480
ggcagtattg gaaagagttaa tggaggccac accccgaat ctccttgcca aagagctctg      540
gtcatcttgc acaacacctg atgaatggtg gagagttacg cagtcttatg caagatctac      600
tgcagtcatg tctatggttg gatacataat tggccttgga gacagacatc tggataatgt      660
tcttatagat atgacgactg gagaagttgt tcacatagat tacaatgttt gctttgaaaa      720
aggtaaaagc cttagagttc ctgagaaagt acctTTtcga atgacacaaa acattgaaac      780
agcactgggt gtaactggag tagaaggtgt atTTaggctt tcatgtgagc aggTTTTaca      840
cattatgcgg cgtggcagag agaccctgct gacgctgctg gaggccTTTg tgtacgaccc      900
tctggtggac tggacagcag gaggcgaggc tgggTTTgct ggtgctgtct atggtggagg      960
tggccagcag gccgagagca agcagagcaa gagagagatg gagcgagaga tcacccgcag     1020
cctgTTTTct tctagagtag ctgagaTTaa ggtgaactgg TTTaagaata gagatgagat     1080
gctggttgtg cTTcccaagt tggacggtag cTTagatgaa tacctaagct tgcaagagca     1140
actgacagat gtggaaaaac tgcagggcaa actactggag gaaatagagt TTctagaagg     1200
agctgaaggg gtggatcatc cTTctcatac tctgcaacac aggtattctg agcacaccca     1260
actacagact cagcaaagag ctgTTcagga agcaatccag gtgaagctga atgaaTTTga     1320
acaatggata acacattatc aggctgcatt caataaTTTa gaagcaacac agcttgcaag     1380
cttgcTTcaa gagataagca cacaaatgga ccTTggtcct ccaagTTacg tgccagcaac     1440
agccTTTctg cagaatgctg gtcaggccca cTTgaTTagc cagtgcgagc agctggaggg     1500
ggaggTTggt gctctcctgc agcagaggcg ctccgtgctc cgtggctgtc tggagcaact     1560
gcatcactat gcgaccgtgg ccctgcagta tccgaaggcc ataTTTcaga acatcgaat     1620
tgaacagtgg aagacctgga tggaagagct catctgtaac accacagtag agcgTTgtca     1680
agagctctat aggaaatatg aaatgcaata tgctccccag ccacccccaa cagtgtgtca     1740
gTTcatcact gccactgaaa tgaccctgca gcgatacgca gcagacatca acagcagact     1800
taTTagacaa gtggaacgct tgaaacagga agctgtcact gtgccagttt gtgaagatca     1860
gTTgaaagaa aTTgaacgTT gcaTTaaagt TTTccTTcat gagaatggag aagaaggatc     1920
tTTgagtcta gcaagtgTTa tTTaTTTctgc ccTTTgtacc cTTacaaggc gtaacctgat     1980
gatgaaggt gcagcgtcaa gtgctggaga acagctggTT gatctgacTT ctcgggatgg     2040
agcctggTTc TTggaggaac tctgcagtat gagcggaaac gtcacctgct ggTTcagTT     2100
actgaagcag tgccacctgg tgccacagga cTTagatatc ccgaacccca tggaagcgtc     2160
tgagacagTT cacTTagcca atggagtgta tacctcactt caggaaTTga aTTcgaaTTT     2220
ccggcaaatc ataTTTccag aagcacTTcg atgTTTaatg aaagggaat acacgTTaga     2280
aagtatgctg catgaactgg acggtcTTat tgagcagacc accgatggcg TTccccTGCa     2340
gactctagtg gaatctcTTc aggcctactt aagaaacgca gctatgggac tggaagaaga     2400
aacacatgct caTTacatcg atgTTgccag actactacat gctcagtacg gtgaaTTaat     2460
ccaaccgaga atggTTcag TTgatgaaac acccaaaatg tcagctggcc agatgcTTTT     2520
ggtagcattc gatggcatgt TTgctcaagt tgaaactgct TTcagcttat tagTTgaaaa     2580
gTTgaacaag atggaaaTTc ccatagcTTg gcgaaagaTT gacatcataa gggaagccag     2640
```

-continued

```
gagtactcaa gttaattttt ttgatgatga taatcaccgg caggtgctag aagagatttt    2700
ctttctaaaa agactacaga ctattaagga gttcttcagg ctctgtggta cctttttctaa   2760
aacattgtca ggatcaagtt cacttgaaga tcagaatact gtgaatgggc ctgtacagat    2820
tgtcaatgtg aaaaccettt ttagaaactc ttgtttcagt gaagaccaaa tggccaaacc    2880
tatcaaggca ttcacagctg actttgtgag gcagctcttg ataggggctac ccaaccaagc   2940
cctcggactc acactgtgca gttttatcag tgctctgggt gtagacatca ttgctcaagt    3000
agaggcaaag gactttggtg ccgaaagcaa agtttctgtt gatgatctct gtaagaaagc    3060
ggtggaacat aacatccaga tagggaagtt ctctcagctg gttatgaaca gggcaactgt    3120
gttagcaagt tcttacgaca ctgcctggaa gaagcatgac ttggtgcgaa ggctagaaac    3180
cagtatttct tcttgtaaga caagcctgca gcgggttcag ctgcatattg ccatgtttca    3240
gtggcaacat gaagatctac ttatcaatag accacaagcc atgtcagcca cactcccccc    3300
acggtctgct atcctaacca gcatgaaaaa gaagctgcat accctgagcc agattgaaac    3360
ttctattgcg acagttcagg agaagctagc tgcacttgaa tcaagtattg aacagcgact    3420
caagtgggca ggtggtgcca accctgcatt ggcccctgta ctacaagatt ttgaagcaac    3480
gatagctgaa agaagaaatc ttgtccttaa agagagccaa agagcaagtc aggtcacatt    3540
tctctgcagc aatatcattc attttgaaag tttacgaaca agaactgcag aagccttaaa    3600
cctggatgcg gcgttatttg aactaatcaa gcgatgtcag cagatgtgtt cgtttgcatc    3660
acagtttaac agttcagtgt ctgagttaga gcttcgttta ttacagagag tggacactgg    3720
tcttgaacat cctattggca gctctgaatg gcttttgtca gcacacaaac agttgaccca    3780
ggatatgtct actcagaggg caattcagac agagaaagag cagcagatag aaacggtctg    3840
tgaaacaatt cagaatctgg ttgataatat aaagactgtg ctcactggtc ataaccgaca    3900
gcttggagat gtcaaacatc tcttgaaagc tatggctaag gatgaagaag ctgctctggc    3960
agatggtgaa gatgttccct atgagaacag tgttaggcag ttttttgggtg aatataaatc    4020
atggcaagac aacattcaaa cagttctatt tacattagtc caggctatgg gtcaggttcg    4080
aagtcaagaa cacgttgaaa tgctccagga atcactccc accttgaaag aactgaaaac    4140
acaaagtcag agtatctata ataatttagt gagtttttgca tcacccttag tcaccgatgc    4200
aacaaatgaa tgttcgagtc caacgtcatc tgctacttat cagccatcct tcgctgcagc    4260
agtccggagt aacactggcc agaagactca gcctgatgtc atgtcacaga atgctagaaa    4320
gctgatccag aaaaatcttg ctacatcagc tgatactcca ccaagcaccg ttccaggaac    4380
tggcaagagt gttgcttgta gtcctaaaaa ggcagtcaga gaccctaaaa ctgggaaagc    4440
ggtgcaagag agaaactcct atgcagtgag tgtgtggaag agagtgaaag ccaagttaga    4500
gggccgagat gttgatccga ataggaggat gtcagttgct gaacaggttg actatgtcat    4560
taaggaagca actaatctag ataacttggc tcagctgtat gaaggttgga cagcctgggt    4620
gtgaatggca agacagtaga agggcgaatt c                                   4651
```

<210> SEQ ID NO 4
<211> LENGTH: 4610
<212> TYPE: DNA
<213> ORGANISM: Homo sapiens

<400> SEQUENCE: 4

```
gaattcgccc ttcggaacca tcacaatctt accgactaaa accaagccaa agaaacttct     60
```

-continued

```
ctttcttgga tcagatggga agagctatcc ttatcttttc aaaggactgg aggatttaca    120
tctggatgag agaataatgc agttcctatc tattgtgaat accatgtttg ctacaattaa    180
tcgccaagaa acaccccggt tccatgctcg acactattct gtaacaccac taggaacaag    240
atcaggacta atccagtggg tagatggagc cacacccta tttggtcttt acaaacgatg     300
gcaacaacgg gaagctgcct acaagcaca aaaggcccaa gattcctacc aaactcctca     360
gaatcctgga attgtacccc gtcctagtga actttattac agtaaaattg gccctgcttt    420
gaaaacagtt gggcttagcc tggatgtgtc ccgtcgggat tggcctcttc atgtaatgaa    480
ggcagtattg gaagagttaa tggaggccac accccgaat ctccttgcca aagagctctg     540
gtcatcttgc acaacacctg atgaatggtg gagagttacg cagtcttatg caagatctac    600
tgcagtcatg tctatggttg gatacataat tggccttgga gacagacatc tggataatgt    660
tcttatagat atgacgactg agaagttgt tcacatagat acaatgtttt gctttgaaaa     720
aggtaaaagc cttagagttc ctgagaaagt acctttttcga atgacacaaa acattgaaac   780
agcactgggt gtaactggag tagaaggtgt atttaggctt tcatgtgagc aggttttaca    840
cattatgcgg cgtggcagag agaccctgct gacgctgctg gaggcctttg tgtacgaccc    900
tctggtggac tggacagcag gaggcgaggc tgggtttgct ggtgctgtct atggtggagg    960
tggccagcag gccgagagca agcagagcaa gagagagatg gagcgagaga tcacccgcag    1020
cctgttttct tctagagtag ctgagattaa ggtgaactgg tttaagaata gagatgagat    1080
gctggttgtg cttcccaagt tggacggtag cttagatgaa tacctaagct tgcaagagca    1140
actgacagat gtggaaaaac tgcagggcaa actactggag gaaatagagt ttctagaagg    1200
agctgaaggg gtggatcatc cttctcatac tctgcaacac aggtattctg agcacaccca    1260
actacagact cagcaaagag ttgttcagga agcaatccag gtgaagctga atgaatttga    1320
acaatggata acacattatc aggctgcatt caataattta gaagcaacac agcttgcaag    1380
cttgcttcaa gagataagca cacaaatgga ccttggtcct ccaagttacg tgccagcaac    1440
agcctttctg cagaatgctg gtcaggccca cttgattagc cagtgcgagc agctggaggg    1500
ggaggttggt gctctcctgc agcagaggcg ctccgtgctc cgtggctgtc tggagcaact    1560
gcatacactat gcaaccgtgg ccctgcagta tccgaaggcc atatttcaga acatcgaat    1620
tgaacagtgg aagacctgga tggaagagct catctgtaac accacagtag agcgttgtca    1680
agagctctat aggaaatatg aaatgcaata tgctccccag ccaccccaa cagtgtgtca    1740
gttcatcact gccactgaaa tgaccctgca gcgatacgca gcagacatca acagcagact    1800
tattagacaa gtggaacgct tgaaacagga agctgtcact gtgccagttt gtgaagatca    1860
gttgaaagaa attgaacgtt gcattaaagt tttccttcat gagaatggag aagaaggatc    1920
tttgagtcta gcaagtgtta ttatttctgc cctttgtacc cttacaaggc gtaacctgat    1980
gatgaaggt gcagcgtcaa gtgctggaga acagctggtt gatctgactt ctcgggatgg    2040
agcctggttc ttggaggaac tctgcagtat gagcggaaac gtcacctgct tggttcagtt    2100
actgaagcag tgccacctgg tgccacagga cttagatatc ccgaaccca tggaagcgtc    2160
tgagacagtt cacttagcca atggagtgta tacctcactt caggaattga attcgaattt    2220
ccggcaaatc atatttccag aagcacttcg atgtttaatg aaagggaat acacgttaga    2280
aagtatgctg catgaactgg acggtcttat tgagcagacc accgatggcg ttcccctgca    2340
gactctagtg gaatctcttc aggcctactt aagaaacgca gctatgggac tggaagaaga    2400
aacacatgct cattacatcg atgttgccag actactacac gctcagtacg gtgaattaat    2460
```

-continued

```
ccaaccgaga aatggttcag ttgatgaaac acccaaaatg tcagctggcc agatgctttt      2520
ggtagcattc gatggcatgt tgctcaagt tgaaactgct ttcagcttat tagttgaaaa       2580
gttgaacaag atggaaattc ccatagcttg gcgaaagatt gacatcataa gggaagccag      2640
gagtactcaa gttaattttt tgatgatga taatcaccgg caggtgctag aagagatttt      2700
cttcctaaaa agactacaga ctattaagga gttcttcagg ctctgtggta ccttttctaa     2760
aacattgtca ggatcaagtt cacttgaaga tcagaatact gtgaatgggc ctgtacagat     2820
tgtcaatgtg aaaacccttt ttagaaactc ttgtttcagt gaagaccaaa tggccaaacc     2880
tatcaaggca ttcacagctg actttgtgag gcagctcttg atagggctac ccaaccaagc    2940
cctcggactc acactgtgca gttttatcag tgctctgggt gtagacatca ttgctcaagt   3000
agaggcaaag gactttggtg ccgaaagcaa agtttctgtt gatgatctct gtaagaaagc   3060 ggtgaacat aacatccaga tagggaagtt ctctcagctg gttatgaaca gggcaactgt    3120
gttagcaagt tcttacgaca ctgcctggaa gaagcatgac ttggtgcgaa ggctagaaac    3180
cagtatttct tcttgtaaga caagcctgca gcgggttcag ctgcatattg ccatgtttca    3240
gtggcaacat gaagatctac ttatcaatag accacaagcc atgtcagtca cactcccccc   3300
acggtctgct atcctaacca gcatgaaaaa gaagctgcat accctgagcc agattgaaac   3360
ttctattgcg acagttcagg agaagctagc tgcacttgaa tcaagtattg aacagcgact   3420
caagtgggca ggtggtgcca accctgcatt ggcccctgta ctacaagatt ttgaagcaac   3480
gatagctgaa agaagaaatc ttgtccttaa agagagccaa agagcaagtc aggtcacatt   3540
tctctgcagc aatatcattc attttgaaag tttacgaaca agaactgcag aagccttaaa   3600
cctggatgcg gcgttatttg aactaatcaa gcgatgtcag cagatgtgtt cgtttgcatc    3660
acagtttaac agacactggt cttgaacatc ctattggcag ctctgaatgg cttttgtcag   3720
cacacaaaca gttgacccag gatatgtcta ctcagagggc aattcagaca gagaaagagc   3780
agcagataga aacggtctgt gaaacaattc agaatctggt tgataatata aagactgtgc   3840
tcactggtca taaccgacag cttggagatg tcaaacatct cttgaaagct atggctaagg   3900
atgaagaagc tgctctggcg gatggtgaag atgttcccta tgagaacagt gttaggcagt   3960 tttgggtga atataaatca tggcaagaca acattcaaac agttctattt acattagtcc   4020
aggctatggg tcaggttcga agtcaagaac acgttgaaat gctccaggaa atcactccca   4080
ccttgaaaga actgaaaaca caaagtcaga gtatctataa taatttagtg agttttgcat   4140 caccccttagt caccgatgca acaaatgaat gttcgagtcc aacgtcatct gctacttatc   4200
agccatcctt cgctgcagca gtccgagtaa cactggccag aagactcagc ctgatgtcat   4260
gtcacagaat gctagaaagc tgatccagaa aaatcttgct acatcagctg atactccacc   4320
aagcaccgtt ccaggaactg gcaagagtgt tgcttgtagt cctaaaaagg cagtcagaga   4380
ccctaaaact gggaaagcgg tgcaagagag aaactcctat gcagtgagtg tgtggaagag   4440
agtgaaagcc aagttagagg gccgagatgt tgatccgaat aggaggatgt cagttgctga   4500
acaggttgac tatgtcatta aggaagcaac taatctagat aacttggctc agctgtatga   4560
aggttggaca gcctgggtgc gaatggcaag acagtagaag ggcgaattcc                4610
```

<210> SEQ ID NO 5
<211> LENGTH: 4651
<212> TYPE: DNA
<213> ORGANISM: Homo sapiens

<400> SEQUENCE: 5

```
ggaattcgcc cttcggaacc atcacaatct taccgactaa aaccaagcca aagaaacttc    60
tctttcttgg atcagatggg aagagctatc cttatctttt caaaggactg gaggatttac   120
atctggatga gagaataatg cagttcctat ctattgtgaa taccatgttt gctacaatta   180
atcgccaaga aacaccccgg ttccatgctc gacactattc tgtaacacca ctaggaacaa   240
gatcaggact aatccagtgg gtagatggag ccacacccctt atttggtctt tacaaacgat   300
ggcaacaacg ggaagctgcc ttacaagcac aaaaggccca agattcctac caaactcctc   360
agaatcctgg aattgtaccc cgtcctagtg aactttatta cagtaaaatt ggccctgctt   420
tgaaaacagt tgggcttagc ctggatgtgt cccgtcggga ttggcctctt catgtaatga   480
aggcagtatt ggaagagtta atggaggcca cacccccgaa tctccttgcc aaagagctct   540
ggtcatcttg cacaacacct gatgaatggt ggagagttac gcagtcttat gcaagatcta   600
ctgcagtcat gtctatggtt ggatacataa ttggccttgg agacagacat ctggataatg   660
ttcttataga tatgacgact ggagaagttg ttcacataga ttacaatgtt tgctttgaaa   720
aaggtaaaag ccttagagtt cctgagaaag tacctttcg aatgacacaa acattgaaa    780
cagcactggg tgtaactgga gtagaaggtg tatttaggct ttcatgtgag caggttttac   840
acattatgcg gcgtggcaga gagaccctgc tgacgctgct ggaggccttt gtgtacgacc   900
ctctggtgga ctggacagca ggaggcgagg ctgggtttgc tggtgctgtc tatggtggag   960
gtggccagca ggccgagagc aagcagagca agagagagat ggagcgagag atcacccgca  1020
gcctgttttc ttctagagta gctgagatta aggtgaactg gtttaagaat agagatgaga  1080
tgctggttgt gcttcccaag ttggacggta gcttagatga atacctaagc ttgcaagagc  1140
aactgacaga tgtggaaaaa ctgcagggca aactactgga ggaaatagag tttctagaag  1200
gagctgaagg ggtggatcat ccttctcata ctctgcaaca caggtattct gagcacaccc  1260
aactacagac tcagcaaaga gctgttcagg aagcaatcca ggtgaagctg aatgaatttg  1320
aacaatggat aacacattat caggctgcat tcaataattt agaagcaaca cagcttgcaa  1380
gcttgcttca agagataagc acacaaatgg accttggtcc tccaagttac gtgccagcaa  1440
cagccttttct gcagaatgct ggtcaggccc acttgattag ccagtgcgag cagctggagg  1500
gggaggttgg tgctctcctg cagcagaggc gctctgtgct ccgtggctgt ctggagcaac  1560
tgcatcacta tgcaaccgtg gccctgcagt atccgaaggc catatttcag aaacatcgaa  1620
ttgaacagtg gaagacctgg atggaagagc tcatctgtaa caccacagta gagcgttgtc  1680
aagagctcta taggaaatat gaaatgcaat atgctcccca gccaccccca acagtgtgtc  1740
agttcatcac tgccactgaa atgaccctgc agcgatacgc agcagacatc aacagcagac  1800
ttattagaca agtggaacgc ttgaaacagg aagctgtcac tgtgccagtt tgtgaagatc  1860
agttgaaaga aattgaacgt tgcattaaag ttttccttca tgagaatgga gaagaaggat  1920
ctttgagtct agcaagtgtt attatttctg ccctttgtac ccttacaagg cgtaacctga  1980
tgatggaagg tgcagcgtca agtgctggag aacagctggt tgatctgact ctcgggatg   2040
gagcctggtt cttggaggaa ctctgcagta tgagcggaaa cgtcacctgc ttggttcagt  2100
tactgaagca gtgccacctg gtgccacagg acttagatat cccgaacccc atggaagcgt  2160
ctgagacagt tcacttagcc aatggagtgt atacctcact tcaggaattg aattcgaatt  2220
tccggcaaat catatttcca gaagcacttc gatgtttaat gaaagggaa tacacgttag   2280
aaagtatgct gcatgaactg gacggtctta ttgagcagac caccgatggc gttcccctgt  2340
```

-continued

```
agactctagt ggaatctctt caggcctact taagaaacgc agctatggga ctggaagaag      2400
aaacacatgc tcattacatc gatgttgcca gactactaca tgctcagtac ggtgaattaa      2460
tccaaccgag aaatggttca gttgatgaaa cacccaaaat gtcagctggc cagatgcttt      2520
tggtagcatt cgatggcatg tttgctcaag ttgaaactgc tttcagctta ttagttgaaa      2580
agttgaacaa gatggaaatt cccatagctt ggcgaaagat tgacatcata agggaagcca      2640
ggagtactca agttaatttt tttgatgatg ataatcaccg gcaggtgcta aagagattt       2700 tctttctaaa aaaactacag actattaagg agttcttcag gctctgtggt accttttcta      2760
aaacattgtc aggatcaagt tcacttgaag atcagaatac tgtgaatggg cctgtacaga      2820
ttgtcaatgt gaaaaccctt tttagaaact cttgtttcag tgaagaccaa atggccaaac      2880
ctatcaaggc attcacagct gactttgtga ggcagctctt gatagggcta cccaaccaag      2940
ccctcggact cacactgtgc agttttatca gtgctctggg tgtagacatc attgctcaag      3000
tagaggcaaa ggactttggt gccgaaagca agtttctgt tgatgatctc tgtaagaaag       3060
cggtggaaca taacatccag atagggaagt tctctcagct ggttatgaac agggcaactg      3120
tgttagcaag ttcttacgac actgcctgga agaagcatga cttggtgcga aggctagaaa      3180
ccagtatttc ttcttgtaag acaagcctgc agcgggttca gctgcatatt gccatgtttc      3240
agtggcaaca tgaagatcta cttatcaata gaccacaagc catgtcagtc acacctcccc      3300
cacggtctgc tatcctaacc agcatgaaaa agaagctgca taccctgagc cagattgaaa      3360
cttctattgc aacagttcag gagaagctag ctgcacttga atcaagtatt gaacagcgac      3420
tcaagtgggc aggtggtgcc aaccctgcat tggcccctgt actacaagat tttgaagcaa      3480
cgatagctga agaagaaat cttgtcctta agagagcca aagagcaagt caggtcacat        3540
ttctctgcag caatatcatt cattttgaaa gtttacgaac aagaactgca gaagccttaa      3600
acctggatgc ggcgttattt gaactaatca agcgatgtca gcagatgtgt tcgtttgcat      3660
cacagtttaa cagttcagtg tctgagttag agcttcgttt attacagaga gtggacactg      3720
gtcttgaaca tcctattggc agctctgaat ggcttttgtc agcacacaaa cagttgaccc      3780
aggatatgtc tactcagagg gcaattcaga cagagaaaga gcagcagata gaaacggtct      3840
gtgaaacaat tcagaatctg gttgataata taaagactgt gctcactggt cataaccgac      3900
agcttggaga tgtcaaacat ctcttgaaag ctatggctaa ggatgaagaa gctgctctgg      3960
cagatggtga agatgttccc tatgagaaca gtgttaggca gttttggggt gaatataaat      4020
catggcaaga caacattcaa acagttctat ttacattagt ccaggctatg ggtcaggttc      4080
gaagtcaaga acacgttgaa atgctccagg aaatcactcc caccttgaaa gaactgaaaa      4140
cacaaagtca gagtatctat aataatttag tgagttttgc atcacccctta gtcaccgatg     4200 caacaaatga atgttcgagt ccaacgtcac ctgctgctta tcagccatcc ttcgctgcag      4260
cagtccggag taacactggc cagaagactc agcctgatgt catgtcacag aatgctagaa      4320
agctgatcca gaaaaatctt gctacatcag ctgatactcc accaagcacc gttccaggaa      4380
ctggcaagag tgttgcttgt agtcctaaaa ggcagtcaga gaccctaaaa ctgggaaagc      4440
ggtgcaagag agaaactcct atgcagtgag tgtgtggaag agagtgaaag ccaagttaga      4500
gggccgagat gttgatccga ataggaggat gtcagttgct gaacaggttg actatgtcat      4560
taaggaagca actaatctag ataacttggc tcagctgtat gaaggttgga cagcctgggt      4620
gtgaatggca agacagtaga agggcgaatt c                                     4651
```

-continued

```
<210> SEQ ID NO 6
<211> LENGTH: 4495
<212> TYPE: DNA
<213> ORGANISM: Homo sapiens

<400> SEQUENCE: 6
gaattcgccc ttggacacga ggaaactgtt aatgacttgg gctttggaag cagctgtttt      60
aatgaagaag tctgaaacat acgcaccttt attctctctt ccgtctttcc ataaattttg     120
caaaggcctt ttagccaaca ctctcgttga agatgtgaat atctgtctgc aggcatgcag     180
cagtctacat gctctgtcct cttccttgcc agatgatctt ttacagagat gtgtcgatgt     240
ttgccgtgtt caactagtgc acagtggaac tcgtattcga caagcatttg gaaaactgtt     300
gaaatcaatt cctttagatg ttgtcctaag caataacaat cacacagaaa ttcaagaaat     360
ttctttagca ttaagaagcc acatgagtaa agcaccaagt aatacattcc accccaaga     420
tttctctgat gttattagtt ttattttgta tgggaactct catagaacag gaaggacaa     480
ttggttggaa agactgttct atagctgcca gagactggat aagcgtgacc agtcaacaat     540
tccacgcaat ctcctgaaga cagatgctgt cctttggcag tgggccatat gggaagctgc     600
acaattcact gttctttcta agctgagaac cccactgggc agagctcaag acaccttcca     660
gacaattgaa ggtatcattc gaagtctcgc agctcacaca ttaaaccctg atcaggatgt     720
tagtcagtgg acaactgcag acaatgatga aggccatggt aacaaccaac ttagacttgt     780
tcttcttctg cagtatctgg aaaatctgga gaaattaatg tataatgcat acgagggatg     840
tgctaatgca ttaacttcac ctcccaaggt cattagaact tttttctata ccaatcgcca     900
aacttgtcag gactggctaa cgcggattcg actctccatc atgagggtag gattgttggc     960
aggccagcct gcagtgacag tgagacatgg ctttgacttg cttacagaga tgaaaacaac    1020
cagcctatct caggggaatg aattggaagt aaccattatg atggtggtag aagcattatg    1080
tgaacttcat tgtcctgaag ctatacaggg aattgctgtc tggtcatcat ctattgttgg    1140
aaaaaatctt ctgtggatta actcagtggc tcaacaggct gaagggaggt ttgaaaaggc    1200
ctctgtggag taccaggaac acctgtgtgc catgacaggt gttgattgct gcatctccag    1260
ctttgacaaa tcggtgctca ccttagccaa tgctgggcgt aacagagcca gcccgaaaca    1320
ttctctgaat ggtgaatcca gaaaaactgt gctgtccaaa ccgactgact cttccctga    1380
ggttataaat tatttaggaa ataaagcatg tgagtgctac atctcaattg ccgattgggc    1440
tgctgtgcag gaatggcaga acgctatcca tgacttgaaa aagagtacca gtagcacttc    1500
cctcaacctg aaagctgact tcaactatat aaaatcatta gcagctttg agtctggaaa    1560
atttgttgaa tgtaccgagc agttagaatt gttaccagga gaaaatatca atctacttgc    1620
tggaggatca aaagaaaaaa tagacatgaa aaaactgctt cctaacatgt taagtccgga    1680
tccgagggaa cttcagaaat ccattgaagt tcaattgtta agaagttctg tttgtttggc    1740
aactgcttta aacccgatag aacaagatca gaagtggcag tctataactg aaaatgtggt    1800
aaagtacttg aagcaaacat cccgcatcgc tattggacct ctgagacttt ctactttaac    1860
agtttcacag tctttgccag ttctaagtac cttgcagctg tattgctcat ctgctttgga    1920
gaacacagtt tctaacagac tttcaacaga ggactgtctt attccactct tcagtgaagc    1980
tttacgttca tgtaaacagc atgacgtgag gccatggatg caggcattaa ggtatactat    2040
gtaccagaat cagttgttgg agaaaattaa agaacaaaca gtcccaatta gaagccatct    2100
catggaatta ggtctaacag cagcaaaatt tgctagaaaa cgagggaatg tgtcccttgc    2160
```

```
aacaagactg ctggcacagt gcagtgaagt tcagctggga aagaccacca ctgcacagga    2220
tttagtccaa cattttaaaa aactatcaac ccaaggtcaa gtggatgaaa aatgggggcc    2280
cgaacttgat attgaaaaaa ccaaattgct ttatacagca ggccagtcaa cacatgcaat    2340
ggaaatgttg agttcttgtg ccatatcttt ctgcaagtct gtgaaagctg aatatgcagt    2400
tgctaaatca attctgacac tggctaaatg gatccaggca gaatggaaag agatttcagg    2460
acagctgaaa caggtttaca gagctcagca ccaacagaac ttcacaggtc tttctacttt    2520
gtctaaaaac atactcactc taatagaact gccatctgtt aatacgatgg aagaagagta    2580
tcctcggatc gagagtgaat ctacagtgca tattggagtt ggagaacctg acttcatttt    2640
gggacagttg tatcacctgt cttcagtaca ggcacctgaa gtagccaaat cttgggcagc    2700
gttggccagc tgggcttata ggtggggcag aaaggtggtt gacaatgcca gtcagggaga    2760
aggtgttcgt ctgctgccta gagaaaaatc tgaagttcag aatctacttc cagacactat    2820
aactgaggaa gagaaagaga gaatatatgg tattcttgga caggctgtgt gtcggccggc    2880
ggggattcag gatgaagata taacacttca gataactgag agtgaagaca acgaagaaga    2940
tgacatggtt gatgttatct ggcgtcagtt gatatcaagc tgcccatggc tttcagaact    3000
tgatgaaagt gcaactgaag gagttattaa agtgtggagg aaagttgtag atagaatatt    3060
cagcctgtac aaactctctt gcagtgcata ctttactttc cttaaactca acgctggtca    3120
aattccttta gatgaggatg acctaggct gcatttaagt cacagagtgg aacagagcac    3180
tgatgacatg attgtgatgg ccacattgcg cctgctgcgg ttgctcgtga agcatgctgg    3240
tgagcttcgg cagtatctgg agcacggctt ggagacaaca cccactgcac catggagagg    3300
aattattccg caacttttct cacgcttaaa ccaccctgaa gtgtatgtgc gccaaagtat    3360
ttgtaacctt ctctgccgtg tggctcaaga ttccccacat ctcatattgt atcctgcaat    3420
agtgggtacc atatcgctta gtagtgaatc ccaggcttca ggaaataaat tttccactgc    3480
aattccaact ttacttggca atattcaagg agaagaattg ctggtttctg aatgtgaggg    3540
aggaagtcct cctgcatctc aggatagcaa taaggatgaa cctaaaagtg gattaaatga    3600
agaccaagcc atgatgcagg attgttatag caaaattgta gataagctgt cctctgcaaa    3660 cccccaccatg gtattacagg ttcagatgct cgtggctgaa ctgcgcaggg tcactgtgct    3720
ctgggatgag ctctggctgg gagttttgct gcaacaacac atgtatgtcc tgagacgaat    3780
tcagcagctt gaagatgagg tgaagagagt ccagaacaac aacaccttac gcaaagaaga    3840
gaaaattgca atcatgaggg agaagcacac agctttgatg aagcccatcg tatttgcttt    3900
ggagcatgtg aggagtatca cagcggctcc tgcagaaaca cctcatgaaa aatggtttca    3960
ggataactat ggtgatgcca ttgaaaatgc cctagaaaaa ctgaagactc cattgaaccc    4020
tgcaaagcct gggagcagct ggattccatt taaagagata atgctaagtt tgcaacagag    4080
agcacagaaa cgtgcaagtt acatcttgcg tcttgaagaa atcagtccat ggttggctgc    4140
catgactaac actgaaattg ctcttcctgg ggaagtctca gccagagaca ctgtcacaat    4200
ccatagtgtg ggcggaacca tcacaatctt accgactaaa accaagccaa agaaacttct    4260
ctttcttgga tcagatggga agagctatcc ttatcttttc aaaggactgg aggatttaca    4320
tctggatgag agaataatgc agttcctatc tattgtgaat accatgtttg ctacaattaa    4380
tcgccaagaa acaccccggt tccatgctcg acactattct gtaacaccac taggaacaag    4440
atcaggacta atccagtggg tagatggagc cacacccctta tttggtctttt acaab       4495
```

-continued

<210> SEQ ID NO 7
<211> LENGTH: 4534
<212> TYPE: DNA
<213> ORGANISM: Homo sapiens

<400> SEQUENCE: 7

| | | | | | |
|---|---|---|---|---|---|
| gaattcgccc | ttggacacga | ggaaactgtt | aatgacttgg | gctttggaag | cagctgtttt | 60 |
| aatgaagaag | tctgaaacat | acgcaccttt | attctctctt | ccgtctttcc | ataaattttg | 120 |
| caaaggcctt | ttagccaaca | ctctcgttga | agatgtgaat | atctgtctgc | aggcatgcag | 180 |
| cagtctacat | gctctgtcct | cttccttgcc | agatgatctt | ttacagagat | gtgtcgatgt | 240 |
| ttgccgtgtt | caactagtgc | acagtggaac | tcgtattcga | caagcatttg | gaaaactgtt | 300 |
| gaaatcaatt | cctttagatg | ttgtcctaag | caataacaat | cacacagaaa | ttcaagaaat | 360 |
| ttctttagca | ttaagaagtc | acatgagtaa | agcaccaagt | aatacattcc | accccccaaga | 420 |
| tttctctgat | gttattagtt | ttatttttgta | tgggaactct | catagaacag | ggaaggacaa | 480 |
| ttggttggaa | agactgttct | atagctgcca | gagactggat | aagcgtgacc | agtcaacaat | 540 |
| tccacgcaat | ctcctgaaga | cagatgctgt | cctttggcag | tgggccatat | gggaagctgc | 600 |
| acaattcact | gttctttcta | agctgagaac | cccactgggc | agagctcaag | acaccttcca | 660 |
| gacaattgaa | ggtatcattc | gaagtctcgc | agctcacaca | ttaaaccctg | atcaggatgt | 720 |
| tagtcagtgg | acaactgcag | acaatgatga | aggccatggt | aacaaccaac | ttagacttgt | 780 |
| tcttcttctg | cagtatctgg | aaaatctgga | gaaattaatg | tataatgcat | acgagggatg | 840 |
| tgctaatgca | ttaacttcac | ctcccaaggt | cattagaact | tttttctata | ccaatcgcca | 900 |
| aacttgtcag | gactggctaa | cgcggattcg | actctccatc | atgagggtag | gattgttggc | 960 |
| aggccagcct | gcagtgacag | tgagacatgg | ctttgacttg | cttacagaga | tgaaaacaac | 1020 |
| cagcctatct | caggggaatg | aattggaagt | aaccattatg | atggtggtag | aagcattatg | 1080 |
| tgaacttcat | tgtcctgaag | ctatacaggg | aattgctgtc | tggtcatcat | ctattgttgg | 1140 |
| aaaaaatctt | ctgtggatta | actcagtggc | tcaacaggct | gaagggaggt | ttgaaaaggc | 1200 |
| ctctgtggag | taccaggaac | acctgtgtgc | catgacaggt | gttgattgct | gcatctccag | 1260 |
| ctttgacaaa | tcggtgctca | ccttagccaa | tgctgggcgt | aacagtgcca | gcccgaaaca | 1320 |
| ttctctgaat | ggtgaatcca | gaaaaactgt | gctgtccaaa | ccgactgact | cttcccctga | 1380 |
| ggttataaat | tatttaggaa | ataaagcatg | tgagtgctac | atctcaattg | ccgattgggc | 1440 |
| tgctgtgcag | gaatggcaga | acgctatcca | tgacttgaaa | aagagtacta | gtagcacttc | 1500 |
| cctcaacctg | aaagctgact | tcaactatat | aaaatcatta | agcagctttg | agtctggaaa | 1560 |
| atttgttgaa | tgtaccgagc | agttagaatt | gttaccagga | gaaatatca | atctacttgc | 1620 |
| tggaggatca | aaagaaaaaa | tagacatgaa | aaaactgctt | cctaacatgt | taagtccgga | 1680 |
| tccgagggaa | cttcagaaat | ccattgaagt | tcaattgtta | agaagttctg | tttgtttggc | 1740 |
| aactgcttta | aacccgatag | aacaagatca | gaagtggcag | tctataactg | aaaatgtggt | 1800 |
| aaagtacttg | aagcaaacat | cccgcatcgc | tattggaccct | ctgagacttt | ctactttaac | 1860 |
| agtttcacag | tctttgccag | ttctaagtac | cttgcagctg | tattgctcat | ctgctttgga | 1920 |
| gaacacagtt | tctaacaggc | tttcaacaga | ggactgtctt | attccactct | tcagtgaagc | 1980 |
| tttacgttca | tgtaaacagc | atgacgtgag | gccatggatg | caggcattaa | ggtatactat | 2040 |
| gtaccagaat | cagttgttgg | agaaaattaa | agaacaaaca | gtcccaatta | gaagccatct | 2100 |
| catggaatta | ggtctaacag | cagcaaaatt | tgctagaaaa | cgagggaatg | tgtcccttgc | 2160 |

```
aacaagactg ctggcacagt gcagtgaagt tcagctggga aagaccacca ctgcacagga   2220
tttagtccaa cattttaaaa aactatcaac ccaaggtcaa gtggatgaaa aatgggggcc   2280
cgaacttgat attgaaaaaa ccaaattgct ttatacagca ggccagtcaa cacatgcaat   2340
ggaaatgttg agttcttgtg ccatatcttt ctgcaagtct gtgaaagctg aatatgcagt   2400
tgctaaatca attctgacac tggctaaatg gatccaggca gaatggaaag agatttcagg   2460
acagctgaaa caggtttaca gagctcagca ccaacagaac ttcacaggtc tttctacttt   2520
gtctaaaaac atactcactc taatagaact gccatctgtt aatacgatgg aagaagagta   2580
tcctcggatc gagagtgaat ctacagtgca tattggagtt ggagaacctg acttcatttt   2640
gggacagttg tatcacctgt cttcagtaca ggcacctgaa gtagccaaat cttgggcagc   2700
gttggccagc tgggcttata ggtggggcag aaaggtggtt gacaatgcca gtcagggaga   2760
aggtgttcgt ctgctgccta gagaaaaatc tgaagttcag aatctacttc cagacactat   2820
aactgaggaa gagaaagaga gaatatatgg tattcttgga caggctgtgt gtcggccggc   2880
ggggattcag gatgaagata taacacttca gataactgag agtgaagaca acgaagaaga   2940
tgacatggtt gatgttatct ggcgtcagtt gatatcaagc tgcccatggc tttcagaact   3000
tgatgaaagt gcaactgaag gagttattaa agtgtggagg aaagttgtag atagaatatt   3060
cagcctgtac aaactctctt gcagtgcata ctttactttc cttaaactca acgctggtca   3120
aattccttta gatgaggatg acctaggct gcatttaagt cacagagtgg aacagagcac   3180
tgatgacatg attgtgatgg ccacattgcg cctgctgcgg ttgctcgtga agcacgctgg   3240
tgagcttcgg cagtatctgg agcacggctt ggagacaaca cccactgcac catggagagg   3300
aattattccg caacttttct cacgcttaaa ccaccctgaa gtgtatgtgc gccaaagtat   3360
ttgtaacctt ctctgccgtg tggctcaaga ttccccacat ctcatattgt atcctgcaat   3420
agtgggtacc atatcgctta gtagtgaatc ccaggcttca ggaaataaat tttccactgc   3480
aattccaact ttacttggcg atattcaagg agaagaattg ctggtttctg aatgtgaggg   3540
aggaagtcct cctgcatctc aggatagcaa taaggatgaa cctaaaagtg gattaaatga   3600
agaccaagcc atgatgcagg attgttacag caaaattgta gataagctgt cctctgcaaa   3660
ccccaccatg gtattacagg ttcagatgct cgtggctgaa ctgcgcaggg tcactgtgct   3720
ctgggatgag ctctggctgg gagttttgct gcaacaacac atgtatgtcc tgagacgaat   3780
tcagcagctt gaagatgagg tgaagagagt ccagaacaac aacaccttac gcaaagaaga   3840
gaaaattgca atcatgaggg agaagcacac agctttgatg aagcccatcg tatttgcttt   3900
ggagcatgtg aggagtatca cagcggctcc tgcagaaaca cctcatgaaa aatggtttca   3960
ggataactat ggtgatgcca ttgaaaatgc cctagaaaaa ctgaagactc cattgaaccc   4020
tgcaaagcct gggagcagct ggattccatt taaagagata atgctaagtt tgcaacagag   4080
agcacagaaa cgtgcaagtt acatcttgcg tcttgaagaa atcagtccat ggttggctgc   4140
catgactaac actgaaattg ctcttcctgg ggaagtctca gccagagaca ctgtcacaat   4200
ccatagtgtg ggcggaacca tcacaatctt accgactaaa accaagccaa agaaacttct   4260
cttccttgga tcagatggga agagctatcc ttatcttttc aaaggactgg aggatttaca   4320
tctggatgag agaataatgc agttcctatc tattgtgaat accatgtttg ctacaattaa   4380
tcgccaagaa acaccccggt tccatgctcg cactattct gtaacaccac taggaacaag   4440
atcaggacta atccagtggg tagatggagc cacacccctta tttggtcttt acaaacgatg   4500
```

| gcaacaacgg gaagctgcct taaagggcga attc | 4534 |

<210> SEQ ID NO 8
<211> LENGTH: 4535
<212> TYPE: DNA
<213> ORGANISM: Homo sapiens

<400> SEQUENCE: 8

| gaattcgccc ttggacacga ggaaactgtt aatgacttgg gctttggaag cagctgtttt | 60 |
| aatgaagaag tctgaaacat acgcacctttt attctctctt ccgtctttcc ataaattttg | 120 |
| caaaggcctt ttagccaaca ctctcgttga agatgtgaat atctgtctgc aggcatgcag | 180 |
| cagtctacat gctctgtcct cttccttgcc agatgatctt ttacagagat gtgtcgatgt | 240 |
| ttgccgtgtt caactagtgc acagtggaac tcgtattcga caagcatttg gaaaactgtt | 300 |
| gaaatcaatt cctttagatg ttgtcctaag caataacaat cacacagaaa ttcaagaaat | 360 |
| ttctttagca ttaagaagtc acatgagtaa agcaccaagt aatacattcc accccccaaga | 420 |
| tttctctgat gttattagtt ttattttgta tgggaactct catagaacag ggaaggacaa | 480 |
| ttggttggaa agactgttct atagctgcca gagactggat aagcgtgacc agtcaacaat | 540 |
| tccacgcaat ctcctgaaga cagatgctgt cctttggcag tgggccatat gggaagctgc | 600 |
| acaattcact gttctttcta agctgagaac cccactgggc agagctcaag acaccttcca | 660 |
| gacaattgaa ggtatcattc gaagtctcgc agctcacaca ttaaaccctg atcaggatgt | 720 |
| tagtcagtgg acaactgcag acaatgatga aggccatggt aacaaccaac ttagacttgt | 780 |
| tcttcttctg cagtatctgg aaaatctgga gaaattaatg tataatgcat acgagggatg | 840 |
| tgctaatgca ttaacttcac ctcccaaggt cattagaact tttttctata ccaatcgcca | 900 |
| aacttgtcag gactggctaa cgcggattcg actctccatc atgagggtag gattgttggc | 960 |
| aggccagcct gcagtgacag tgagacacg ctttgacttg cttacagaga tgaaaacaac | 1020 |
| cagcctatct caggggaatg aattggaagt aaccattatg atggtggtag aagcattatg | 1080 |
| tgaacttcat tgtcctgaag ctatacaggg aattgctgtc tggtcatcat ctattgttgg | 1140 |
| aaaaaatctt ctgtggatta actcagtggc tcaacaggct gaagggaggt ttgaaaaggc | 1200 |
| ctctgtggag taccaggaac acctgtgtgc catgacaggt gttgattgct gcatctccag | 1260 |
| cttttgacaaa tcggtgctca ccttagccaa tgctgggcgt aacagtgcca gcccgaaaca | 1320 |
| ttctctgaat ggtgaatcca gaaaaactgt gctgtccaaa ccgactgact cttcccctga | 1380 |
| ggttataaat tatttaggaa ataaagcatg tgagtgctac atctcaattg ccgattgggc | 1440 |
| tgctgtgcag gaatggcaga acgctatcca tgcttgaaaa agagtacca gtagcacttc | 1500 |
| cctcaacctg aaagctgact tcaactatat aaaatcatta agcagctttg agtctggaaa | 1560 |
| atttgttgaa tgtaccgagc agttagaatt gttaccagga gaaaatatca atctacttgc | 1620 |
| tggaggatca aagaaaaaa tagacatgaa aaaactgctt cctaacatgt taagtccgga | 1680 |
| tccgagggaa cttcagaaat ccattgaagt tcaattgtta agaagttctg tttgtttggc | 1740 |
| aactgcttta aacccgatag aacaagatca gaagtggcag tctataactg aaaatgtggt | 1800 |
| aaagtacttg aagcaaacat cccgcatcgc tattggacct ctgagacttt ctactttaac | 1860 |
| agtttcacag tcttttgccag ttctaagtac cttgcagctg tattgctcat ctgctttgga | 1920 |
| gaacacagtt tctaacagac tttcaacaga ggactgtctt attccactct tcagtgaagc | 1980 |
| tttacgttca tgtaaacagc atgacgtgag gccatggatg caggcattaa ggtatactat | 2040 |
| gtaccagaat cagttgttgg agaaaattaa agaacaaaca gtcccaatta gaagccatct | 2100 |

```
catgaatta ggtctaacag cagcaaaatt tgctagaaaa cgagggaatg tgtcccttgc      2160
aacaagactg ctggcacagt gcagtgaagt tcagctggga aagaccacca ctgcacagga      2220
tttagtccaa cattttaaaa aactatcaac ccaaggtcaa gtggatgaaa atgggggcc       2280 cgaacttgat attgaaaaaa ccaaattgct ttatacagca ggccagtcaa cacatgcaat      2340
ggaaatgttg agttcttgtg ccatatcttt ctgcaagtct gtgaaagctg aatatgcagt      2400
tgctaaatca attctgacac tggctaaatg gatccaggca gaatggaaag agatttcagg      2460
acagctgaaa caggtttaca gagctcagca ccaacagaac ttcacaggtc tttctacttt      2520
gtctaaaaac atactcactc taatagaact gccatctgtt aatacgatgg aagaagagta      2580
tcctcggatc gagagtgaat ctacagtgca tattggagtt ggagaacctg acttcatttt      2640
gggacagttg tatcacctgt cttcagtaca ggcacctgaa gtagccaaat cttgggcagc      2700
gttggccagc tgggcttata ggtggggcag aaaggtggtt gacaatgcca gtcagggaga      2760
aggtgttcgt ctgctgccta gagaaaaatc tgaagttcag aatctacttc cagacactat      2820
aactgaggaa gagaaagaga gaatatatgg tattcttgga caggctgtgt gtcggccggc      2880
ggggattcag gatgaagata taacacttca gataactgag agtgaagaca cgaagaaga       2940 tgacatggtt gatgttatct ggcgtcagtt gatatcaagc tgcccatggc tttcagaact      3000
tgatgaaagt gcaactgaag gagttattaa agtgtggagg aaagttgtag atagaatatt      3060
cagcctgtac aaactctctt gcagtgcata ctttactttc cttaaactca acgctggtca      3120
aattccttta gatgaggatg accctaggct gcatttaagt cacagagtgg aacagagcac      3180
tgatgacatg attgtgatgg ccacattgcg cctgctgcgg ttgctcgtga agcacgctgg      3240
tgagcttcgg cagtatctgg agcacggctt ggagacaaca cccactgcac catggagagg      3300
aattattccg caacttttct cacgcttaaa ccaccctgaa gtgtatgtgc gccaaagtat      3360
ttgtaacctt ctctgccgtg tggctcaaga ttcccccacat ctcatattgt atcctgcaat      3420
agtgggtacc atatcgctta gtagtgaatc ccaggcttca ggaaataaat tttccactgc      3480
aattccaact ttacttggca atattcaagg agaagaattg ctggtttctg aatgtgaggg      3540
aggaagtcct cctgcatctc aggatagcaa taaggatgaa cctaaaagtg gattaaatga      3600
agaccaagcc atgatgcagg attgttacag caaaattgta gataagctgt cctctgcaaa      3660
ccccaccatg gtattacagg ttcagatgct cgtggctgaa ctgcgcaggg tcactgtgct      3720
ctgggatgag ctctggctgg gagttttgct gcaacaacac atgtatgtcc tgagacgaat      3780
tcagcagctt gaagatgagg tgaagagagt ccagaacaac aacaccttac gcaaagaaga      3840
gaaaattgca atcatgaggg agaagcacac agctttgatg aagcccatcg tatttgcttt      3900
ggagcatgtg aggagtatca cagcggctcc tgcagaaaca cctcatgaaa aatggtttca      3960
ggataactat ggtgatgcca ttgaaaatgc cctagaaaaa ctgaagactc cattgaaccc      4020
tgcaaagcct gggagcagct ggattccatt taaagagata atgctaagtt tgcaacagag      4080
agcacagaaa cgtgcaagtt acatcttgcg tcttgaagaa atcagtccat ggttggctgc      4140
catgactaac actgaaattg ctcttcctgg ggaagtctca gccagagaca ctgtcacaat      4200
ccatagtgtg ggcggaacca tcacaatctt accgactaaa accaagccaa agaaacttct      4260 cttttcttgga tcagatggga agagctatcc ttatctttc aaaggactgg aggatttaca      4320
tctggatgag agaataatgc agttcctatc tattgtgaat accatgtttg ctacaattaa      4380
tcgccaagaa acacccccggt tccatgctcg acactattct gtaacaccac taggaacaag      4440
```

-continued

```
atcaggacta atccagtggg tagatggagc cacaccctta tttggtctttt acaaacgatg    4500 gcaacaacgg gaagctgcct taaagggcga attcc                                4535
```

<210> SEQ ID NO 9
<211> LENGTH: 20
<212> TYPE: DNA
<213> ORGANISM: Artificial sequence
<220> FEATURE:
<223> OTHER INFORMATION: primer 19F

<400> SEQUENCE: 9

```
gggcggaacc atcacaatct                                                   20
```

<210> SEQ ID NO 10
<211> LENGTH: 20
<212> TYPE: DNA
<213> ORGANISM: Artificial sequence
<220> FEATURE:
<223> OTHER INFORMATION: primer 22F

<400> SEQUENCE: 10

```
cggaaccatc acaatcttac                                                   20
```

<210> SEQ ID NO 11
<211> LENGTH: 20
<212> TYPE: DNA
<213> ORGANISM: Artificial sequence
<220> FEATURE:
<223> OTHER INFORMATION: primer 299R

<400> SEQUENCE: 11

```
cgttgttgcc atcgtttgta                                                   20
```

<210> SEQ ID NO 12
<211> LENGTH: 20
<212> TYPE: DNA
<213> ORGANISM: Artificial sequence
<220> FEATURE:
<223> OTHER INFORMATION: primer 312R

<400> SEQUENCE: 12

```
taaggcagct tcccgttgtt                                                   20
```

<210> SEQ ID NO 13
<211> LENGTH: 27
<212> TYPE: DNA
<213> ORGANISM: Artificial sequence
<220> FEATURE:
<223> OTHER INFORMATION: primer AP-1

<400> SEQUENCE: 13

```
ccatcctaat acgactcact atagggc                                           27
```

<210> SEQ ID NO 14
<211> LENGTH: 24
<212> TYPE: DNA
<213> ORGANISM: Artificial Sequence
<220> FEATURE:
<223> OTHER INFORMATION: primer 19Fext

<400> SEQUENCE: 14

```
gggcggaacc atcacaatct tacc                                              24
```

<210> SEQ ID NO 15
<211> LENGTH: 25

```
<212> TYPE: DNA
<213> ORGANISM: Artificial Sequence
<220> FEATURE:
<223> OTHER INFORMATION: primer 22Fext

<400> SEQUENCE: 15
cggacccatc acaatcttac cgact                                          25

<210> SEQ ID NO 16
<211> LENGTH: 25
<212> TYPE: DNA
<213> ORGANISM: Artificial Sequence
<220> FEATURE:
<223> OTHER INFORMATION: primer 299Rext

<400> SEQUENCE: 16
cgttgttgcc atcgtttgta aagac                                          25

<210> SEQ ID NO 17
<211> LENGTH: 24
<212> TYPE: DNA
<213> ORGANISM: Artificial Sequence
<220> FEATURE:
<223> OTHER INFORMATION: primer 312Rext

<400> SEQUENCE: 17
taaggcagct tcccgttgtt gcca                                           24

<210> SEQ ID NO 18
<211> LENGTH: 23
<212> TYPE: DNA
<213> ORGANISM: Artificial Sequence
<220> FEATURE:
<223> OTHER INFORMATION: primer AP-2

<400> SEQUENCE: 18
actcactata gggctcgagc ggc                                            23

<210> SEQ ID NO 19
<211> LENGTH: 27
<212> TYPE: DNA
<213> ORGANISM: Artificial Sequence
<220> FEATURE:
<223> OTHER INFORMATION: primer 15158

<400> SEQUENCE: 19
ccacctccac caatagagag caccagc                                        27

<210> SEQ ID NO 20
<211> LENGTH: 24
<212> TYPE: DNA
<213> ORGANISM: Artificial Sequence
<220> FEATURE:
<223> OTHER INFORMATION: primer 15156

<400> SEQUENCE: 20
gctctgcttg ctctcggcct gctg                                           24

<210> SEQ ID NO 21
<211> LENGTH: 24
<212> TYPE: DNA
<213> ORGANISM: Artificial Sequence
<220> FEATURE:
<223> OTHER INFORMATION: primer 15157

<400> SEQUENCE: 21
```

```
ggacttgctc gtcttgctct cggc                                    24

<210> SEQ ID NO 22
<211> LENGTH: 24
<212> TYPE: DNA
<213> ORGANISM: Artificial Sequence
<220> FEATURE:
<223> OTHER INFORMATION: primer 3'E2F

<400> SEQUENCE: 22
gtctatggtg gaggtggcca gcag                                    24

<210> SEQ ID NO 23
<211> LENGTH: 26
<212> TYPE: DNA
<213> ORGANISM: Artificial Sequence
<220> FEATURE:
<223> OTHER INFORMATION: primer KIDrev

<400> SEQUENCE: 23
gatgtcaatc tttcgccaag ctatgg                                  26

<210> SEQ ID NO 24
<211> LENGTH: 21
<212> TYPE: DNA
<213> ORGANISM: Artificial Sequence
<220> FEATURE:
<223> OTHER INFORMATION: primer SLQrev

<400> SEQUENCE: 24
gctgcaggct tgtcttacaa c                                       21

<210> SEQ ID NO 25
<211> LENGTH: 22
<212> TYPE: DNA
<213> ORGANISM: Artificial Sequence
<220> FEATURE:
<223> OTHER INFORMATION: primer MCSrev

<400> SEQUENCE: 25
gcaagctcta actcagacac tg                                      22

<210> SEQ ID NO 26
<211> LENGTH: 22
<212> TYPE: DNA
<213> ORGANISM: Artificial Sequence
<220> FEATURE:
<223> OTHER INFORMATION: primer SSArev

<400> SEQUENCE: 26
gcagatgacg ttggactcga ac                                      22

<210> SEQ ID NO 27
<211> LENGTH: 22
<212> TYPE: DNA
<213> ORGANISM: Artificial Sequence
<220> FEATURE:
<223> OTHER INFORMATION: primer MARQrev

<400> SEQUENCE: 27
ctactgtctt gccattcaca cc                                      22

<210> SEQ ID NO 28
<211> LENGTH: 24
<212> TYPE: DNA
<213> ORGANISM: Artificial Sequence
```

```
<220> FEATURE:
<223> OTHER INFORMATION: primer RLLfor

<400> SEQUENCE: 28
cagactacta catgctcagt acgg                                          24

<210> SEQ ID NO 29
<211> LENGTH: 27
<212> TYPE: DNA
<213> ORGANISM: Artificial Sequence
<220> FEATURE:
<223> OTHER INFORMATION: primer TRTrev

<400> SEQUENCE: 29
ccaggtttat ggcttctgca gttcttg                                       27

<210> SEQ ID NO 30
<211> LENGTH: 24
<212> TYPE: DNA
<213> ORGANISM: Artificial Sequence
<220> FEATURE:
<223> OTHER INFORMATION: primer 19AS

<400> SEQUENCE: 30
ggtaagattg tgatggttcc gccc                                          24

<210> SEQ ID NO 31
<211> LENGTH: 24
<212> TYPE: DNA
<213> ORGANISM: Artificial Sequence
<220> FEATURE:
<223> OTHER INFORMATION: primer 5'E2R

<400> SEQUENCE: 31
gcacgtttct gtgctctctg ttgc                                          24

<210> SEQ ID NO 32
<211> LENGTH: 29
<212> TYPE: DNA
<213> ORGANISM: Artificial Sequence
<220> FEATURE:
<223> OTHER INFORMATION: primer STDrev

<400> SEQUENCE: 32
ggccatccac aatcatgtca tcagtgctc                                     29

<210> SEQ ID NO 33
<211> LENGTH: 28
<212> TYPE: DNA
<213> ORGANISM: Artificial Sequence
<220> FEATURE:
<223> OTHER INFORMATION: primer PIRrev

<400> SEQUENCE: 33
ctaattccat gagatggctt ctaattgg                                      28

<210> SEQ ID NO 34
<211> LENGTH: 24
<212> TYPE: DNA
<213> ORGANISM: Artificial Sequence
<220> FEATURE:
<223> OTHER INFORMATION: primer CECrev

<400> SEQUENCE: 34
cggcaattga gatgtagcac tcac                                          24
```

```
<210> SEQ ID NO 35
<211> LENGTH: 28
<212> TYPE: DNA
<213> ORGANISM: Artificial Sequence
<220> FEATURE:
<223> OTHER INFORMATION: primer MTWfor

<400> SEQUENCE: 35
atgacttggg ctttggaagt agctgttg                                          28

<210> SEQ ID NO 36
<211> LENGTH: 30
<212> TYPE: DNA
<213> ORGANISM: Artificial Sequence
<220> FEATURE:
<223> OTHER INFORMATION: primer MTWfor2

<400> SEQUENCE: 36
ggacacgagg aaactgttaa tgacttgggc                                        30

<210> SEQ ID NO 37
<211> LENGTH: 26
<212> TYPE: DNA
<213> ORGANISM: Artificial Sequence
<220> FEATURE:
<223> OTHER INFORMATION: primer MFA-F

<400> SEQUENCE: 37
catgtttgct acaattaatc gccaag                                            26

<210> SEQ ID NO 38
<211> LENGTH: 23
<212> TYPE: DNA
<213> ORGANISM: Artificial Sequence
<220> FEATURE:
<223> OTHER INFORMATION: primer TSQ-R

<400> SEQUENCE: 38
gactgcgtaa ctctccacca ttc                                               23

<210> SEQ ID NO 39
<211> LENGTH: 83
<212> TYPE: DNA
<213> ORGANISM: Artificial Sequence
<220> FEATURE:
<223> OTHER INFORMATION: primer ATR2-LTRfor

<400> SEQUENCE: 39
ctagctagcg gatccgaatc acacagctca ccaccatgga ctataaagat gacgatgaca       60
agggaacatt gctgcggttg ctc                                               83

<210> SEQ ID NO 40
<211> LENGTH: 35
<212> TYPE: DNA
<213> ORGANISM: Artificial Sequence
<220> FEATURE:
<223> OTHER INFORMATION: primer ATR2-LDrev

<400> SEQUENCE: 40
gcgtgtcaga ctcatcctgc tgtccagtcc accag                                  35

<210> SEQ ID NO 41
<211> LENGTH: 660
<212> TYPE: DNA
<213> ORGANISM: Homo sapiens
```

```
<400> SEQUENCE: 41
gatctgactt ctcgggatgg agcctggttc ttggaggaac tctgcagtat gagcggaaac      60
gtcacctgct tggttcagtt actgaagcag tgccacctgg tgccacagga cttagatatc     120
ccgaacccca tggaagcgtc tgagacagtt cacttagcca atggagtgta tacctcactt     180
caggaattga attcgaattt ccggcaaatc atatttccag aagcacttcg atgtttaatg     240 aaagggaat acacgttaga aagtatgctg catgaactgg acggtcttat tgagcagacc      300
accgatggcg ttccctgca gactctagtg gaatctcttc aggcctactt aagaaacgca      360
gctatgggac tggaagaaga aacacatgct cattacatcg atgttgccag actactacat     420
gctcagtacg gtgaattaat ccaaccgaga aatggttcag ttgatgaaac acccaaaatg     480
tcagctggcc agatgctttt ggtagcattc gatggcatgt ttgctcaagt tgaaactgct     540
ttcagcttat tagttgaaaa gttgaacaag atggaaattc ccatagcttg gcgaaagatt     600
gacatcataa gacctgcccg ggcggccgct cgagccctat agtgagtaag ggcgaattcc     660

<210> SEQ ID NO 42
<211> LENGTH: 1207
<212> TYPE: DNA
<213> ORGANISM: Homo sapiens

<400> SEQUENCE: 42
cggccgccag tgtgctggaa ttcgcccttg gccatccaca atcatgtcat cagtgctctg      60
ttccactctg tgacttaaat gcagcctagg gtcatcctca tctaaaggaa tttgaccagc     120
gttgagttta aggaaagtaa agtatgcact gcaagagagt ttgtacaggc tgaatattct     180
atctacaact ttcctccaca ctttaataac tccttcagtt gcactttcat caagttctga     240
aagccatggg cagcttgata tcaactgacg ccagataaca tcaaccatgt catcttcttc     300
gttgtcttca ctctcagtta tctgaagtgt tatatcttca tcctgaatcc cgccggccg      360 acacacagcc tgtccaagaa taccatatat tctctccttc tcttcctcag ttatagtgtc     420
tggaagtaga ttctgaactt cagatttttc tctaggcagc agacgaacac cttctccctg     480
actggcattg tcaaccacct ttctgcccca cctataagcc cagctggcca acgctgccca     540
agatttggct acttcaggtg cctgtactga aggcaggtga tacaactgtc ccaaaatgaa     600
gtcaggttct ccaactccaa tatgcactgt agattcactc tcgatccgag gatactcttc     660
ttccatcgta ttaacagatg gcagttctat tagagtgagt atgttttttag acaaagtaga     720 aagacctgtg aagttctgtt ggtgctgagc tctgtaaacc tgtttcagct gtcctgaaat     780
ctctttccat tctgcctgga tccatttagc cagtgtcaga attgatttag caactgcata     840
ttcagctttc acagacttgc agaaagatat ggcacaagaa ctcaacattt ccattgcatg     900
tgttgactgg cctgctgtat aaagcaattt ggttttttca atatcaagtt cgggccccca     960
tttttcatcc acttgacctt gggttgatag ttttttaaaa tgttggacta atcctgtgc     1020 agtggtggtc tttcccagct gaacttcact gcactgtgcc agcagtcttg ttgcaaggga    1080
cacattccct cgttttctag caaattttgc tgctgttaga cctaattcca tgagatggct    1140
tctaattggg actgtttgtt ctttaatttt ctccaacaac tgattctgga cctgcccggg    1200
cggccgc                                                             1207

<210> SEQ ID NO 43
<211> LENGTH: 443
<212> TYPE: DNA
```

```
<213> ORGANISM: Homo sapiens

<400> SEQUENCE: 43
tctactgcag tcatgtctat ggttggatac ataattggcc ttggagacag acatctggat      60
aatgttctta tagatatgac gactggagaa gttgttcaca tagattacaa tgtttgcttt     120
gaaaaaggta aaagccttag agttcctgag aaagtacttt ttcgaatgac acaaaacatt     180
gaaacagcac tgggtgtaac tggagtagaa ggtgtattta ggctttcatg tgagcaggtt     240
ttacacatta tgcggcgtgg cagagagacc ctgctgacgc tgctggaggc ctttgtgtac     300
gaccctctgg tggactggac agcaggaggc gaggctgggt ttgctggtgc tgtctatggt     360
ggaggtggcc agcaggccga gagcaagcag agcaagacct gcccgggcgg ccgctcgagc     420
cctatagtga gtaagccgaa ttc                                             443
```